United States Patent
Maharvi et al.

(10) Patent No.: US 11,970,431 B2
(45) Date of Patent: Apr. 30, 2024

(54) POLYMERIZABLE ABSORBERS OF UV AND HIGH ENERGY VISIBLE LIGHT

(71) Applicant: Johnson & Johnson Vision Care, Inc., Jacksonville, FL (US)

(72) Inventors: Ghulam Maharvi, Jacksonville, FL (US); Shivkumar Mahadevan, Jacksonville, FL (US); Stephen C. Arnold, Jacksonville, FL (US); Patricia Martin, Jacksonville, FL (US); Leilani K. Sonoda, Atlantic Beach, FL (US); Dola Sinha, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 51 days.

(21) Appl. No.: 17/332,416

(22) Filed: May 27, 2021

(65) Prior Publication Data

US 2021/0309600 A1    Oct. 7, 2021

Related U.S. Application Data

(62) Division of application No. 16/398,722, filed on Apr. 30, 2019, now Pat. No. 11,046,636.
(Continued)

(51) Int. Cl.
*G02B 1/04*     (2006.01)
*C07C 69/738*   (2006.01)
(Continued)

(52) U.S. Cl.
CPC .......... *C07C 225/22* (2013.01); *C07C 69/738* (2013.01); *C07C 233/38* (2013.01);
(Continued)

(58) Field of Classification Search
None
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| | (Continued) | |

FOREIGN PATENT DOCUMENTS

| | | | |
|---|---|---|---|
| CA | 2771138 A1 | * | 3/2011 |
| EP | 0080539 B1 | | 6/1983 |
| | (Continued) | | |

OTHER PUBLICATIONS

Chuang et al, 2-Amino-3,4,5-Trimethoxybenzophenones as Potent Tubulin Polymerization Inhibitors, ChemMedChem, 2011, vol. 6, pp. 450-456.
(Continued)

*Primary Examiner* — Tae H Yoon
(74) *Attorney, Agent, or Firm* — Raef M. Shaltout

(57) ABSTRACT

Described are polymerizable high energy light absorbing compounds of formula I:

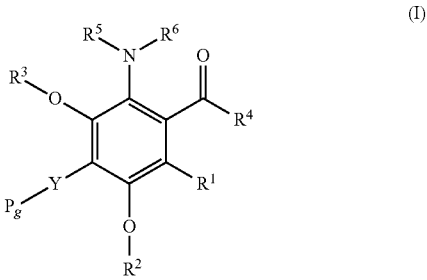

(Continued)

UV-VIS Transmission Spectra of 0.2 mM methanol solutions of Compounds (F), (M), and (P)

Wherein Y, Pg, $R^2$, $R^3$, $R^4$, $R^5$, and $R^6$ are as described herein. The compounds absorb various wavelengths of ultraviolet and/or high energy visible light and are suitable for incorporation in various products, such as biomedical devices and ophthalmic devices.

12 Claims, 7 Drawing Sheets

Related U.S. Application Data

(60) Provisional application No. 62/691,666, filed on Jun. 29, 2018.

(51) Int. Cl.
*C07C 225/22* (2006.01)
*C07C 233/38* (2006.01)
*C07C 233/42* (2006.01)
*C08K 3/18* (2006.01)
*C08K 5/18* (2006.01)
*C08K 5/20* (2006.01)
*C08L 83/04* (2006.01)

(52) U.S. Cl.
CPC .............. *C07C 233/42* (2013.01); *C08K 5/18* (2013.01); *C08K 5/20* (2013.01); *C08L 83/04* (2013.01); *G02B 1/043* (2013.01); *C08K 2201/00* (2013.01); *C08L 2203/02* (2013.01)

(56) References Cited

U.S. PATENT DOCUMENTS

| | | |
|---|---|---|
| 3,808,178 A | 4/1974 | Gaylord |
| 4,113,224 A | 9/1978 | Clark et al. |
| 4,120,570 A | 10/1978 | Gaylord |
| 4,136,250 A | 1/1979 | Mueller et al. |
| 4,153,641 A | 5/1979 | Deichert et al. |
| 4,197,266 A | 4/1980 | Clark et al. |
| 4,436,887 A | 3/1984 | Chromecek et al. |
| 4,495,313 A | 1/1985 | Larsen |
| 4,659,782 A | 4/1987 | Spinelli |
| 4,659,783 A | 4/1987 | Spinelli |
| 4,740,533 A | 4/1988 | Su et al. |
| 4,889,664 A | 12/1989 | Kindt-Larsen et al. |
| 4,910,277 A | 3/1990 | Bambury et al. |
| 5,006,622 A | 4/1991 | Kunzler et al. |
| 5,034,461 A | 7/1991 | Lai et al. |
| 5,039,459 A | 8/1991 | Kindt-Larsen et al. |
| 5,070,215 A | 12/1991 | Bambury et al. |
| 5,236,969 A | 8/1993 | Kunzler et al. |
| 5,244,981 A | 9/1993 | Seidner et al. |
| 5,270,418 A | 12/1993 | Kunzler et al. |
| 5,298,533 A | 3/1994 | Nandu et al. |
| 5,314,960 A | 5/1994 | Spinelli et al. |
| 5,331,067 A | 7/1994 | Seidner et al. |
| 5,371,147 A | 12/1994 | Spinelli et al. |
| 5,681,871 A | 10/1997 | Molock et al. |
| 5,760,100 A | 6/1998 | Nicolson et al. |
| 5,776,999 A | 7/1998 | Nicolson et al. |
| 5,789,461 A | 8/1998 | Nicolson et al. |
| 5,824,719 A | 10/1998 | Kunzler et al. |
| 5,849,811 A | 12/1998 | Nicolson et al. |
| 5,962,548 A | 10/1999 | Vanderlaan et al. |
| 5,965,631 A | 10/1999 | Nicolson et al. |
| 5,998,498 A | 12/1999 | Vanderlaan et al. |
| 6,020,445 A | 2/2000 | Vanderlaan et al. |
| 6,087,415 A | 7/2000 | Vanderlaan et al. |
| 6,367,929 B1 | 4/2002 | Maiden et al. |
| 6,420,453 B1 | 7/2002 | Bowers et al. |
| 6,423,761 B1 | 7/2002 | Bowers et al. |
| 6,767,979 B1 | 7/2004 | Muir et al. |
| 6,822,016 B2 | 11/2004 | McCabe et al. |
| 6,867,245 B2 | 3/2005 | Iwata et al. |
| 6,943,203 B2 | 9/2005 | Vanderlaan et al. |
| 6,951,894 B1 | 10/2005 | Nicolson et al. |
| 7,052,131 B2 | 5/2006 | McCabe et al. |
| 7,247,692 B2 | 7/2007 | Laredo |
| 7,249,848 B2 | 7/2007 | Laredo et al. |
| 7,396,890 B2 | 7/2008 | Zanini et al. |
| 7,461,937 B2 | 12/2008 | Steffen et al. |
| 7,468,398 B2 | 12/2008 | Nicolson et al. |
| 7,538,146 B2 | 5/2009 | Nicolson et al. |
| 7,553,880 B2 | 6/2009 | Nicolson et al. |
| 7,572,841 B2 | 8/2009 | Chen et al. |
| 7,666,921 B2 | 2/2010 | McCabe et al. |
| 7,691,916 B2 | 4/2010 | McCabe et al. |
| 7,786,185 B2 | 8/2010 | Rathore et al. |
| 7,825,170 B2 | 11/2010 | Steffen et al. |
| 7,915,323 B2 | 3/2011 | Awasthi et al. |
| 7,934,830 B2 | 5/2011 | Blackwell et al. |
| 7,956,131 B2 | 6/2011 | Arnold et al. |
| 7,994,356 B2 | 8/2011 | Awasthi et al. |
| 8,022,158 B2 | 9/2011 | Rathore et al. |
| 8,026,326 B2 | 9/2011 | Benz et al. |
| 8,138,290 B2 | 3/2012 | Blackwell et al. |
| 8,163,206 B2 | 4/2012 | Chang et al. |
| 8,273,802 B2 | 9/2012 | Laredo et al. |
| 8,360,574 B2 | 1/2013 | Ishak et al. |
| 8,389,597 B2 | 3/2013 | Blackwell et al. |
| 8,399,538 B2 | 3/2013 | Steffen et al. |
| 8,415,404 B2 | 4/2013 | Nicolson et al. |
| 8,420,711 B2 | 4/2013 | Awasthi et al. |
| 8,450,387 B2 | 5/2013 | McCabe et al. |
| 8,470,906 B2 | 6/2013 | Rathore et al. |
| 8,487,058 B2 | 7/2013 | Liu et al. |
| 8,507,577 B2 | 8/2013 | Zanini et al. |
| 8,568,626 B2 | 10/2013 | Nicolson et al. |
| 8,618,323 B2 | 12/2013 | Benz et al. |
| 8,637,621 B2 | 1/2014 | Iwata et al. |
| 8,703,891 B2 | 4/2014 | Broad |
| 8,937,110 B2 | 1/2015 | Alli et al. |
| 8,937,111 B2 | 1/2015 | Alli et al. |
| 8,940,812 B2 | 1/2015 | Reboul et al. |
| 8,980,972 B2 | 3/2015 | Driver |
| 9,056,878 B2 | 6/2015 | Fujisawa et al. |
| 9,057,821 B2 | 6/2015 | Broad et al. |
| 9,125,808 B2 | 9/2015 | Alli et al. |
| 9,140,825 B2 | 9/2015 | Alli et al. |
| 9,156,934 B2 | 10/2015 | Alli et al. |
| 9,170,349 B2 | 10/2015 | Mahadevan et al. |
| 9,217,813 B2 | 12/2015 | Liu et al. |
| 9,244,196 B2 | 1/2016 | Scales et al. |
| 9,244,197 B2 | 1/2016 | Alli et al. |
| 9,260,544 B2 | 2/2016 | Rathore et al. |
| 9,297,928 B2 | 3/2016 | Molock et al. |
| 9,297,929 B2 | 3/2016 | Scales et al. |
| 9,927,635 B2 | 3/2018 | Ishak et al. |
| 2010/0048847 A1 | 2/2010 | Broad |
| 2017/0242274 A1 | 8/2017 | Holland et al. |
| 2018/0037690 A1 | 2/2018 | Aitken et al. |

FOREIGN PATENT DOCUMENTS

| | | |
|---|---|---|
| RU | 2196557 C2 | 1/2003 |
| RU | 2197907 C2 | 2/2003 |
| RU | 2294132 C2 | 10/2006 |
| RU | 2540655 C2 | 9/2014 |
| SU | 374816 A3 | 3/1973 |
| WO | 2001030866 A1 | 5/2001 |
| WO | 2003022321 A2 | 3/2003 |
| WO | 2003089519 A1 | 10/2003 |
| WO | 2008061992 A2 | 5/2008 |
| WO | 2008109624 A2 | 9/2008 |

OTHER PUBLICATIONS

Compendium of Polymer Terminology and Nomenclature: IUPAC Recommendations 2008, edited by: Richard G. Jones, Jaroslav Kahovec, Robert Stepto, Edward S. Wilks, Michael Hess, Tatsuki Kitayama, and W. Val Metanomski.

(56) References Cited

OTHER PUBLICATIONS

Crivello, et al, Photoinitiators for Free Radical Cationic & Anionic Photopolymerisation, 2nd Edition, vol. III, pp. 275-298, John Wiley and Sons, New York, 1998.
Doutch et al, Ultraviolet Light Transmission through the Human Corneal Stroma Is Reduced in the Periphery, Biophysical Journal, vol. 102, Mar. 2012, pp. 1258-1264.
Ham et al., "Retinal sensitivity to damage from short wavelength light." Nature, vol. 260 (1976), pp. 153-155.
Leonard et al, Cinnolines. I. Synthesis of Aminoacetophenones and Aminopropiophenones, J. Org. Chem., 1946, vol. 11, pp. 405-418.
PCT International Preliminary Report on Patentability, dated Dec. 29, 2020, for PCT Int'l Appln. No. PCT/IB2019/054246.
PCT International Search Report, dated Sep. 6, 2019, for PCT Int'l Appln. No. PCT/IB2019/054246.
Truscott et al, A new UV-filter compound in human lenses, FEBS Letters, vol. 348 (1994) pp. 173-176.
Tsuji et al, Studies on Antiinflammatory Agents. I. Synthesis and Pharmacological Properties of 2'-Phenoxymethanesulfonanilide Derivatives, 1992, vol. 40, Issue 9, pp. 2399-2409.
Wang et al, Direct Exchange of a Ketone Methyl or Aryl Group to Another Aryl Group through C—C Bond Activation Assisted by Rhodium Chelation, Angewandte Chemie, 2012, vol. 51, Issue 49), pp. 12334-12338.
You et al, Synthesis and antitumor activity of novel 10-amino acids ester homocamptothecin analogues, Chinese Chemical Letters, 2008, vol. 19, Issue 7, pp. 811-819.
Bondyreva E. Y., "Polimerization", Methodological Guidelines for Independent Work. Nizhnekamsk Chemical and Technological Institute of the Federal State Budget Educational Institution of Higher Professional Education "Kazan National Research Technological University", Nizhnekamsk, 2014, pp. 4-13.
Sutjagin et al, "Chemistry and Physics of Polymers," Training Manual. TPU Publishing House, Tomsk, 2003, Chapter 1, p. 9, Chapter 2, pp. 19-56.
"Statement on Ocular Ultraviolet Radiation Hazards in Sunlight", In American Optometric Association, Nov. 10, 1993, 3 Pages.
Babu, et al, The facile flow-injection spectrophotometric detection of gold(III) in water and phyarmaceutical samples using 3,5-dimethoxy-4-hydroxy-2-aminoacetophenone isonicotinoy hydrazone (3,5-DMHAAINH), Journal of Hazardous Materials, 2005, pp. 213-218, B120.
Bandurco et al, Synthesis and Cardiotonic Activity of a Series of Substituted 4-Alkyl-2(1H)-quinazolinones, Journal of Medicinal Chemistry, 1987, pp. 1421-1426 (6 pages), vol. 30, No. 8.

\* cited by examiner

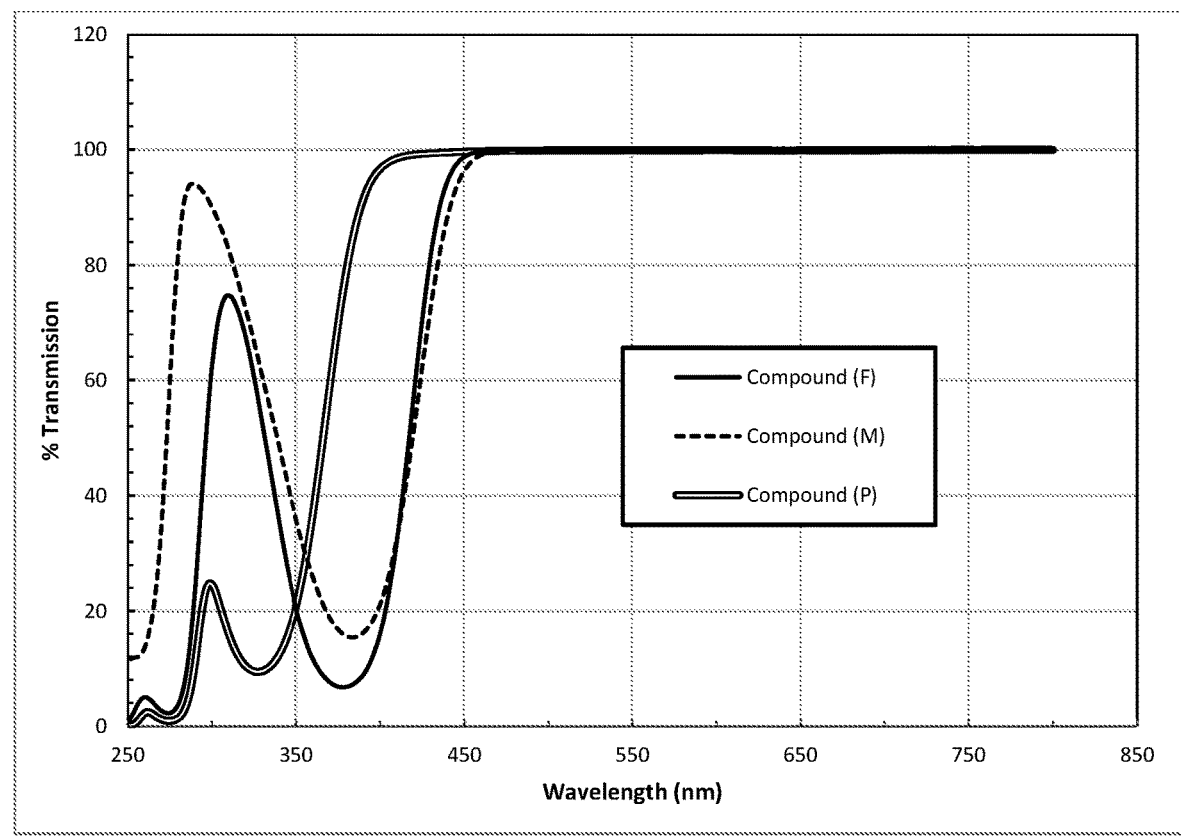
FIG. 1 – UV-VIS Transmission Spectra of 0.2 mM methanol solutions of Compounds (F), (M), and (P)

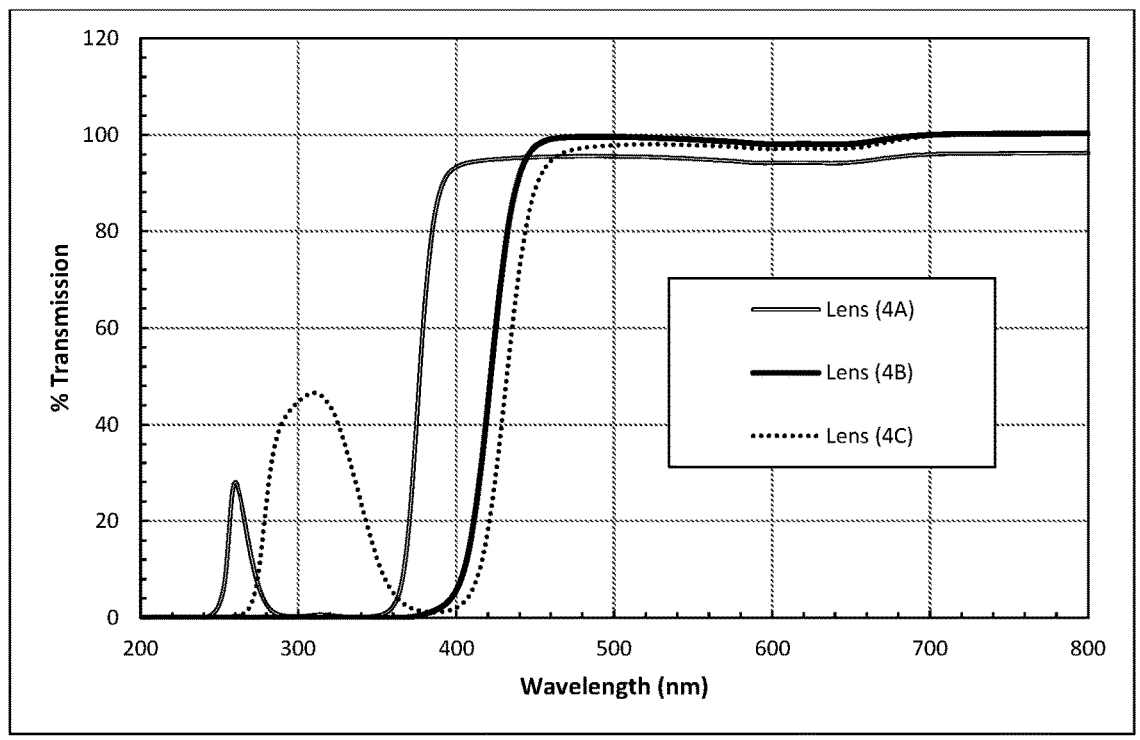
FIG. 2 – UV-VIS Transmission Spectra of Silicone Hydrogel Contact Lenses comprising Compounds (F) and (M)

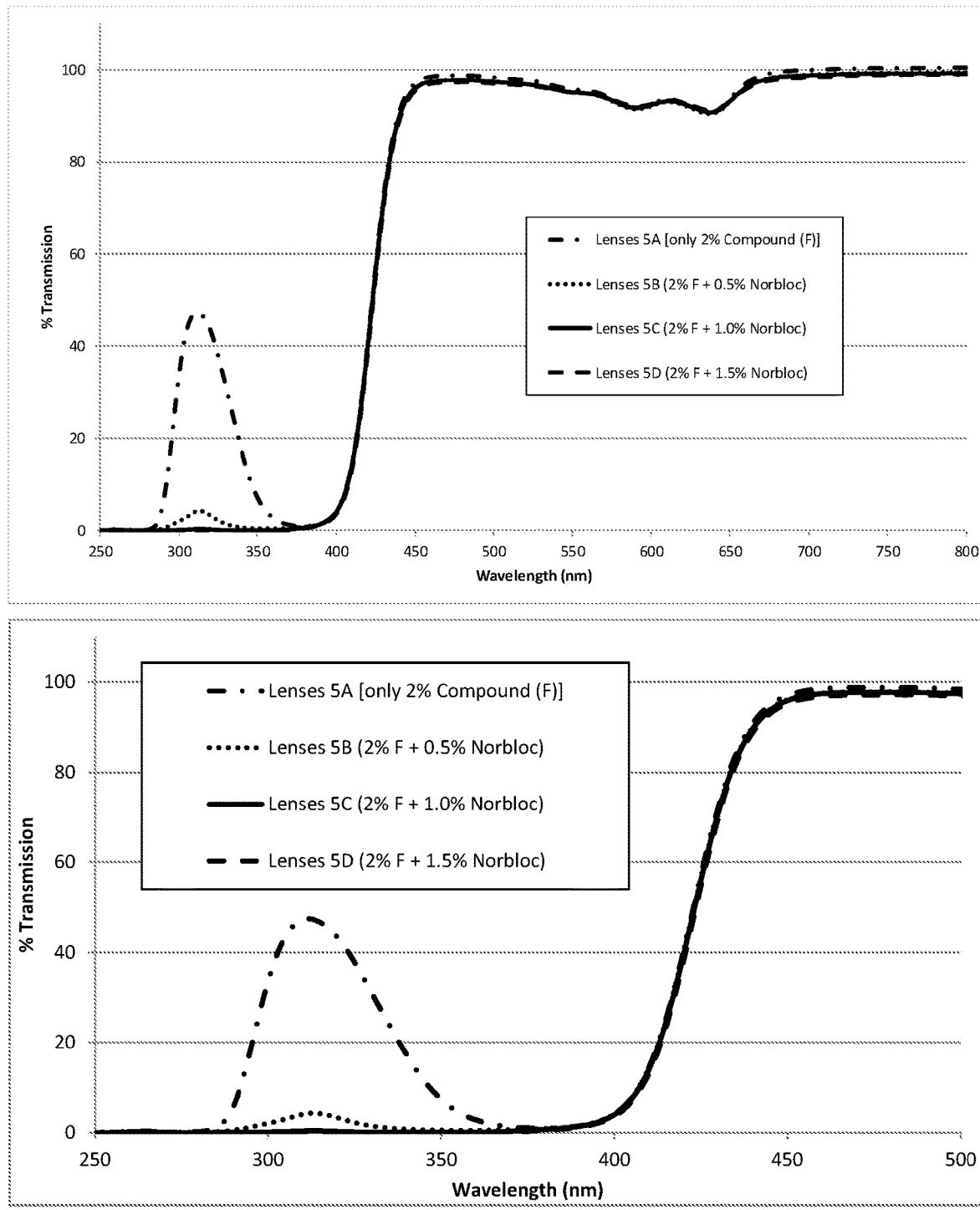
FIG. 3 – UV-VIS Transmission Spectra of Silicone Hydrogel Contact Lenses comprising 2 weight percent of Compound (F) and different levels of Norbloc®

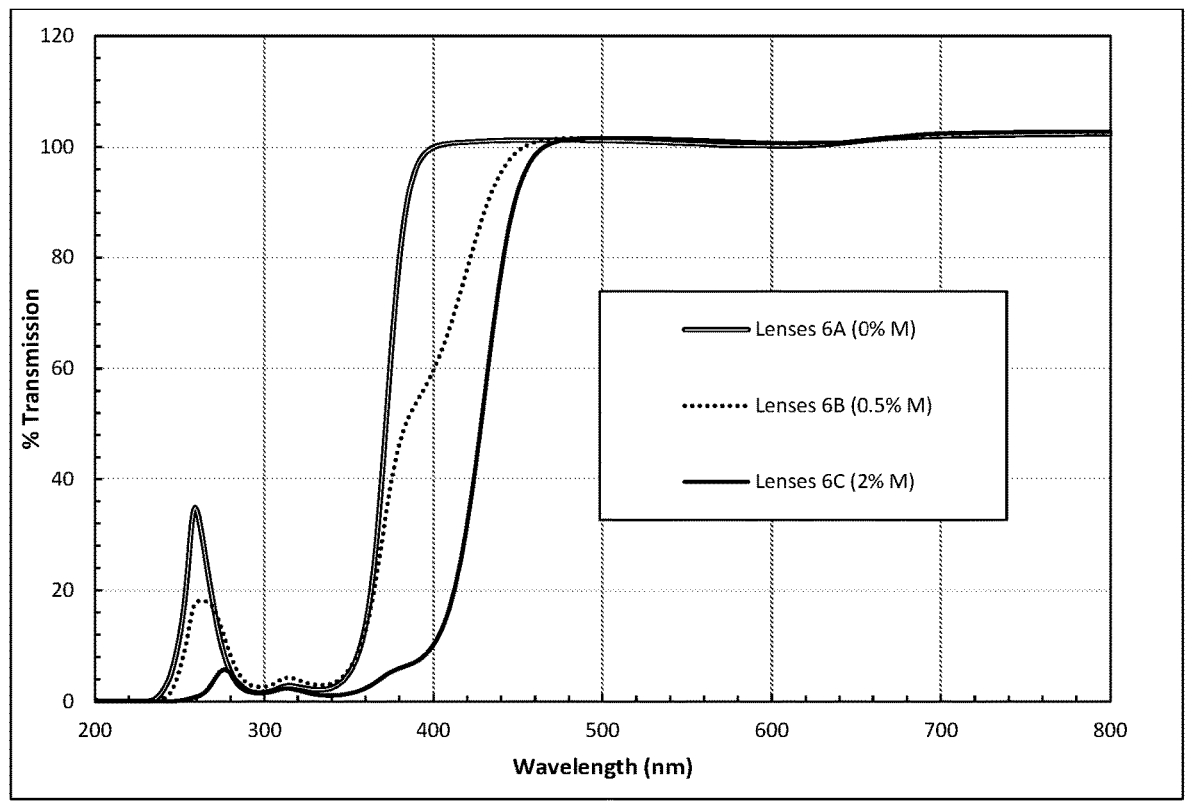
FIG. 4 – UV-VIS Transmission Spectra of Conventional Hydrogel Contact Lenses comprising Compound (M)

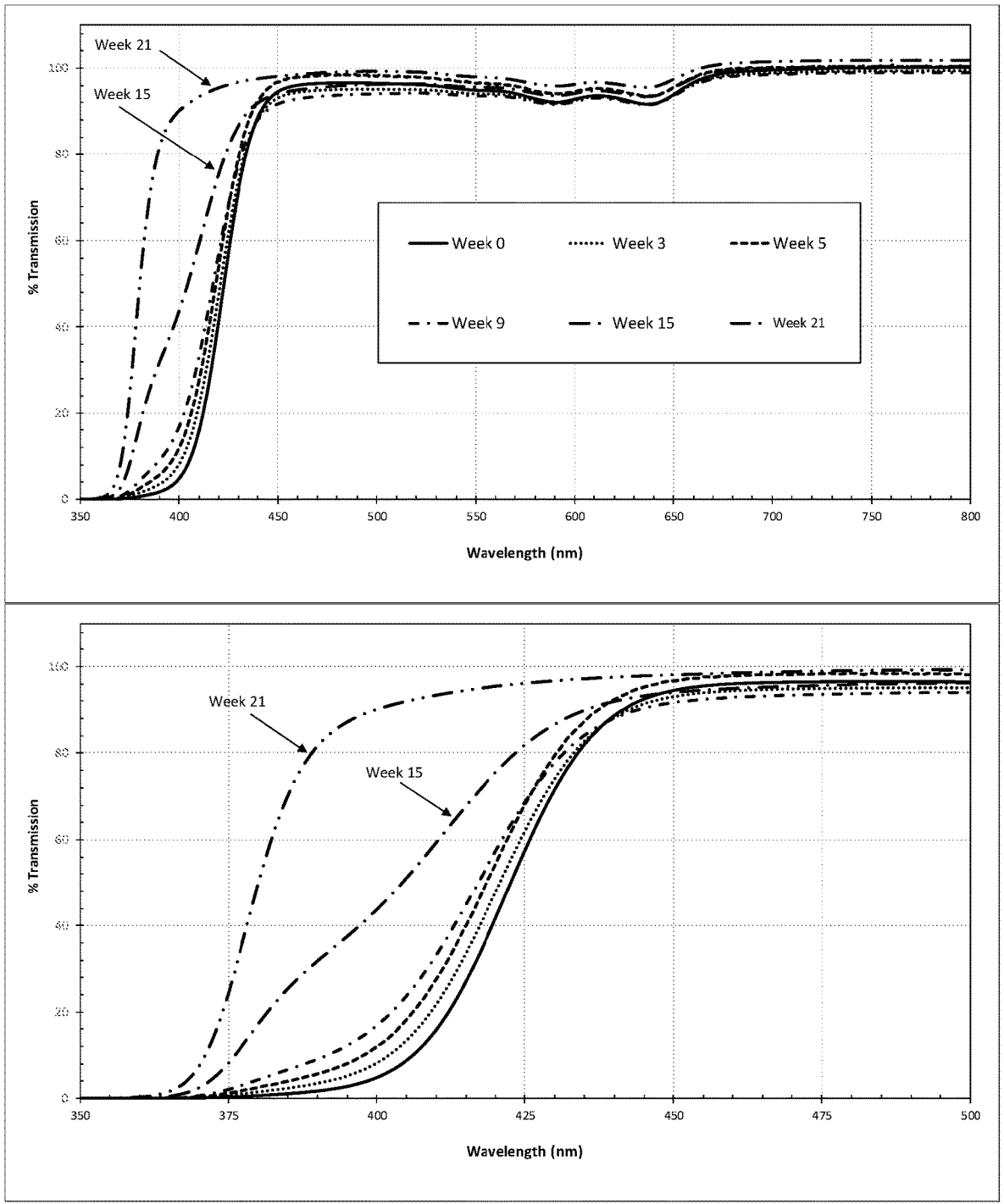
FIG. 5 – UV-VIS Transmission Spectra of Silicone Hydrogel Contact Lenses (7A) comprising Compound (F) after exposure to direct sunlight

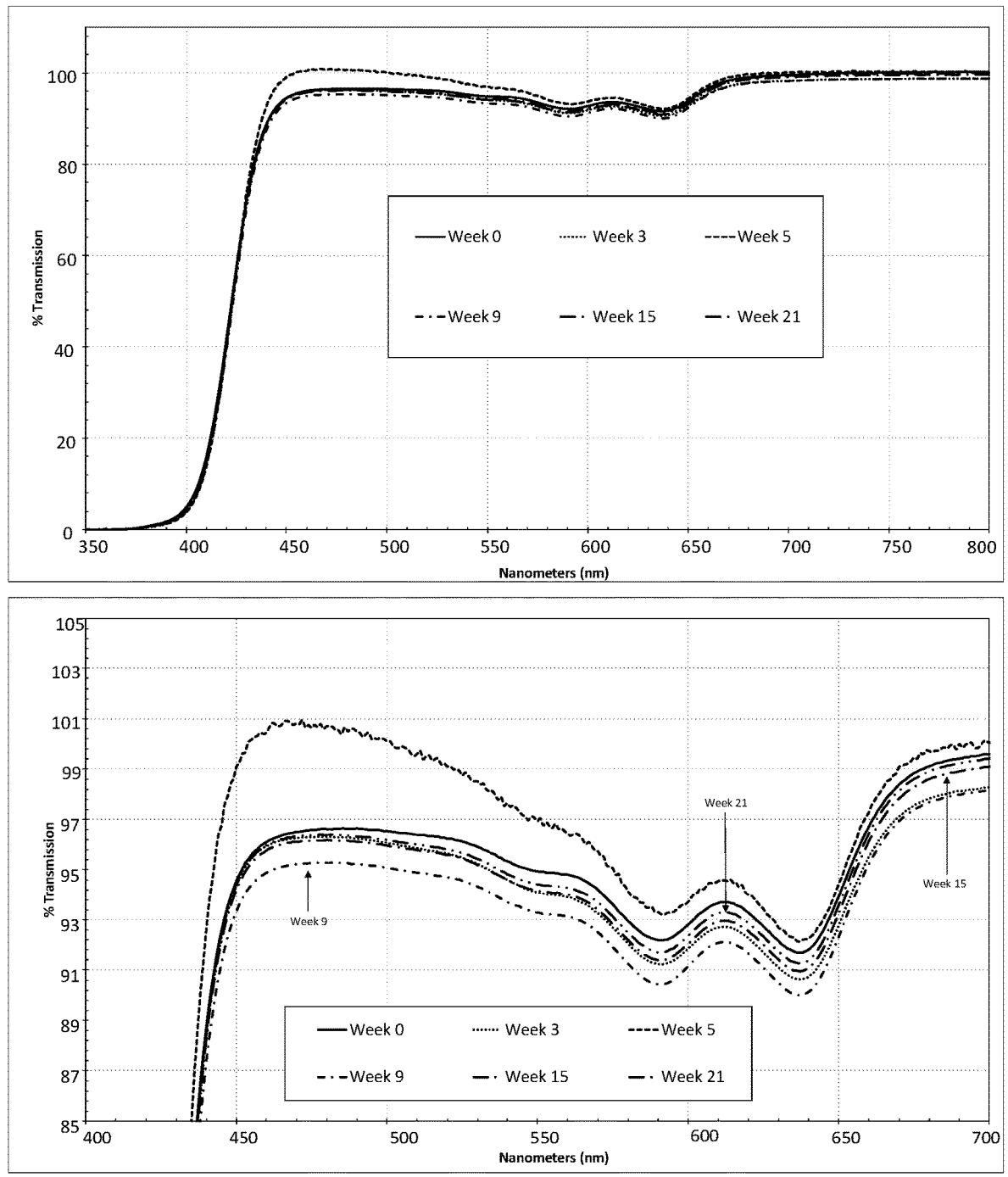
FIG. 6 – UV-VIS Transmission Spectra of Silicone Hydrogel Contact Lenses (7B) comprising Compound (F) after exposure to indoor lighting

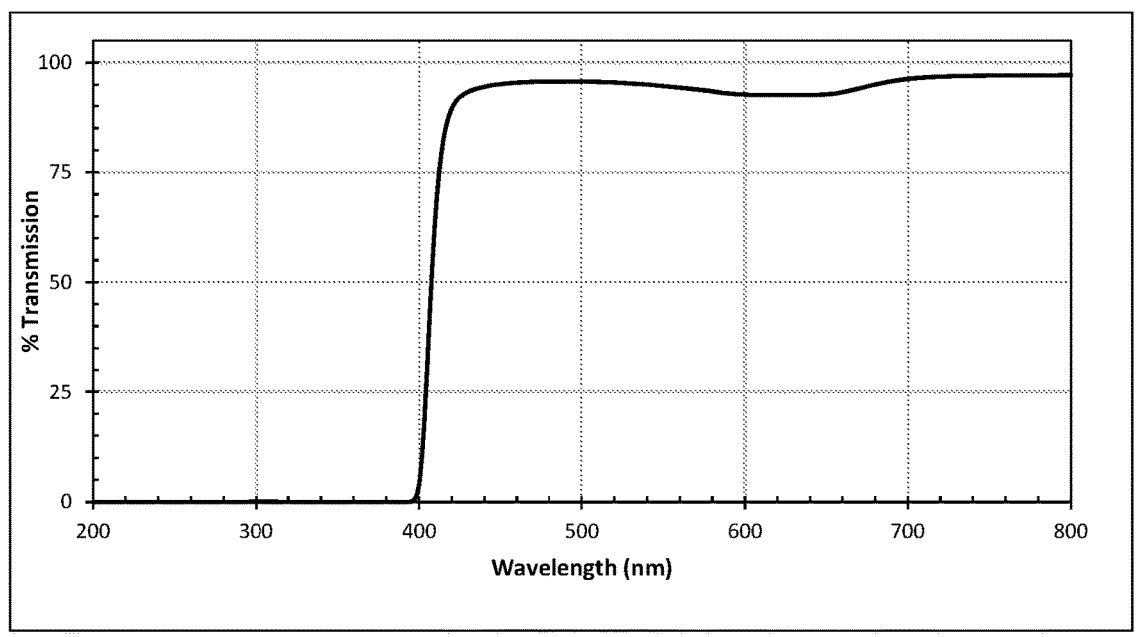
FIG. 7 - UV-VIS Transmission Spectra of a Silicone Hydrogel Contact Lens containing 2 weight percent of Compound (N) (Example 12)

POLYMERIZABLE ABSORBERS OF UV AND HIGH ENERGY VISIBLE LIGHT

RELATED APPLICATIONS

This application is a divisional of U.S. patent application Ser. No. 16/398,722, filed Apr. 30, 2019, now U.S. Pat. No. 11,046,636, which claims priority to U.S. Provisional Patent Application Ser. No. 62/691,666, filed Jun. 29, 2018, which is incorporated herein by reference in its entirety.

FIELD OF THE INVENTION

The invention relates to UV and high energy visible light absorbers. More particularly, the invention relates to compounds with polymerizable functionality that absorb various wavelengths of UV and/or high energy visible light, and yet are visibly transparent when incorporated in an article. Thus, the compounds may be used in polymeric articles, including biomedical devices, such as ophthalmic devices.

BACKGROUND OF THE INVENTION

High energy radiation from the sun, such as UV and high-energy visible light, is known to be responsible for cellular damage. While most of the radiation below 280 nm in wavelength is absorbed by the earth's atmosphere, photons possessing wavelengths ranging between 280 and 400 nm have been associated with several ocular disorders including corneal degenerative changes, and age-related cataract and macular degeneration. (See Statement on Ocular Ultraviolet Radiation Hazards in Sunlight, American Optometric Association, Nov. 10, 1993). The human cornea absorbs some radiation up to 320 nm in wavelength (30% transmission) (Doutch, J. J., Quantock, A. J., Joyce, N.C., Meek, K. M, *Biophys. J.*, 2012, 102, 1258-1264), but is inefficient in protecting the back of the eye from radiation ranging from 320 to 400 nm in wavelength.

Contact lens standards define the upper UV radiation wavelength at 380 nm. The current Class I UV absorbing criteria defined by the American Optometric Association require >99% of the radiation between 280 and 315 nm (UV B) and >90% of the 316 to 380 nm (UV A) radiation to be absorbed by the contact lens. While the criteria effectively address protection of the cornea (<1% UV B transmittance), there is little attention paid to the lower energy UV radiation (>380<400 nm) associated with retinal damage (Ham, W. T, Mueller, H. A., Sliney, D. H. *Nature* 1976; 260(5547):153-5) or to high energy visible radiation.

High energy-visible light may also cause visual discomfort or circadian rhythm disruption. For example, computer and electronic device screens, flat screen televisions, energy efficient lights, and LED lights are known to generate high energy visible light. Prolonged exposure to such sources may cause eye strain. Viewing high energy visible light emitting devices at night is also postulated to disrupt the natural circadian rhythm leading, for example, to inadequate sleep.

Absorption of high energy light before it reaches the eye continues to be a desirable goal in the ophthalmics field. However, the extent to which a particular wavelength range is absorbed is also important. For instance, in the UV A and UV B ranges, it may be desirable to absorb as much radiation as possible. On the other hand, since high energy visible light forms a part of the visible spectrum, complete absorption of such light may negatively affect vision. With high energy visible light, therefore, partial absorption may be more desirable.

There is a need for materials that provide targeted absorption of undesirable wavelengths of high energy radiation, and that are processable into functional products. Compounds that absorb or attenuate high energy radiation, when used in ophthalmic devices, can help protect the cornea, as well as the interior cells in the ocular environment, from degradation, strain, and/or circadian rhythm disruption.

SUMMARY OF THE INVENTION

The invention relates to high energy light absorbing compounds that absorb UV and/or high energy visible (HEV) light while substantially transmitting (e.g., greater than 80% transmission) at wavelengths longer than about 450 nm. The compounds are therefore effective at providing targeted absorption of high energy light, such as UV (UVA and UVB), low energy UV light (385 nm to 400 nm), and/or HEV (e.g., 400 to 450 nm).

The compounds are also polymerizable and are generally compatible with other raw materials, as well as the polymerization and processing conditions, that are used for making ophthalmic devices such as soft contact lenses. The compounds can therefore be readily covalently incorporated into the final product without the need for significant modification of existing manufacturing processes and equipment.

Accordingly, in one aspect the invention provides a compound of formula I:

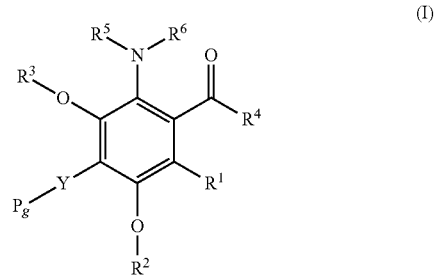

(I)

wherein Y is a linking group; $P_g$ is a polymerizable group; le is H or $C_1$-$C_6$ alkyl; $R^2$ and $R^3$ are independently $C_1$-$C_6$ alkyl or cycloalkyl; $R^4$ is $C_1$-$C_6$ alkyl; and $R^5$ and $R^6$ are independently H or $C_1$-$C_6$ alkyl.

In another aspect, the invention provides an ophthalmic device that is a free radical reaction product of a reactive mixture comprising: one or more monomers suitable for making the ophthalmic device; and a polymerizable high energy light absorbing compound comprising a compound of formula I as described herein.

In a further aspect, the invention provides a method for making an ophthalmic device. The method comprises: (a) providing a reactive mixture containing a compound of formula I as described herein, one or more device forming monomers, and a radical initiator; and (b) polymerizing the reactive mixture to form the ophthalmic device.

BRIEF DESCRIPTION OF THE FIGURES

FIG. 1 shows UV-VIS Transmission Spectra of 0.2 mM methanol solutions of Compounds (F), (M), and (P).

FIG. 2 shows UV-VIS Transmission Spectra of Silicone Hydrogel Contact Lenses comprising Compounds (F) and (M).

FIG. 3 shows UV-VIS Transmission Spectra of Silicone Hydrogel Contact Lenses comprising 2 weight percent of Compound (F) and different levels of Norbloc®.

FIG. 4 shows UV-VIS Transmission Spectra of Conventional Hydrogel Contact Lenses comprising Compound (M).

FIG. 5 shows UV-VIS Transmission Spectra of Silicone Hydrogel Contact Lenses (7A) comprising Compound (F) after exposure to direct sunlight.

FIG. 6 shows UV-VIS Transmission Spectra of Silicone Hydrogel Contact Lenses (7B) comprising Compound (F) after exposure to indoor lighting.

FIG. 7 shows UV-VIS Transmission Spectra of a Silicone Hydrogel Contact Lens containing 2 weight percent of Compound (N) (Example 12).

DETAILED DESCRIPTION OF THE INVENTION

It is to be understood that the invention is not limited to the details of construction or process steps set forth in the following description. The invention is capable of other embodiments and of being practiced or being carried out in various ways using the teaching herein.

As noted above, in one aspect, the invention provides UV/HEV absorbing compounds. The compounds contain polymerizable functionality. It has been discovered that ophthalmic devices that absorb substantial amounts of UV light as well as some amounts of HEV light can be readily prepared as described herein.

It has also been discovered that compounds of formula I are substantially photostable when exposed to indoor lighting, meaning that the compounds, when incorporated in an ophthalmic device, do not undergo significant degradation over time. Such photostability can be determined by measuring the UV/Vis transmission spectrum of the ophthalmic device over a test period, such as 21 weeks. Significant changes in the spectrum over the test period are indicative of a lack of photostability. By way of example, ophthalmic devices (such as contact lenses) incorporating compounds of the invention, when exposed to indoor office lighting over a 21 week period at room temperature, exhibit 5% or less, preferable 2% or less, or more preferably 0.5% or less change in their average transmission over a wavelength range of 380 to 700 nm. By way of further example, ophthalmic devices (such as contact lenses) containing compounds of the invention, when exposed to indoor office lighting over a 21 week period at room temperature, exhibit 5% or less, preferable 3% or less, more preferably 2% or less, even more preferably 1% or less of change in their average transmission over a wavelength range of 400 to 500 nm. Such change may be calculated as the absolute value of the difference between the average transmission (over the 380-700 nm range) at time 21 weeks and at time zero.

Thus, compounds of the invention may successfully absorb UV (UVA, UVB), and/or HEV, while transmitting in the visible spectrum. The compounds are polymerizable and are also substantially photostable. The compounds therefore are suitable for incorporation in a variety of products, including biomedical devices and ophthalmic devices.

With respect to the terms used in this disclosure, the following definitions are provided.

Unless defined otherwise, all technical and scientific terms used herein have the same meaning as commonly understood by one of ordinary skill in the art to which the invention belongs. The polymer definitions are consistent with those disclosed in the Compendium of Polymer Terminology and Nomenclature, IUPAC Recommendations 2008, edited by: Richard G. Jones, Jaroslav Kahovec, Robert Stepto, Edward S. Wilks, Michael Hess, Tatsuki Kitayama, and W. Val Metanomski. All publications, patent applications, patents, and other references mentioned herein are incorporated by reference.

As used herein, the term "(meth)" designates optional methyl substitution. Thus, a term such as "(meth)acrylates" denotes both methacrylates and acrylates.

Wherever chemical structures are given, it should be appreciated that alternatives disclosed for the substituents on the structure may be combined in any combination. Thus, if a structure contained substituents R* and R**, each of which contained three lists of potential groups, 9 combinations are disclosed. The same applies for combinations of properties.

When a subscript, such as "n" in the generic formula $[***]_n$, is used to depict the number of repeating units in a polymer's chemical formula, the formula should be interpreted to represent the number average molecular weight of the macromolecule.

The term "individual" includes humans and vertebrates.

The term "biomedical device" refers to any article that is designed to be used while either in or on mammalian tissues or fluids, and preferably in or on human tissue or fluids. Examples of these devices include but are not limited to wound dressings, sealants, tissue fillers, drug delivery systems, coatings, adhesion prevention barriers, catheters, implants, stents, and ophthalmic devices such as intraocular lenses and contact lenses. The biomedical devices may be ophthalmic devices, particularly contact lenses, most particularly contact lenses made from silicone hydrogels or conventional hydrogels.

The term "ocular surface" includes the surface and glandular epithelia of the cornea, conjunctiva, lacrimal gland, accessory lacrimal glands, nasolacrimal duct and meibomian gland, and their apical and basal matrices, puncta and adjacent or related structures, including eyelids linked as a functional system by both continuity of epithelia, by innervation, and the endocrine and immune systems.

The term "ophthalmic device" refers to any device which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Examples of ophthalmic devices include but are not limited to lenses, optical and ocular inserts, including but not limited to punctal plugs, and the like. "Lenses" include soft contact lenses, hard contact lenses, hybrid contact lenses, intraocular lenses, and overlay lenses. The ophthalmic device may comprise a contact lens.

The term "contact lens" refers to an ophthalmic device that can be placed on the cornea of an individual's eye. The contact lens may provide corrective, cosmetic, or therapeutic benefit, including wound healing, the delivery of drugs or nutraceuticals, diagnostic evaluation or monitoring, ultraviolet light absorbing, visible light or glare reduction, or any combination thereof. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

The biomedical devices, ophthalmic devices, and lenses of the present invention may be comprised of silicone hydrogels or conventional hydrogels. Silicone hydrogels typically contain at least one hydrophilic monomer and at least one silicone-containing component that are covalently bound to one another in the cured device.

"Target macromolecule" means the macromolecule being synthesized from the reactive monomer mixture comprising monomers, macromers, prepolymers, cross-linkers, initiators, additives, diluents, and the like.

The term "polymerizable compound" means a compound containing one or more polymerizable groups. The term encompasses, for instance, monomers, macromers, oligomers, prepolymers, cross-linkers, and the like.

"Polymerizable groups" are groups that can undergo chain growth polymerization, such as free radical and/or cationic polymerization, for example a carbon-carbon double bond which can polymerize when subjected to radical polymerization initiation conditions. Non-limiting examples of free radical polymerizable groups include (meth)acrylates, styrenes, vinyl ethers, (meth)acrylamides, N-vinyllactams, N-vinylamides, O-vinylcarbamates, O-vinylcarbonates, and other vinyl groups. Preferably, the free radical polymerizable groups comprise (meth)acrylate, (meth)acrylamide, N-vinyl lactam, N-vinylamide, and styryl functional groups, and mixtures of any of the foregoing. More preferably, the free radical polymerizable groups comprise (meth)acrylates, (meth)acrylamides, and mixtures thereof. The polymerizable group may be unsubstituted or substituted. For instance, the nitrogen atom in (meth)acrylamide may be bonded to a hydrogen, or the hydrogen may be replaced with alkyl or cycloalkyl (which themselves may be further substituted).

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

A "monomer" is a mono-functional molecule which can undergo chain growth polymerization, and in particular, free radical polymerization, thereby creating a repeating unit in the chemical structure of the target macromolecule. Some monomers have di-functional impurities that can act as cross-linking agents. A "hydrophilic monomer" is also a monomer which yields a clear single phase solution when mixed with deionized water at 25° C. at a concentration of 5 weight percent. A "hydrophilic component" is a monomer, macromer, prepolymer, initiator, cross-linker, additive, or polymer which yields a clear single phase solution when mixed with deionized water at 25° C. at a concentration of 5 weight percent. A "hydrophobic component" is a monomer, macromer, prepolymer, initiator, cross-linker, additive, or polymer which is slightly soluble or insoluble in deionized water at 25° C.

A "macromolecule" is an organic compound having a number average molecular weight of greater than 1500, and may be reactive or non-reactive.

A "macromonomer" or "macromer" is a macromolecule that has one group that can undergo chain growth polymerization, and in particular, free radical polymerization, thereby creating a repeating unit in the chemical structure of the target macromolecule. Typically, the chemical structure of the macromer is different than the chemical structure of the target macromolecule, that is, the repeating unit of the macromer's pendent group is different than the repeating unit of the target macromolecule or its mainchain. The difference between a monomer and a macromer is merely one of chemical structure, molecular weight, and molecular weight distribution of the pendent group. As a result, and as used herein, the patent literature occasionally defines monomers as polymerizable compounds having relatively low molecular weights of about 1,500 Daltons or less, which inherently includes some macromers. In particular, monomethacryloxypropyl terminated mono-n-butyl terminated polydimethylsiloxane (molecular weight=500-1500 g/mol) (mPDMS) and mono-(2-hydroxy-3-methacryloxypropyl)-propyl ether terminated mono-n-butyl terminated polydimethylsiloxane (molecular weight=500-1500 g/mol) (OH-mPDMS) may be referred to as monomers or macromers. Furthermore, the patent literature occasionally defines macromers as having one or more polymerizable groups, essentially broadening the common definition of macromer to include prepolymers. As a result and as used herein, di-functional and multi-functional macromers, prepolymers, and crosslinkers may be used interchangeably.

A "silicone-containing component" is a monomer, macromer, prepolymer, cross-linker, initiator, additive, or polymer in the reactive mixture with at least one silicon-oxygen bond, typically in the form of siloxy groups, siloxane groups, carbosiloxane groups, and mixtures thereof.

Examples of silicone-containing components which are useful in this invention may be found in U.S. Pat. Nos. 3,808,178, 4,120,570, 4,136,250, 4,153,641, 4,740,533, 5,034,461, 5,070,215, 5,244,981, 5,314,960, 5,331,067, 5,371,147, 5,760,100, 5,849,811, 5,962,548, 5,965,631, 5,998,498, 6,367,929, 6,822,016, 6,943,203, 6,951,894, 7,052,131, 7,247,692, 7,396,890, 7,461,937, 7,468,398, 7,538,146, 7,553,880, 7,572,841, 7,666,921, 7,691,916, 7,786,185, 7,825,170, 7,915,323, 7,994,356, 8,022,158, 8,163,206, 8,273,802, 8,399,538, 8,415,404, 8,420,711, 8,450,387, 8,487,058, 8,568,626, 8,937,110, 8,937,111, 8,940,812, 8,980,972, 9,056,878, 9,125,808, 9,140,825, 9,156,934, 9,170,349, 9,217,813, 9,244,196, 9,244,197, 9,260,544, 9,297,928, 9,297,929, and European Patent No. 080539. These patents are hereby incorporated by reference in their entireties.

A "polymer" is a target macromolecule composed of the repeating units of the monomers used during polymerization.

A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into radicals which can subsequently react with a monomer to initiate a free radical polymerization reaction. A thermal initiator decomposes at a certain rate depending on the temperature; typical examples are azo compounds such as 1,1'-azobisisobutyronitrile and 4,4'-aobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "cross-linking agent" is a di-functional or multi-functional monomer or macromer which can undergo free radical polymerization at two or more locations on the molecule, thereby creating branch points and a polymeric network. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers which contains remaining polymerizable groups capable of undergoing further reaction to form a polymer.

A "polymeric network" is a cross-linked macromolecule that can swell but cannot dissolve in solvents. "Hydrogels" are polymeric networks that swell in water or aqueous solutions, typically absorbing at least 10 weight percent water. "Silicone hydrogels" are hydrogels that are made from at least one silicone-containing component with at least one hydrophilic component. Hydrophilic components may also include non-reactive polymers.

"Conventional hydrogels" refer to polymeric networks made from components without any siloxy, siloxane or carbosiloxane groups. Conventional hydrogels are prepared from reactive mixtures comprising hydrophilic monomers. Examples include 2-hydroxyethyl methacrylate ("HEMA"), N-vinyl pyrrolidone ("NVP"), N, N-dimethylacrylamide ("DMA") or vinyl acetate. U.S. Pat. Nos. 4,436,887, 4,495,313, 4,889,664, 5,006,622, 5,039459, 5,236,969, 5,270,418, 5,298,533, 5,824,719, 6,420,453, 6,423,761, 6,767,979, 7,934,830, 8,138,290, and 8,389,597 disclose the formation of conventional hydrogels. Commercially available conventional hydrogels include, but are not limited to, etafilcon, genfilcon, hilafilcon, lenefilcon, nesofilcon, omafilcon, polymacon, and vifilcon, including all of their variants.

"Silicone hydrogels" refer to polymeric networks made from at least one hydrophilic component and at least one silicone-containing component. Examples of silicone hydrogels include acquafilcon, asmofilcon, balafilcon, comfilcon, delefilcon, enfilcon, fanfilcon, formofilcon, galyfilcon, lotrafilcon, narafilcon, riofilcon, samfilcon, senofilcon, somofilcon, and stenfilcon, including all of their variants, as well as silicone hydrogels as prepared in U.S. Pat. Nos. 4,659,782, 4,659,783, 5,244,981, 5,314,960, 5,331,067, 5,371,147, 5,998,498, 6,087,415, 5,760,100, 5,776,999, 5,789,461, 5,849,811, 5,965,631, 6,367,929, 6,822,016, 6,867,245, 6,943,203, 7,247,692, 7,249,848, 7,553,880, 7,666,921, 7,786,185, 7,956,131, 8,022,158, 8,273,802, 8,399,538, 8,470,906, 8,450,387, 8,487,058, 8,507,577, 8,637,621, 8,703,891, 8,937,110, 8,937,111, 8,940,812, 9,056,878, 9,057,821, 9,125,808, 9,140,825, 9,156,934, 9,170,349, 9,244,196, 9,244,197, 9,260,544, 9,297,928, 9,297,929 as well as WO 03/22321, WO 2008/061992, and US 2010/0048847. These patents are hereby incorporated by reference in their entireties.

An "interpenetrating polymeric network" comprises two or more networks which are at least partially interlaced on the molecular scale but not covalently bonded to each other and which cannot be separated without braking chemical bonds. A "semi-interpenetrating polymeric network" comprises one or more networks and one or more polymers characterized by some mixing on the molecular level between at least one network and at least one polymer. A mixture of different polymers is a "polymer blend." A semi-interpenetrating network is technically a polymer blend, but in some cases, the polymers are so entangled that they cannot be readily removed.

The terms "reactive mixture" and "reactive monomer mixture" refer to the mixture of components (both reactive and non-reactive) which are mixed together and, when subjected to polymerization conditions, form the conventional or silicone hydrogels of the present invention as well as biomedical devices, ophthalmic devices, and contact lenses made therefrom. The reactive monomer mixture may comprise reactive components such as the monomers, macromers, prepolymers, cross-linkers, and initiators, additives such as wetting agents, release agents, polymers, dyes, light absorbing compounds such as UV absorbers, pigments, dyes and photochromic compounds, any of which may be reactive or non-reactive but are capable of being retained within the resulting biomedical device, as well as pharmaceutical and nutraceutical compounds, and any diluents. It will be appreciated that a wide range of additives may be added based upon the biomedical device which is made and its intended use. Concentrations of components of the reactive mixture are expressed as weight percentages of all components in the reactive mixture, excluding diluent. When diluents are used, their concentrations are expressed as weight percentages based upon the amount of all components in the reactive mixture and the diluent.

"Reactive components" are the components in the reactive mixture which become part of the chemical structure of the polymeric network of the resulting hydrogel by covalent bonding, hydrogen bonding, electrostatic interactions, the formation of interpenetrating polymeric networks, or any other means.

The term "silicone hydrogel contact lens" refers to a hydrogel contact lens that is made from at least one silicone-containing compound. Silicone hydrogel contact lenses generally have increased oxygen permeability compared to conventional hydrogels. Silicone hydrogel contact lenses use both their water and polymer content to transmit oxygen to the eye.

The term "multi-functional" refers to a component having two or more polymerizable groups. The term "mono-functional" refers to a component having one polymerizable group.

The terms "halogen" or "halo" indicate fluorine, chlorine, bromine, and iodine.

"Alkyl" refers to an optionally substituted linear or branched alkyl group containing the indicated number of carbon atoms. If no number is indicated, then alkyl (including any optional substituents on alkyl) may contain 1 to 16 carbon atoms. Preferably, the alkyl group contains 1 to 10 carbon atoms, alternatively 1 to 8 carbon atoms, alternatively 1 to 6 carbon atoms, or alternatively 1 to 4 carbon atoms. Examples of alkyl include methyl, ethyl, propyl, isopropyl, butyl, iso-, sec- and tert-butyl, pentyl, hexyl, heptyl, 3-ethylbutyl, and the like. Examples of substituents on alkyl include 1, 2, or 3 groups independently selected from hydroxy, amino, amido, oxa, carboxy, alkyl carboxy, carbonyl, alkoxy, thioalkyl, carbamate, carbonate, halogen, phenyl, benzyl, and combinations thereof. "Alkylene" means a divalent alkyl group, such as —$CH_2$—, —$CH_2CH_2$—, —$CH_2CH_2CH_2$—, —$CH_2CH(CH_3)CH_2$—, and —$CH_2CH_2CH_2CH_2$—.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, more preferably 1-4 carbons, and still more preferably 1-2 carbons. "Haloalkyl" includes perhaloalkyl groups, such as —CF₃— or —CF₂CF₃—. "Haloalkylene" means a divalent haloalkyl group, such as —CH₂CF₂—.

"Cycloalkyl" refers to an optionally substituted cyclic hydrocarbon containing the indicated number of ring carbon atoms. If no number is indicated, then cycloalkyl may contain 3 to 12 ring carbon atoms. Preferred are $C_3$-$C_8$ cycloalkyl groups, $C_3$-$C_7$ cycloalkyl, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, oxa, carbonyl, alkoxy, thioalkyl, amido, carbamate, carbonate, halo, phenyl, benzyl, and combinations thereof. "Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an optionally substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, oxa, carboxy, alkyl carboxy, carbonyl, alkoxy, thioalkyl, carbamate, carbonate, halo, phenyl, benzyl, and combinations thereof. "Arylene" means a divalent aryl group, for example 1,2-phenylene, 1,3-phenylene, or 1,4-phenylene.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings. Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Thioalkyl" means an alkyl group attached to the parent molecule through a sulfur bridge. Examples of thioalkyl groups include, for instance, methylthio, ethylthio, n-propylthio and iso-propylthio. "Aryloxy" refers to an aryl group attached to a parent molecular moiety through an oxygen bridge. Examples include phenoxy. "Cyclic alkoxy" means a cycloalkyl group attached to the parent moiety through an oxygen bridge.

"Alkylamine" refers to an alkyl group attached to the parent molecular moiety through an —NH bridge. Alkyleneamine means a divalent alkylamine group, such as —CH₂CH₂NH—.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., —[Si—O]ₙ—, where n is 2 or more). Each silicon atom in the siloxanyl group is substituted with independently selected $R^A$ groups (where $R^A$ is as defined in formula A options (b)-(i)) to complete their valence.

"Silyl" refers to a structure of formula $R_3Si$— and "siloxy" refers to a structure of formula $R_3Si$—O—, where each R in silyl or siloxy is independently selected from trimethylsiloxy, $C_1$-$C_8$ alkyl (preferably $C_1$-$C_3$ alkyl, more preferably ethyl or methyl), and $C_3$-$C_8$ cycloalkyl.

"Alkyleneoxy" refers to groups of the general formula -(alkylene-O)ₚ— or —(O-alkylene)ₚ-, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration. When alkyleneoxy forms a terminal group in a molecule, the terminal end of the alkyleneoxy may, for instance, be a hydroxy or alkoxy (e.g., HO—[CH₂CH₂O]ₚ— or CH₃O—[CH₂CH₂O]ₚ—). Examples of alkyleneoxy include polyethyleneoxy, polypropyleneoxy, polybutyleneoxy, and poly (ethyleneoxy-co-propyleneoxy).

"Oxaalkylene" refers to an alkylene group as defined above where one or more non-adjacent CH₂ groups have been substituted with an oxygen atom, such as —CH₂CH₂OCH(CH₃)CH₂—. "Thiaalkylene" refers to an alkylene group as defined above where one or more non-adjacent CH₂ groups have been substituted with a sulfur atom, such as —CH₂CH₂SCH(CH₃)CH₂—.

The term "linking group" refers to a moiety that links a polymerizable group to the parent molecule. The linking group may be any moiety that is compatible with the compound of which it is a part, and that does not undesirably interfere with the polymerization of the compound, is stable under the polymerization conditions as well as the conditions for the processing and storage of the final product. For instance, the linking group may be a bond, or it may comprise one or more alkylene, haloalkylene, amide, amine, alkyleneamine, carbamate, ester (—CO₂—), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., —OCF₂—, —OCF₂CF₂—, —OCF₂CH₂—), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, MeO-alkyleneoxy, siloxanyl, siloxy, siloxy-alkyleneoxy-, siloxy-alkylene-alkyleneoxy- (where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a further polymerizable group, such as (meth)acrylate (in addition to the polymerizable group to which the linking group is linked).

Preferred linking groups include $C_1$-$C_8$ alkylene (preferably $C_2$-$C_6$ alkylene) and $C_1$-$C_8$ oxaalkylene (preferably $C_2$-$C_6$ oxaalkylene), each of which is optionally substituted with 1 or 2 groups independently selected from hydroxyl and siloxy. Preferred linking groups also include carboxylate, amide, $C_1$-$C_8$ alkylene-carboxylate-$C_1$-$C_8$ alkylene, or $C_1$-$C_8$ alkylene-amide-$C_1$-$C_8$ alkylene.

When the linking group is comprised of combinations of moieties as described above (e.g., alkylene and cycloalkylene), the moieties may be present in any order. For instance, if in Formula E below, L is indicated as being -alkylene-cycloalkylene-, then Rg-L may be either Rg-alkylene-cycloalkylene-, or Rg-cycloalkylene-alkylene-. Notwithstanding this, the listing order represents the preferred order in which the moieties appear in the compound starting from the terminal polymerizable group (e.g., Rg or Pg) to which the linking group is attached. For example, if in Formula E, L and $L^2$ are indicated as both being alkylene-cycloalkylene, then Rg-L is preferably Rg-alkylene-cycloalkylene- and -$L^2$-Rg is preferably -cycloalkylene-alkylene-Rg.

The terms "high energy radiation absorber," "UV/HEV absorber," or "high energy light absorbing compound" refer to chemical materials that absorb various wavelengths of ultraviolet light, high energy visible light, or both. A material's ability to absorb certain wavelengths of light can be determined by measuring its UV/Vis transmission spectrum. Compounds that exhibit no absorption at a particular wavelength will exhibit substantially 100 percent transmission at that wavelength. Conversely, compounds that completely absorb at a particular wavelength will exhibit substantially 0% transmission at that wavelength. If the amount of a material's transmission is indicated as a percentage for a particular wavelength range, it is to be understood that the material exhibits the percent transmission at all wavelengths within that range.

Unless otherwise indicated, ratios, percentages, parts, and the like are by weight.

Unless otherwise indicated, numeric ranges, for instance as in "from 2 to 10," are inclusive of the numbers defining the range (e.g., 2 and 10).

As noted above, in one aspect the invention provides UV/HEV absorbing compounds of formula I:

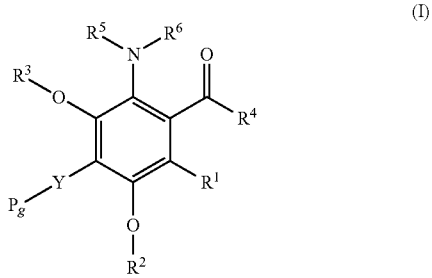

(I)

wherein:
Y is a linking group;
$P_g$ is a polymerizable group;
$R^1$ is H or $C_1$-$C_6$ alkyl;
$R^2$ and $R^3$ are independently $C_1$-$C_6$ alkyl or cycloalkyl;
$R^4$ is $C_1$-$C_6$ alkyl; and
$R^5$ and $R^6$ are independently H or $C_1$-$C_6$ alkyl.

Formula I-1. Compounds of formula I may include compounds of formula I-1, which are compounds of formula I wherein $R^1$ is H, methyl, ethyl, n-propyl, or iso-propyl. More preferably $R^1$ is H.

I-2. Preferred compounds of formulae I and I-1 include compounds of formula I-1, which are compounds of formula I or I-1 wherein $R^2$ is $C_1$-$C_6$ alkyl. Preferably $R^2$ is methyl, ethyl, n-propyl, or iso-propyl. More preferably, $R^2$ is methyl.

I-3. Preferred compounds of formulae I, I-1, and I-2 include compounds of formula I-3, which are compounds of formula I, I-1, or I-2 wherein $R^3$ is $C_1$-$C_6$ alkyl. Preferably $R^3$ is methyl, ethyl, n-propyl, or iso-propyl. More preferably, $R^3$ is methyl.

I-4. Preferred compounds of formulae I, I-1, I-2, and I-3 include compounds of formula I-4, which are compounds of formula I, I-1, I-2, or I-3 wherein $R^4$ is methyl, ethyl, n-propyl, or iso-propyl. More preferably, $R^4$ is methyl.

I-5. Preferred compounds of formulae I, I-1, I-2, I-3, and I-4 include compounds of formula I-5, which are compounds of formula I, I-1, I-2, I-3, or I-4 wherein $R^1$, $R^2$, $R^3$, and $R^4$ are the same and are $C_1$-$C_6$ alkyl. More preferably, $R^1$, $R^2$, $R^3$, and $R^4$ are each methyl, ethyl, n-propyl, or iso-propyl. Still more preferably, $R^1$, $R^2$, $R^3$, and $R^4$ are each methyl. I-6. Preferred compounds of formulae I, I-1, I-2, I-3, I-4, and I-5 include compounds of formula I-6, which are compounds of formula I, I-1, I-2, I-3, I-4, or I-5 wherein $R^5$ and $R^6$ are independently H, methyl, ethyl, n-propyl, or iso-propyl. Preferably at least one of $R^5$ and $R^6$ is H (and the other may, for instance, be H or methyl). More preferably, $R^5$ and $R^6$ are both H.

I-7. Preferred compounds of formulae I, I-1, I-2, I-3, I-4, I-5, and I-6 include compounds of formula I-7, which are compounds of formula I, I-1, I-2, I-3, I-4, I-5, or I-6 wherein $P_g$ (a polymerizable group) is styryl, vinyl carbonate, vinyl ether, vinyl carbamate, N-vinyl lactam, N-vinylamide, (meth)acrylate, or (meth)acrylamide. Preferably, $P_g$ is (meth)acrylate or (meth)acrylamide. More preferably, $P_g$ is methacrylate.

I-8. Preferred compounds of formulae I, I-1, I-2, I-3, I-4, I-5, I-6, and I-7 include compounds of formula I-8, which are compounds of formula I, I-1, I-2, I-3, I-4, I-5, I-6, or I-7 wherein Y (a linking group) is alkylene, cycloalkylene, heterocycloalkylene, arylene (e.g., phenylene), heteroarylene, oxaalkylene, thialkylene, alkyleneamine, alkylene-amide-alkylene, alkylene-amine-alkylene, or combinations of any of the foregoing groups. Preferred linking groups include $C_1$-$C_8$ alkylene (e.g., ethylene or propylene), $C_1$-$C_8$ oxaalkylene, $C_1$-$C_8$ thialkylene, $C_1$-$C_8$ alkyleneamine, $C_1$-$C_8$ alkylene-amide-$C_1$-$C_8$ alkylene, and $C_1$-$C_8$ alkylene-amine-$C_1$-$C_8$ alkylene. Particularly preferred are $C_1$-$C_8$ oxaalkylene (e.g., —$CH_2CH_2$—O—), $C_1$-$C_8$ thialkylene (e.g., —$CH_2CH_2$—S—), and $C_1$-$C_8$ alkyleneamine (e.g., —$CH_2CH_2$—N(H)— or —$CH_2CH_2$—N($CH_3$)—).

Specific examples of compounds of formula I include, but are not limited to, the compounds shown in Table 1.

TABLE 1

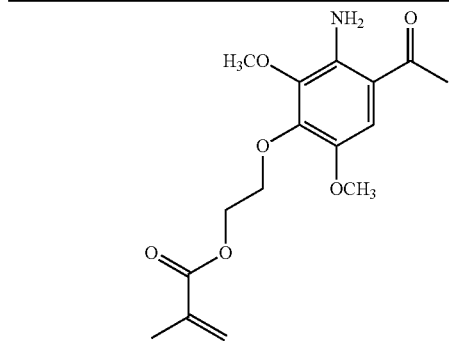

2-(4-acetyl-3-amino-2,6-dimethoxyphenoxy)ethyl methacrylate

TABLE 1-continued

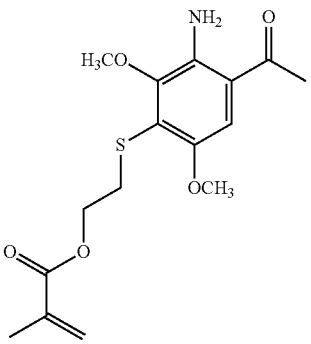 [SMILES: C=C(C)C(=O)OCCSc1c(OC)cc(C(C)=O)c(N)c1OC]

2-((4-acetyl-3-amino-2,6-dimethoxyphenyl)thio)ethyl methacrylate

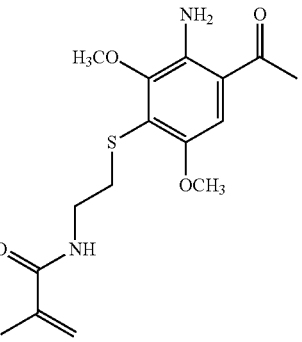

N-(2-((4-acetyl-3-amino-2,6-dimethoxyphenyl)thio)ethyl)methacrylamide

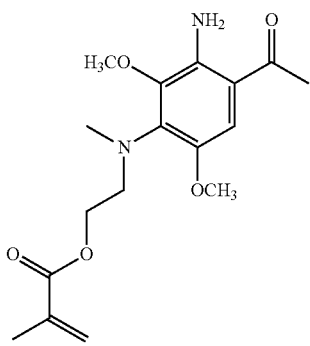 [SMILES: C=C(C)C(=O)OCCN(C)c1c(OC)cc(C(C)=O)c(N)c1OC]

2-((4-acetyl-3-amino-2,6-dimethoxyphenyl)(methyl)amino)ethyl methacrylate

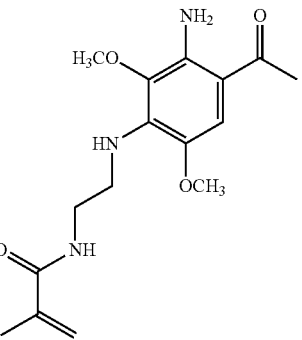

N-(2-((4-acetyl-3-amino-2,6-dimethoxyphenyl)amino)ethyl)methacrylamide

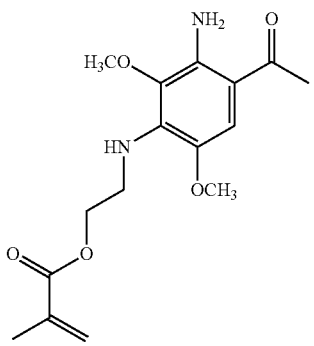 [SMILES: C=C(C)C(=O)OCCNc1c(OC)cc(C(C)=O)c(N)c1OC]

2-((4-acetyl-3-amino-2,6-dimethoxyphenyl)amino)ethyl methacrylate

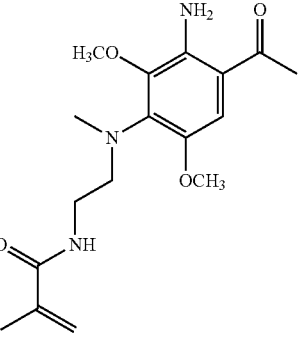

N-(2-((4-acetyl-3-amino-2,6-dimethoxyphenyl)(methyl)amino)ethyl)methacrylamide

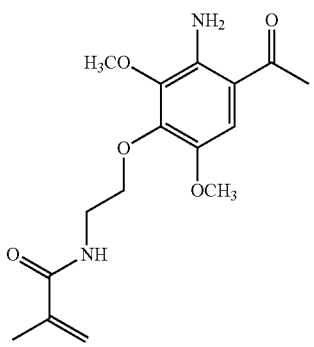 [SMILES: C=C(C)C(=O)NCCOc1c(OC)cc(C(C)=O)c(N)c1OC]

N-(2-(4-acetyl-3-amino-2,6-dimethoxyphenoxy)ethyl)methacrylamide

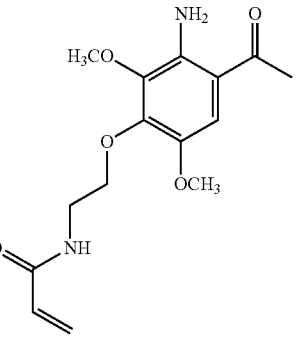

N-(2-(4-acetyl-3-amino-2,6-dimethoxyphenoxy)ethyl)acrylamide

TABLE 1-continued

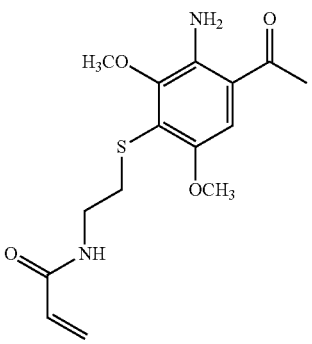 [SMILES: C=CC(=O)NCCSc1c(OC)cc(C(C)=O)c(N)c1OC]

N-(2-((4-acetyl-3-amino-2,6-dimethoxyphenyl)thio)ethyl)acrylamide

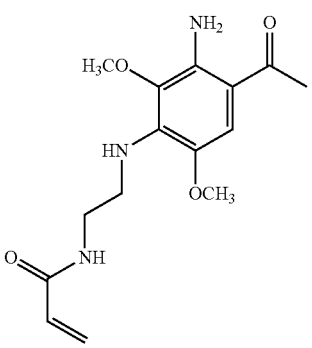 [SMILES: C=CC(=O)NCCNc1c(OC)cc(C(C)=O)c(N)c1OC]

N-(2-((4-acetyl-3-amino-2,6-dimethoxyphenyl)amino)ethyl)acrylamide

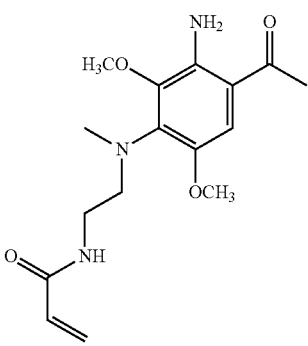 [SMILES: C=CC(=O)NCCN(C)c1c(OC)cc(C(C)=O)c(N)c1OC]

N-(2-((4-acetyl-3-amino-2,6-dimethoxyphenyl)(methyl)amino)ethyl)acrylamide

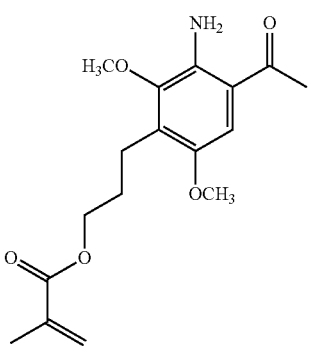 [SMILES: C=C(C)C(=O)OCCCc1c(OC)cc(C(C)=O)c(N)c1OC]

3-(4-acetyl-3-amino-2,6-dimethoxyphenyl)propyl methacrylate

TABLE 1-continued

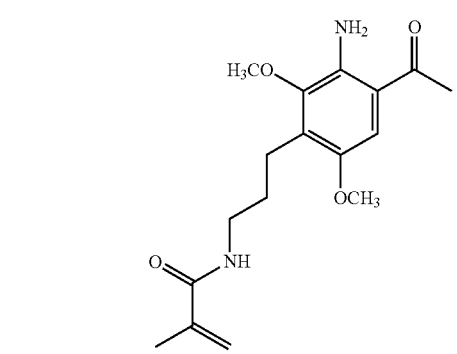 [SMILES: C=C(C)C(=O)NCCCc1c(OC)cc(C(C)=O)c(N)c1OC]

N-(3-(4-acetyl-3-amino-2,6-dimethoxyphenyl)propyl)methacrylamide

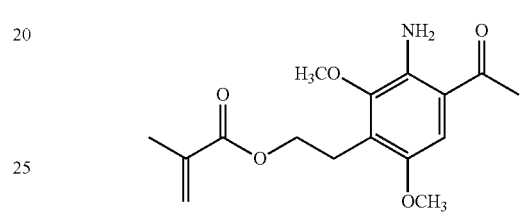

4-acetyl-3-amino-2,6-dimethoxyphenethyl methacrylate

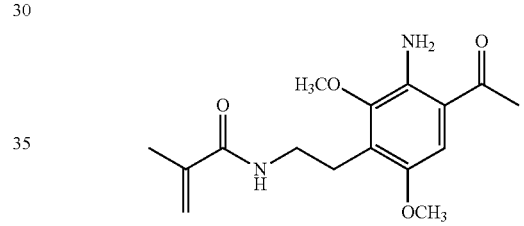

N-(4-acetyl-3-amino-2,6-dimethoxyphenethyl)methacrylamide

Compounds of formula I may be used in combination with other absorbing compounds to provide desirable absorption characteristics. For example, preferred compositions may comprise a compound of formula I and a second compound that is a UV absorbing compound. UV absorbing compounds are known in the art and fall into several classes which include, but are not limited to, benzophenones, benzotriazoles, triazines, substituted acrylonitriles, salicyclic acid derivatives, benzoic acid derivatives, cinnamic acid derivatives, chalcone derivatives, dypnone derivatives, crotonic acid derivatives, or any mixtures thereof. A preferred class of UV absorbing compound is benzotriazoles, such as Norbloc (2-(2'-hydroxy-5-methacrylyloxyethylphenyl)-2H-benzotriazole).

A particularly preferred composition comprises 2-(4-acetyl-3-amino-2,6-dimethoxyphenoxy)ethyl methacrylate and 2-(2'-hydroxy-5-methacrylyloxyethylphenyl)-2H-benzotriazole.

Compounds of formula I may be prepared as shown in the following reaction Scheme 1 and the associated description, as well as relevant literature procedures that may be used by one of skill in the art. Exemplary reagents and procedures for these reactions appear in the working examples.

Scheme 1

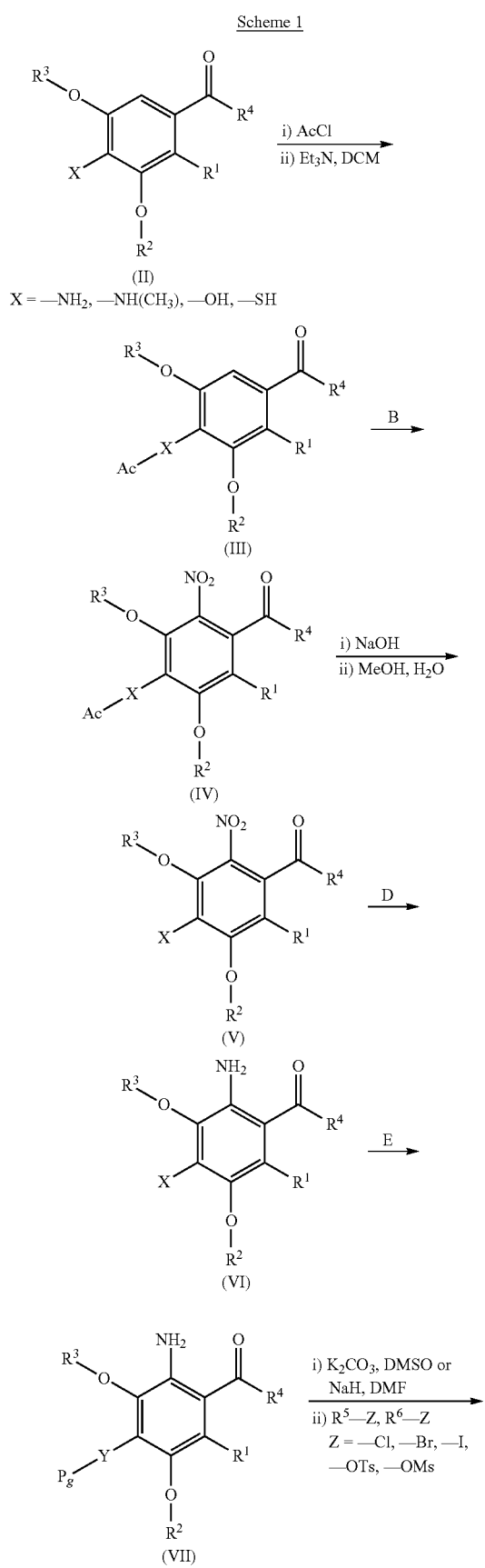

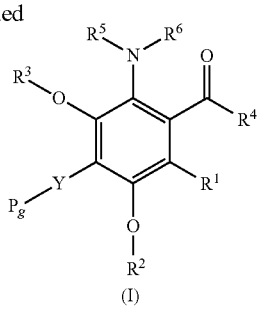

Referring to Scheme 1, the reaction of heteroatom-containing compound of formula II (X, where X=—NH$_2$, or NH(CH$_3$), or —SH, or —OH) with acetyl chloride in dichloromethane in the presence of triethylamine affords acyl protected compound of formula III. The nitration of formula III may be achieved by with Cu$_2$(NO$_3$)$_2$ in the presence of acetic anhydride (see Butenandt, A., et Al., 1957, 90, 1120-1124.), or sodium nitrate in acetic acid (Wang, J., et al., *Angewandte Chemie*, 2012, 51(49), 12334-12338.), or with fuming nitric acid (You, L., et al., *Chinese Chem. Lett.*, 2008, 19(7), 811-819.) to afford compounds of formula IV. Deprotection of the acyl protecting group of formula IV compounds may be achieved by hydrolysis employing NaOH in H$_2$O and MeOH to afford the compounds of formula V. Reduction of the nitro group in the compounds of formula V may preferably be achieved by SnCl$_2$ in ethanol, or with iron powder in the presence of an acid such as NH$_4$Cl (using the method reported by Tsuji, K., et al., *Chem. Pharm. Bull.*, 1992, 40, 2399-2409), or alternately with PtO$_2$/H$_2$ (using the method reported by Leonard, N. J., et al., *J. Org. Chem.*, 1946, 11, 405-418) to afford the compounds of formula VI. The compounds of formula VI may then be dissolved in a solvent such as dimethyl sulfoxide and reacted with 2-chloroethyl methacrylate, or 2-chloroethyl methacrylamide, or 2-chloroethyl acrylamide in the presence of potassium carbonate at 85° C. to afford compounds of formula VII. N-alkylation of formula VII to afford compounds of formula I may be achieved by known methods (see, for instance, Chuang, H., et al., *ChemMedChem*, 2011, 6, 450-456; Sokolova, M. S., et al., *Russian J. Org. Chem.*, 2008, 44, 1631-1635; Wang, J. X., et al., Chinese Chem. Lett., 2004, 15, 1161-1163). As will be recognized by those skilled in the art, the above steps may be readily modified as needed to provide the desired compounds. The compounds of formula I may be made by other procedures other than shown in Scheme 1.

High energy light absorbing compounds of formula I may be included in reactive mixtures to form various products, including biomedical devices and ophthalmic devices. Generally, the high energy light absorbing compounds can be present in any amount up to the limit of their solubility. For instance, the compounds may be present in an amount in the range of about 0.1% to about 10% by weight, or from about 0.5 to about 5% by weight, or from about 0.75% to about 4% by weight. The upper limit is typically determined by the solubility of the compound with other co-monomers and or diluents in the reactive monomer mix.

Preferably, the high energy light absorbing compounds of the invention are included in ophthalmic devices. A variety of ophthalmic devices may be prepared, including hard contact lenses, soft contact lenses, corneal onlays, corneal inlays, intraocular lenses, or overlay lenses. Preferably, the ophthalmic device is a soft contact lens, which may be made from conventional or silicone hydrogel formulations.

Ophthalmic devices of the invention comprise a free radical reaction product of a reactive mixture containing one or more compounds of formula I, one or more monomers suitable for making the desired ophthalmic device (also referred to herein as device forming monomers or hydrogel forming monomers), and optional components. Thus, the reactive mixture may, for example, include, in addition to a compounds of formula I, one or more of: hydrophilic components, hydrophobic components, silicone-containing components, wetting agents such as polyamides, crosslinking agents, and further components such as diluents and initiators.

Hydrophilic Components

Examples of suitable families of hydrophilic monomers include (meth)acrylates, styrenes, vinyl ethers, (meth)acrylamides, N-vinyl lactams, N-vinyl amides, N-vinyl imides, N-vinyl ureas, 0-vinyl carbamates, 0-vinyl carbonates, other hydrophilic vinyl compounds, and mixtures thereof.

Non-limiting examples of hydrophilic (meth)acrylate and (meth)acrylamide monomers include: acrylamide, N-isopropyl acrylamide, N,N-dimethylaminopropyl (meth)acrylamide, N,N-dimethyl acrylamide (DMA), 2-hydroxyethyl methacrylate (HEMA), 2-hydroxypropyl (meth)acrylate, 3-hydroxypropyl (meth)acrylate, 2,3-dihydroxypropyl (meth)acrylate, 2-hydroxybutyl (meth)acrylate, 3-hydroxybutyl (meth)acrylate, 4-hydroxybutyl (meth)acrylate, N-(2-hydroxyethyl) (meth)acrylamide, N,N-bis(2-hydroxyethyl) (meth)acrylamide, N-(2-hydroxypropyl) (meth)acrylamide, N,N-bis(2-hydroxypropyl) (meth)acrylamide, N-(3-hydroxypropyl) (meth)acrylamide, N-(2-hydroxybutyl) (meth)acrylamide, N-(3-hydroxybutyl) (meth)acrylamide, N-(4-hydroxybutyl) (meth)acrylamide, 2-aminoethyl (meth)acrylate, 3-aminopropyl (meth)acrylate, 2-aminopropyl (meth)acrylate, N-2-aminoethyl (meth)acrylamides), N-3-aminopropyl (meth)acrylamide, N-2-aminopropyl (meth)acrylamide, N,N-bis-2-aminoethyl (meth)acrylamides, N,N-bis-3-aminopropyl (meth)acrylamide), N,N-bis-2-aminopropyl (meth)acrylamide, glycerol methacrylate, polyethyleneglycol monomethacrylate, (meth)acrylic acid, vinyl acetate, acrylonitrile, and mixtures thereof.

Hydrophilic monomers may also be ionic, including anionic, cationic, zwitterions, betaines, and mixtures thereof. Non-limiting examples of such charged monomers include (meth)acrylic acid, N-[(ethenyloxy)carbonyl]-O-alanine (VINAL), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT), 1-propanaminium, N,N-dimethyl-N-[3-[(1-oxo-2-propen-1-yl) amino]propyl]-3-sulfo-, inner salt (SBT), 3,5-Dioxa-8-aza-4-phosphaundec-10-en-1-aminium, 4-hydroxy-N,N,N-trimethyl-9-oxo-, inner salt, 4-oxide (9CI) (PBT), 2-methacryloyloxyethyl phosphorylcholine, 3-(dimethyl(4-vinylbenzyl)ammonio)propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), and methacryloyloxy)propyl) dimethylammonio)propane-1-sulfonate (MAPDAPS).

Non-limiting examples of hydrophilic N-vinyl lactam and N-vinyl amide monomers include: N-vinyl pyrrolidone (NVP), N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, N-vinyl acetamide (NVA), N-vinyl-N-methylacetamide (VMA), N-vinyl-N-ethyl acetamide, N-vinyl-N-ethyl formamide, N-vinyl formamide, N-vinyl-N-methylpropionamide, N-vinyl-N-methyl-2-methylpropionamide, N-vinyl-2-methylpropionamide, N-vinyl-N,N'-dimethylurea, 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-N-propyl-3-methylene-2-pyrrolidone, 1-N-propyl-5-methylene-2-pyrrolidone, 1-isopropyl-3-methylene-2-pyrrolidone, 1-isopropyl-5-methylene-2-pyrrolidone, N-vinyl-N-ethyl acetamide, N-vinyl-N-ethyl formamide, N-vinyl formamide, N-vinyl isopropylamide, N-vinyl caprolactam, N-vinylimidazole, and mixtures thereof.

Non-limiting examples of hydrophilic 0-vinyl carbamates and O-vinyl carbonates monomers include N-2-hydroxyethyl vinyl carbamate and N-carboxy-β-alanine N-vinyl ester. Further examples of hydrophilic vinyl carbonate or vinyl carbamate monomers are disclosed in U.S. Pat. No. 5,070,215. Hydrophilic oxazolone monomers are disclosed in U.S. Pat. No. 4,910,277.

Other hydrophilic vinyl compounds include ethylene glycol vinyl ether (EGVE), di(ethylene glycol) vinyl ether (DEGVE), allyl alcohol, and 2-ethyl oxazoline.

The hydrophilic monomers may also be macromers or prepolymers of linear or branched poly(ethylene glycol), poly(propylene glycol), or statistically random or block copolymers of ethylene oxide and propylene oxide, having polymerizable moieties such as (meth)acrylates, styrenes, vinyl ethers, (meth)acrylamides, N-vinylamides, and the like. The macromers of these polyethers have one polymerizable group; the prepolymers may have two or more polymerizable groups.

The preferred hydrophilic monomers of the present invention are DMA, NVP, HEMA, VMA, NVA, and mixtures thereof. Preferred hydrophilic monomers include mixtures of DMA and HEMA. Other suitable hydrophilic monomers will be apparent to one skilled in the art.

Generally, there are no particular restrictions with respect to the amount of the hydrophilic monomer present in the reactive monomer mixture. The amount of the hydrophilic monomers may be selected based upon the desired characteristics of the resulting hydrogel, including water content, clarity, wettability, protein uptake, and the like. Wettability may be measured by contact angle, and desirable contact angles are less than about 100°, less than about 80°, and less than about 60°. The hydrophilic monomer may be present in an amount in the range of, for instance, about 0.1 to about 100 weight percent, alternatively in the range of about 1 to about 80 weight percent, alternatively about 5 to about 65 weight percent, alternatively in the range of about 40 to about 60 weight percent, or alternatively about 55 to about 60 weight percent, based on the total weight of the reactive components in the reactive monomer mixture.

Silicone-Containing Components

Silicone-containing components suitable for use in the invention comprise one or more polymerizable compounds, where each compound independently comprises at least one polymerizable group, at least one siloxane group, and one or more linking groups connecting the polymerizable group(s) to the siloxane group(s). The silicone-containing components may, for instance, contain from 1 to 220 siloxane repeat units, such as the groups defined below. The silicone-containing component may also contain at least one fluorine atom.

The silicone-containing component may comprise: one or more polymerizable groups as defined above; one or more optionally repeating siloxane units; and one or more linking groups connecting the polymerizable groups to the siloxane units. The silicone-containing component may comprise: one or more polymerizable groups that are independently a (meth)acrylate, a styryl, a vinyl ether, a (meth)acrylamide, an N-vinyl lactam, an N-vinylamide, an O-vinylcarbamate, an O-vinylcarbonate, a vinyl group, or mixtures of the foregoing; one or more optionally repeating siloxane units; and one or more linking groups connecting the polymerizable groups to the siloxane units.

The silicone-containing component may comprise: one or more polymerizable groups that are independently a (meth)acrylate, a (meth)acrylamide, an N-vinyl lactam, an N-vinylamide, a styryl, or mixtures of the foregoing; one or more optionally repeating siloxane units; and one or more linking groups connecting the polymerizable groups to the siloxane units.

The silicone-containing component may comprise: one or more polymerizable groups that are independently a (meth)acrylate, a (meth)acrylamide, or mixtures of the foregoing; one or more optionally repeating siloxane units; and one or more linking groups connecting the polymerizable groups to the siloxane units.

Formula A. The silicone-containing component may comprise one or more polymerizable compounds of Formula A:

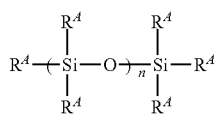

Formula A wherein:
at least one $R^A$ is a group of formula $R_g$-L- wherein $R_g$ is a polymerizable group and L is a linking group, and the remaining $R^A$ are each independently:
(a) $R_g$-L-,
(b) $C_1$-$C_{16}$ alkyl optionally substituted with one or more hydroxy, amino, amido, oxa, carboxy, alkyl carboxy, carbonyl, alkoxy, amido, carbamate, carbonate, halo, phenyl, benzyl, or combinations thereof,
(c) $C_3$-$C_{12}$ cycloalkyl optionally substituted with one or more alkyl, hydroxy, amino, amido, oxa, carbonyl, alkoxy, amido, carbamate, carbonate, halo, phenyl, benzyl, or combinations thereof,
(d) a $C_6$-$C_{14}$ aryl group optionally substituted with one or more alkyl, hydroxy, amino, amido, oxa, carboxy, alkyl carboxy, carbonyl, alkoxy, amido, carbamate, carbonate, halo, phenyl, benzyl, or combinations thereof,
(e) halo,
(f) alkoxy, cyclic alkoxy, or aryloxy,
(g) siloxy,
(h) alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or
(i) a monovalent siloxane chain comprising from 1 to 100 siloxane repeat units optionally substituted with alkyl, alkoxy, hydroxy, amino, oxa, carboxy, alkyl carboxy, alkoxy, amido, carbamate, halo or combinations thereof; and
n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different $R^A$ substituents and if different $R^A$ substituents are present, the n groups may be in random or block configuration.

In Formula A, three $R^A$ may each comprise a polymerizable group, alternatively two $R^A$ may each comprise a polymerizable group, or alternatively one $R^A$ may comprise a polymerizable group.

Formula B. The silicone-containing component of formula A may be a mono-functional polymerizable compound of formula B:

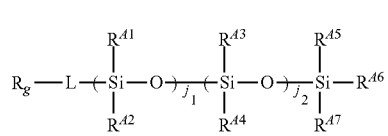

Formula B wherein:
Rg is a polymerizable group;
L is a linking group;
j1 and j2 are each independently whole numbers from 0 to 220, provided that the sum of j1 and j2 is from 1 to 220;
$R^{A1}$, $R^{A2}$, $R^{A3}$, $R^{A4}$, $R^{A5}$, and $R^{A7}$ are independently at each occurrence $C_1$-$C_6$ alkyl, $C_3$-$C_{12}$ cycloalkyl, $C_1$-$C_6$ alkoxy, $C_4$-$C_{12}$ cyclic alkoxy, alkoxy-alkyleneoxy-alkyl, aryl (e.g., phenyl), aryl-alkyl (e.g., benzyl), haloalkyl (e.g., partially or fully fluorinated alkyl), siloxy, fluoro, or combinations thereof, wherein each alkyl in the foregoing groups is optionally substituted with one or more hydroxy, amino, amido, oxa, carboxy, alkyl carboxy, carbonyl, alkoxy, carbamate, carbonate, halo, phenyl, or benzyl, each cycloalkyl is optionally substituted with one or more alkyl, hydroxy, amino, amido, oxa, carbonyl, alkoxy, carbamate, carbonate, halo, phenyl, or benzyl and each aryl is optionally substituted with one or more alkyl, hydroxy, amino, amido, oxa, carboxy, alkyl carboxy, carbonyl, alkoxy, carbamate, carbonate, halo, phenyl, or benzyl; and
$R^{A6}$ is siloxy, $C_1$-$C_8$ alkyl (e.g., $C_1$-$C_4$ alkyl, or butyl, or methyl), or aryl (e.g., phenyl), wherein alkyl and aryl may optionally be substituted with one or more fluorine atoms.

Formula B-1. Compounds of formula B may include compounds of formula B-1, which are compounds of formula B wherein j1 is zero and j2 is from 1 to 220, or j2 is from 1 to 100, or j2 is from 1 to 50, or j2 is from 1 to 20, or j2 is from 1 to 5, or j2 is 1.

B-2. Compounds of formula B may include compounds of formula B-2, which are compounds of formula B wherein j1 and j2 are independently from 4 to 100, or from 4 to 20, or from 4 to 10, or from 24 to 100, or from 10 to 100.

B-3. Compounds of formulae B, B-1, and B-2 may include compounds of formula B-3, which are compounds of formula B, B-1, or B-2 wherein $R^{A1}$, $R^{A2}$, $R^{A3}$, and $R^{A4}$ are independently at each occurrence $C_1$-$C_6$ alkyl or siloxy. Preferred alkyl are $C_1$-$C_3$ alkyl, or more preferably, methyl. Preferred siloxy is trimethylsiloxy.

B-4. Compounds of formulae B, B-1, B-2, and B-3 may include compounds of formula B-4, which are compounds of formula B, B-1, B-2, or B-3 wherein $R^{45}$ and $R^{47}$ are independently alkoxy-alkyleneoxy-alkyl, preferably they are independently a methoxy capped polyethyleneoxyalkyl of formula $CH_3O$—$[CH_2CH_2O]_p$—$CH_2CH_2CH_2$, wherein p is a whole number from 1 to 50.

B-5. Compounds of formulae B, B-1, B-2, and B-3 may include compounds of formula B-5, which are compounds of formula B, B-1, B-2, or B-3 wherein $R^{45}$ and $R^{47}$ are independently siloxy, such as trimethylsiloxy.

B-6. Compounds of formulae B, B-1, B-2, and B-3 may include compounds of formula B-6, which are compounds of formula B, B-1, B-2, or B-3 wherein $R^{45}$ and $R^{47}$ are independently $C_1$-$C_6$ alkyl, alternatively $C_1$-$C_4$ alkyl, or alternatively, butyl or methyl.

B-7. Compounds of formulae B, B-1, B-2, B-3, B-4, B-5, and B-6 may include compounds of formula B-7, which are compounds of formula B, B-1, B-2, B-3, B-4, B-5, or B-6 wherein $R^{46}$ is $C_1$-$C_8$ alkyl, preferably $C_1$-$C_6$ alkyl, more preferably $C_1$-$C_4$ alkyl (for example methyl, ethyl, n-propyl, or n-butyl). More preferably $R^{46}$ is n-butyl.

B-8. Compounds of formulae B, B-1, B-2, B-3, B-4, B-5, B-6, and B-7, may include compounds of formula B-8, which are compounds of formula B, B-1, B-2, B-3, B-4, B-5, B-6, or B-7 wherein Rg comprises styryl, vinyl carbonate, vinyl ether, vinyl carbamate, N-vinyl lactam, N-vinylamide, (meth)acrylate, or (meth)acrylamide. Preferably, Rg comprises (meth)acrylate, (meth)acrylamide, or styryl. More preferably, Rg comprises (meth)acrylate or (meth)acrylamide. When Rg is (meth)acrylamide, the nitrogen group may be substituted with $R^{49}$, wherein $R^{49}$ is H, $C_1$-$C_8$ alkyl (preferably $C_1$-$C_4$ alkyl, such as n-butyl, n-propyl, methyl or ethyl), or $C_3$-$C_8$ cycloalkyl (preferably $C_5$-$C_6$ cycloalkyl), wherein alkyl and cycloalkyl are optionally substituted with one or more groups independently selected from hydroxyl, amide, ether, silyl (e.g., trimethylsilyl), siloxy (e.g., trimethylsiloxy), alkyl-siloxanyl (where alkyl is itself optionally substituted with fluoro), aryl-siloxanyl (where aryl is itself optionally substituted with fluoro), and silyl-oxaalkylene- (where the oxaalkylene is itself optionally substituted with hydroxyl).

B-9. Compounds of formulae B, B-1, B-2, B-3, B-4, B-5, B-6, B-7, and B-8 may include compounds of formula B-9, which are compounds of formula B, B-1, B-2, B-3, B-4, B-5, B-6, B-7, or B-8 wherein the linking group comprises alkylene (preferably $C_1$-$C_4$ alkylene), cycloalkylene (preferably $C_5$-$C_6$ cycloalkylene), alkyleneoxy (preferably ethyleneoxy), haloalkyleneoxy (preferably haloethyleneoxy), amide, oxaalkylene (preferably containing 3 to 6 carbon atoms), siloxanyl, alkylenesiloxanyl, carbamate, alkyleneamine (preferably $C_1$-$C_6$ alkyleneamine), or combinations of two or more thereof, wherein the linking group is optionally substituted with one or more substituents independently selected from alkyl, hydroxyl, ether, amine, carbonyl, siloxy, and carbamate.

B-10. Compounds of formulae B, B-1, B-2, B-3, B-4, B-5, B-6, B-7, B-8, and B-9 may include compounds of formula B-10, which are compounds of formula B, B-1, B-2, B-3, B-4, B-5, B-6, B-7, B-8, or B-9 wherein the linking group is alkylene-siloxanyl-alkylene-alkyleneoxy-, or alkylene-siloxanyl-alkylene-[alkyleneoxy-alkylene-siloxanyl]$_q$-alkyleneoxy-, where q is from 1 to 50.

B-11. Compounds of formulae B, B-1, B-2, B-3, B-4, B-5, B-6, B-7, B-8, and B-9 may include compounds of formula B-11, which are compounds of formula B, B-1, B-2, B-3, B-4, B-5, B-6, B-7, B-8, or B-9 wherein the linking group is $C_1$-$C_6$ alkylene, preferably $C_1$-$C_3$ alkylene, more preferably n-propylene.

B-12. Compounds of formulae B, B-1, B-2, B-3, B-4, B-5, B-6, B-7, B-8, and B-9 may include compounds of formula B-12, which are compounds of formula B, B-1, B-2, B-3, B-4, B-5, B-6, B-7, B-8, or B-9 wherein the linking group is alkylene-carbamate-oxaalkylene. Preferably, the linking group is $CH_2CH_2N(H)$—$C(=O)$—$O$—$CH_2CH_2$—$O$—$CH_2CH_2CH_2$.

B-13. Compounds of formulae B, B-1, B-2, B-3, B-4, B-5, B-6, B-7, B-8, and B-9 may include compounds of formula B-13, which are compounds of formula B, B-1, B-2, B-3, B-4, B-5, B-6, B-7, B-8, or B-9 wherein the linking group is oxaalkylene. Preferably, the linking group is $CH_2CH_2$—$O$—$CH_2CH_2CH_2$.

B-14. Compounds of formulae B, B-1, B-2, B-3, B-4, B-5, B-6, B-7, B-8, and B-9 may include compounds of formula B-14, which are compounds of formula B, B-1, B-2, B-3, B-4, B-5, B-6, B-7, B-8, or B-9 wherein the linking group is alkylene-[siloxanyl-alkylene]$_q$-, where q is from 1 to 50. An example of such a linking group is: —$(CH_2)_3$—$[Si(CH_3)_2$—$O$—$Si(CH_3)_2$—$(CH_2)_2]_q$—.

B-15. Compounds of formulae B, B-1, B-2, B-3, B-4, B-5, B-6, B-7, B-8, and B-9 may include compounds of formula B-15, which are compounds of formula B, B-1, B-2, B-3, B-4, B-5, B-6, B-7, B-8, or B-9 wherein the linking group is alkyleneoxy-carbamate-alkylene-cycloalkylene-carbamate-oxaalkylene, wherein cycloalkylene is optionally substituted with or 1, 2, or 3 independently selected alkyl groups (preferably $C_1$-$C_3$ alkyl, more preferably methyl). An example of such a linking group is —$[OCH_2CH_2]_q$—$OC(=O)$—$NH$—$CH_2$-[1,3-cyclohexylene]-$NHC(=O)O$—$CH_2CH_2$—$O$—$CH_2CH_2$—, wherein the cyclohexylene is substituted at the 1 and 5 positions with 3 methyl groups.

B-16. Compounds of formulae B, B-1, B-2, B-3, B-4, B-5, B-6, B-7, B-8, and B-9 may include compounds of formula B-16, which are compounds of formula B, B-1, B-2, B-3, B-4, B-5, B-6, B-7, B-8, or B-9 wherein Rg comprises styryl and the linking group is a bond or is alkyleneoxy, wherein each alkylene in alkyleneoxy is independently optionally substituted with hydroxyl. An example of such a linking group is —$O$—$(CH_2)_3$—. Another example of such a linking group is —$O$—$CH_2CH(OH)CH_2$—$O$—$(CH_2)_3$—.

B-17. Compounds of formulae B, B-1, B-2, B-3, B-4, B-5, B-6, B-7, B-8, and B-9 may include compounds of formula B-17, which are compounds of formula B, B-1, B-2, B-3, B-4, B-5, B-6, B-7, B-8, or B-9 wherein Rg comprises styryl and the linking group is alkyleneamine. An example of such a linking group is —$NH$—$(CH_2)_3$—.

B-18. Compounds of formulae B, B-1, B-2, B-3, B-4, B-5, B-6, B-7, B-8, and B-9 may include compounds of formula B-18, which are compounds of formula B, B-1, B-2, B-3, B-4, B-5, B-6, B-7, B-8, or B-9 wherein the linking group is oxaalkylene optionally substituted with hydroxyl, siloxy, or silyl-alkyleneoxy (where the alkyleneoxy is itself optionally substituted with hydroxyl). An example of such a linking group is —$CH_2CH(G)CH_2$—$O$—$(CH_2)_3$—, wherein G is hydroxyl. In another example, G is $R_3SiO$— wherein two R groups are trimethylsiloxy and the third is $C_1$-$C_8$ alkyl (preferably $C_1$-$C_3$ alkyl, more preferably methyl) or the third is $C_3$-$C_8$ cycloalkyl. In a further example, G is $R_3Si$—$(CH_2)_3$—$O$—$CH_2CH(OH)CH_2$—$O$—, wherein two R groups are trimethylsiloxy and the third is $C_1$-$C_8$ alkyl (preferably $C_1$-$C_3$ alkyl, more preferably methyl) or $C_3$-$C_8$ cycloalkyl. In a still further example, G is a polymerizable group, such as (meth)acrylate. Such compounds may function as crosslinkers.

B-19. Compounds of formulae B, B-1, B-2, B-3, B-4, B-5, B-6, B-7, B-8, and B-9 may include compounds of formula B-19, which are compounds of formula B, B-1, B-2, B-3, B-4, B-5, B-6, B-7, B-8, or B-9 wherein Rg comprises styryl and the linking group is amine-oxaalkylene optionally substituted with hydroxyl. An example of such a linking group is —NH—CH$_2$CH(OH)CH$_2$—O—(CH$_2$)$_3$—.

B-20. Compounds of formulae B, B-1, B-2, B-3, B-4, B-5, B-6, B-7, B-8, and B-9 may include compounds of formula B-20, which are compounds of formula B, B-1, B-2, B-3, B-4, B-5, B-6, B-7, B-8, or B-9 wherein Rg comprises styryl and the linking group is alkyleneoxy-carbamate-oxaalkylene. An example of such a linking group is —O—(CH$_2$)$_2$—N(H)C(=O)O—(CH$_2$)$_2$—O—(CH$_2$)$_3$—.

B-21. Compounds of formulae B, B-1, B-2, B-3, B-4, B-5, B-6, B-7, B-8, and B-9 may include compounds of formula B-21, which are compounds of formula B, B-1, B-2, B-3, B-4, B-5, B-6, B-7, B-8, or B-9 wherein the linking group is alkylene-carbamate-oxaalkylene. An example of such a linking group is —(CH$_2$)$_2$—N(H)C(=O)O—(CH$_2$)$_2$—O—(CH$_2$)$_3$—.

Formula C. Silicone-containing components of formulae A, B, B-1, B-2, B-3, B-4, B-5, B-6, B-7, B-8, B-9, B-10, B-11, B-12, B-13, B-14, B-15, B-18, and B-21 may include compounds of formula C, which are compounds of formula A, B, B-1, B-2, B-3, B-4, B-5, B-6, B-7, B-8, B-9, B-10, B-11, B-12, B-13, B-14, B-15, B-18, or B-21 having the structure:

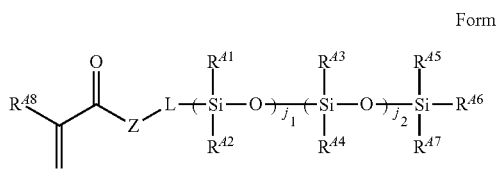

Formula C wherein

R$^{48}$ is hydrogen or methyl;

Z is O, S, or N(R$^{49}$); and

L, j1, j2, R$^{41}$, R$^{42}$, R$^{43}$, R$^{44}$, R$^{45}$, R$^{46}$, R$^{47}$, and R$^{49}$ are as defined in formula B or its various sub-formulae (e.g., B-1, B-2, etc.).

C-1. Compounds of formula C may include (meth)acrylates of formula C-1, which are compounds of formula C wherein Z is O.

C-2. Compounds of formula C may include (meth)acrylamides of formula C-2, which are compounds of formula C wherein Z is N(R$^{49}$), and R$^{49}$ is H.

C-3. Compounds of formulae C may include (meth)acrylamides of formula C-3, which are compounds of formula C wherein Z is N(R$^{49}$), and R$^{49}$ is C$_1$-C$_8$ alkyl that is unsubstituted or is optionally substituted as indicated above. Examples of R$^{49}$ include CH$_3$, —CH$_2$CH(OH)CH$_2$(OH), —(CH$_2$)$_3$-siloxanyl, —(CH$_2$)$_3$—SiR$_3$, and —CH$_2$CH(OH)CH$_2$—O—(CH$_2$)$_3$—SiR$_3$ where each R in the foregoing groups is independently selected from trimethylsiloxy, C$_1$-C$_8$ alkyl (preferably C$_1$-C$_3$ alkyl, more preferably methyl), and C$_3$-C$_8$ cycloalkyl. Further examples of R$^{49}$ include: —(CH$_2$)$_3$— Si(Me)(SiMe$_3$)$_2$, and —(CH$_2$)$_3$—Si(Me$_2$)-[O— SiMe$_2$]$_{1-10}$—CH$_3$.

Formula D. Compounds of formula C may include compounds of formula D:

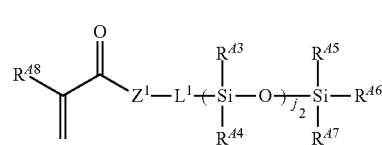

Formula D wherein

R$^{48}$ is hydrogen or methyl;

Z$^1$ is O or N(R$^{49}$);

L$^1$ is alkylene containing 1 to 8 carbon atoms, or oxaalkylene containing 3 to 10 carbon atoms, wherein L$^1$ is optionally substituted with hydroxyl; and j2, R$^{43}$, R$^{44}$, R$^{45}$, R$^{46}$, R$^{47}$, and R$^{49}$ are as defined above in formula B or its various sub-formulae (e.g., B-1, B-2, etc.).

D-1. Compounds of formula D may include compounds of formula D-1, which are compounds of formula D wherein L$^1$ is C$_2$-C$_5$ alkylene optionally substituted with hydroxyl. Preferably L$^1$ is n-propylene optionally substituted with hydroxyl.

D-2. Compounds of formula D may include compounds of formula D-2, which are compounds of formula D wherein L$^1$ is oxaalkylene containing 4 to 8 carbon atoms optionally substituted with hydroxyl. Preferably L$^1$ is oxaalkylene containing five or six carbon atoms optionally substituted with hydroxyl. Examples include —(CH$_2$)$_2$—O—(CH$_2$)$_3$—, and —CH$_2$CH(OH)CH$_2$—O—(CH$_2$)$_3$—.

D-3. Compounds of formulae D, D-1, and D-2 may include compounds of formula D-3, which are compounds of formula D, D-1, or D-2 wherein Z$^1$ is O.

D-4. Compounds of formulae D, D-1, and D-2 may include compounds of formula D-4, which are compounds of formula D, D-1, or D-2 wherein Z$^1$ is N(R$^{49}$), and R$^{49}$ is H.

D-5. Compounds of formulae D, D-1, and D-2 may include compounds of formula D-5, which are compounds of formula D, D-1, or D-2 wherein Z$^1$ is N(R$^{49}$), and R$^{49}$ is C$_1$-C$_4$ alkyl optionally substituted with 1 or 2 substituents selected from hydroxyl, siloxy, and C$_1$-C$_6$ alkyl-siloxanyl-.

D-6. Compounds of formulae D, D-1, D-2, D-3, D-4, and D-5 may include compounds of formula D-6, which are compounds of formula D, D-1, D-2, D-3, D-4, or D-5 wherein j2 is 1.

D-7. Compounds of formulae D, D-1, D-2, D-3, D-4, and D-5 may include compounds of formula D-7, which are compounds of formula D, D-1, D-2, D-3, D-4, or D-5 wherein j2 is from 2 to 220, or from 2 to 100, or from 10 to 100, or from 24 to 100, or from 4 to 20, or from 4 to 10.

D-8. Compounds of formulae D, D-1, D-2, D-3, D-4, D-5, D-6, and D-7 may include compounds of formula D-8, which are compounds of formula D, D-1, D-2, D-3, D-4, D-5, D-6, or D-7 wherein R$^{43}$, R$^{44}$, R$^{45}$, R$^{46}$, and R$^{47}$ are independently C$_1$-C$_6$ alkyl or siloxy. Preferably R$^{43}$, R$^{44}$, R$^{45}$, R$^{46}$, and R$^{47}$ are independently selected from methyl, ethyl, n-propyl, n-butyl, and trimethylsiloxy. More preferably, R$^{43}$, R$^{44}$, R$^{45}$, R$^{46}$, and R$^{47}$ are independently selected from methyl, n-butyl, and trimethylsiloxy.

D-9. Compounds of formulae D, D-1, D-2, D-3, D-4, D-5, D-6, and D-7 may include compounds of formula D-9, which are compounds of formula D, D-1, D-2, D-3, D-4, D-5, D-6, or D-7 wherein R$^{43}$ and R$^{44}$ are independently C$_1$-C$_6$ alkyl (e.g., methyl or ethyl) or siloxy (e.g., trimethylsiloxy), and R$^{45}$, R$^{46}$, and R$^{47}$ are independently C$_1$-C$_6$ alkyl (e.g., methyl, ethyl, n-propyl, or n-butyl).

Formula E. The silicone-containing component for use in the invention may comprise a multi-functional silicone-containing component. Thus, for example, the silicone-containing component of formula A may comprise a bifunctional material of formula E:

Formula E

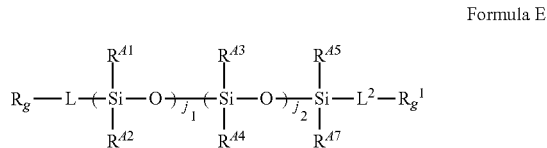

wherein
Rg, L, j1, j2, $R^{A1}$, $R^{A2}$, $R^{A3}$, $R^{A4}$, $R^{A5}$, and $R^{A7}$ are as defined above for formula B or its various sub-formulae (e.g., B-1, B-2, etc.);
$L^2$ is a linking group; and
$Rg^1$ is a polymerizable group.

E-1. Compounds of formula E may include compounds of formula E-1, which are compounds of formula E wherein Rg and $Rg^1$ are each a vinyl carbonate of structure $CH_2$=CH—O—C(=O)—O— or structure $CH_2$=C($CH_3$)—O—C(=O)—O—.

E-2. Compounds of formula E may include compounds of formula E-2, which are compounds of formula E wherein Rg and $Rg^1$ are each (meth)acrylate.

E-3. Compounds of formula E may include compounds of formula E-3, which are compounds of formula E wherein Rg and $Rg^1$ are each (meth)acrylamide, wherein the nitrogen group may be substituted with $R^{A9}$ (wherein $R^{A9}$ is as defined above).

E-4. Suitable compounds of formulae E, E-1, E-2, and E-3 include compounds of formula E-4, which are compounds of formula E, E-1, E-2, or E-3 wherein j1 is zero and j2 is from 1 to 220, or j2 is from 1 to 100, or j2 is from 1 to 50, or j2 is from 1 to 20.

E-5. Suitable compounds of formulae E, E-1, E-2, and E-3 include compounds of formula E-5, which are compounds of formula E, E-1, E-2, or E-3, wherein j1 and j2 are independently from 4 to 100.

E-6. Suitable compounds of formulae E, E-1, E-2, E-3, E-4, and E-5 include compounds of formula E-6, which are compounds of formula E, E-1, E-2, E-3, E-4, or E-5 wherein $R^{A1}$, $R^{A2}$, $R^{A3}$, $R^{A4}$, and $R^{A5}$ are independently at each occurrence $C_1$-$C_6$ alkyl, preferably they are independently $C_1$-$C_3$ alkyl, or preferably, each is methyl.

E-7. Suitable compounds of formulae E, E-1, E-2, E-3, E-4, E-5, and E-6 include compounds of formula E-7, which are compounds of formula E, E-1, E-2, E-3, E-4, E-5, or E-6 wherein $R^{A7}$ is alkoxy-alkyleneoxy-alkyl, preferably it is a methoxy capped polyethyleneoxyalkyl of formula $CH_3O$—[$CH_2CH_2O$]$_p$—$CH_2CH_2CH_2$, wherein p is a whole number from 1 to 50, or from 1 to 30, or from 1 to 10, or from 6 to 10.

E-8. Suitable compounds of formulae E, E-1, E-2, E-3, E-4, E-5, E-6, and E-7 include compounds of formula E-8, which are compounds of formula E, E-1, E-2, E-3, E-4, E-5, E-6, or E-7 wherein L comprises alkylene, carbamate, siloxanyl, cycloalkylene, amide, haloalkyleneoxy, oxaalkylene, or combinations of two or more thereof, wherein the linking group is optionally substituted with one or more substituents independently selected from alkyl, hydroxyl, ether, amine, carbonyl, and carbamate.

E-9. Suitable compounds of formulae E, E-1, E-2, E-3, E-4, E-5, E-6, E-7, and E-8 include compounds of formula E-9, which are compounds of formula E, E-1, E-2, E-3, E-4, E-5, E-6, E-7, or E-8 wherein $L^2$ comprises alkylene, carbamate, siloxanyl, cycloalkylene, amide, haloalkyleneoxy, oxaalkylene, or combinations of two or more thereof, wherein the linking group is optionally substituted with one or more substituents independently selected from alkyl, hydroxyl, ether, amine, carbonyl, and carbamate.

Examples of silicone-containing components suitable for use in the invention include, but are not limited to, compounds listed in Table 2. Where the compounds in Table 2 contain polysiloxane groups, the number of SiO repeat units in such compounds, unless otherwise indicated, is preferably from 3 to 100, more preferably from 3 to 40, or still more preferably from 3 to 20.

TABLE 2

| | |
|---|---|
| 1 | mono-methacryloxypropyl terminated mono-n-butyl terminated polydimethylsiloxanes (mPDMS) (preferably containing from 3 to 15 SiO repeating units) |
| 2 | mono-acryloxypropyl terminated mono-n-butyl terminated polydimethylsiloxane |
| 3 | mono(meth)acryloxypropyl terminated mono-n-methyl terminated polydimethylsiloxane |
| 4 | mono(meth)acryloxypropyl terminated mono-n-butyl terminated polydiethylsiloxane |
| 5 | mono(meth)acryloxypropyl terminated mono-n-methyl terminated polydiethylsiloxane |
| 6 | mono(meth)acrylamidoalkylpolydialkylsiloxanes |
| 7 | mono(meth)acryloxyalkyl terminated mono-alkyl polydiarylsiloxanes |
| 8 | 3-methacryloxypropyltris(trimethylsiloxy)silane (TRIS) |
| 9 | 3-methacryloxypropylbis(trimethylsiloxy)methylsilane |
| 10 | 3-methacryloxypropylpentamethyl disiloxane |
| 11 | mono(meth)acrylamidoalkylpolydialkylsiloxanes |
| 12 | mono(meth)acrylamidoalkyl polydimethylsiloxanes |
| 13 | N-(2,3-dihydroxypropane)-N'-(propyl tetra(dimethylsiloxy) dimethylbutylsilane)acrylamide |
| 14 | N-[3-tris(trimethylsiloxy)silyl]-propyl acrylamide (TRIS-Am) |
| 15 | 2-hydroxy-3-[3-methyl-3,3-di(trimethylsiloxy)silylpropoxy]-propyl methacrylate (SiMAA) |
| 16 | 2-hydroxy-3-methacryloxypropyloxypropyl-tris(trimethylsiloxy)silane |
| 17 | 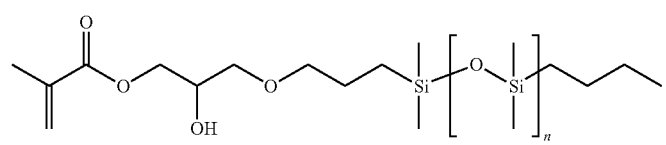 |

TABLE 2-continued
mono-(2-hydroxy-3-methacryloxypropyloxy)-propyl terminated mono-n-butyl terminated polydimethylsiloxanes (OH-mPDMS) (containing from 4 to 30, or from 4 to 20, or from 4 to 15 SiO repeat units)
18 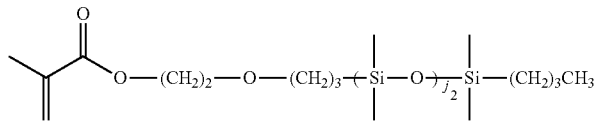
19 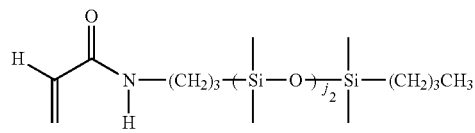
20 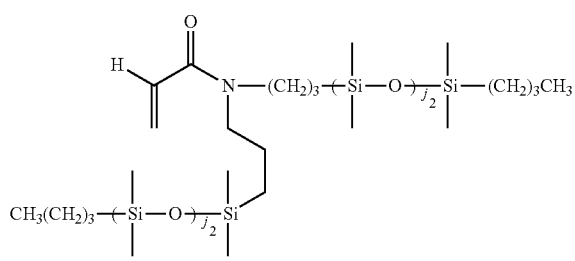
21 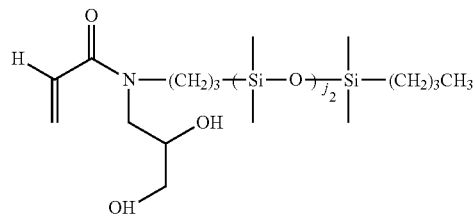
22 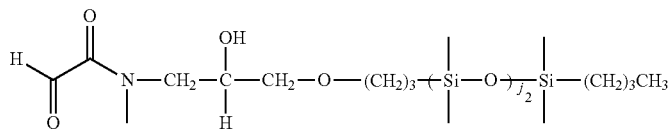
23 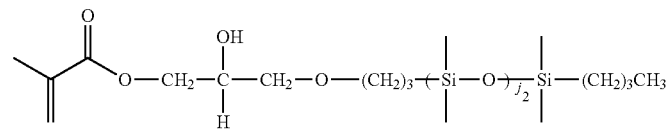
24 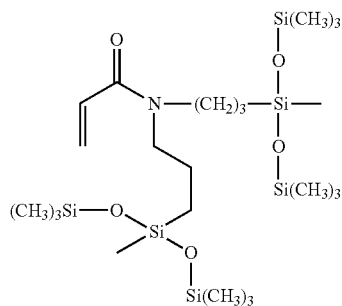

Additional non-limiting examples of suitable silicone-containing components are listed in Table 3. Unless otherwise indicated, j2 where applicable is preferably from 1 to 100, more preferably from 3 to 40, or still more preferably from 3 to 15. In compounds containing j1 and j2, the sum of j1 and j2 is preferably from 2 to 100, more preferably from 3 to 40, or still more preferably from 3 to 15.

TABLE 3

25 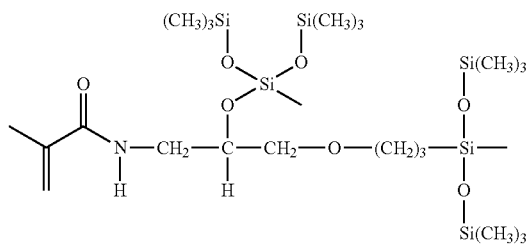

26 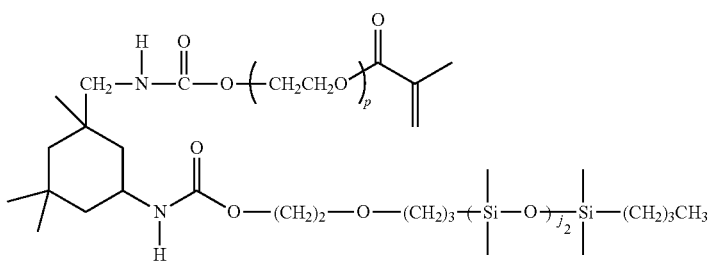

p is 1 to 10

27 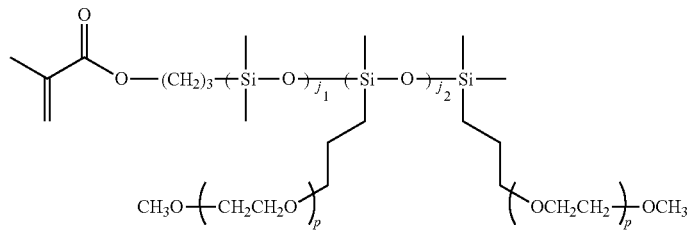

p is 5-10

28 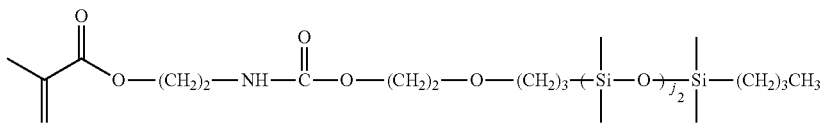

29 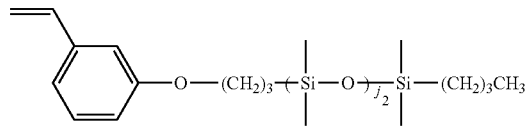

| 30 | 1,3-bis[4-(vinyloxycarbonyloxy)but-1-yl]tetramethyl-disiloxane |
| --- | --- |
| 31 | 3-(vinyloxycarbonylthio)propyl-[tris(trimethylsiloxy)silane] |
| 32 | 3-[tris(trimethylsiloxy)silyl]propyl allyl carbamate |
| 33 | 3-[tris(trimethylsiloxy)silyl]propyl vinyl carbamate |
| 34 | tris(trimethylsiloxy)silylstyrene (Styryl-TRIS) |

TABLE 3-continued
35 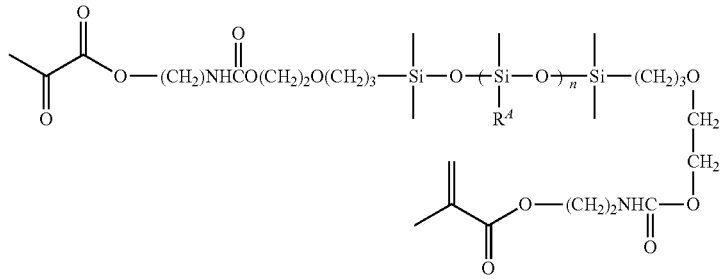
$R^A$ = CH$_3$ (a) or CH$_2$CH$_2$CF$_3$ (b) or CH$_2$—(CH$_2$)$_2$—[OCH$_2$CH$_2$]$_{1-10}$—OCH$_3$ (c); a + b + c = n
36 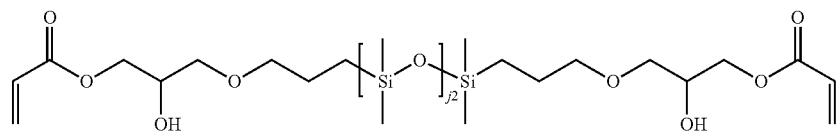
37 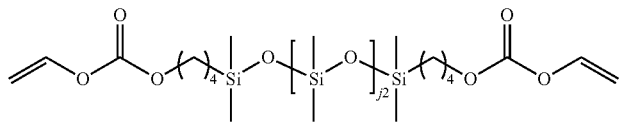
38 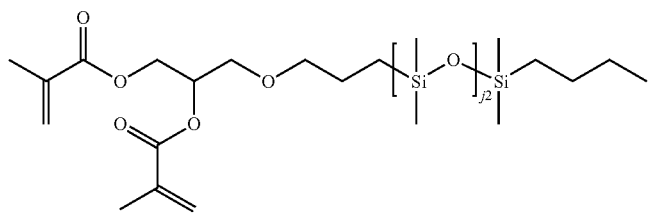
39 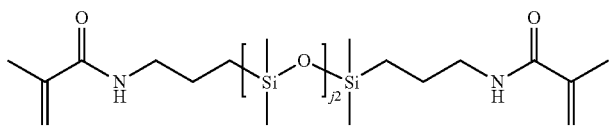
40 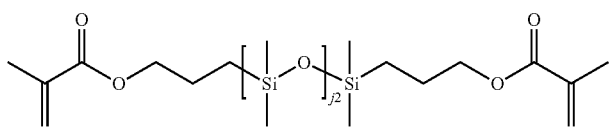
41 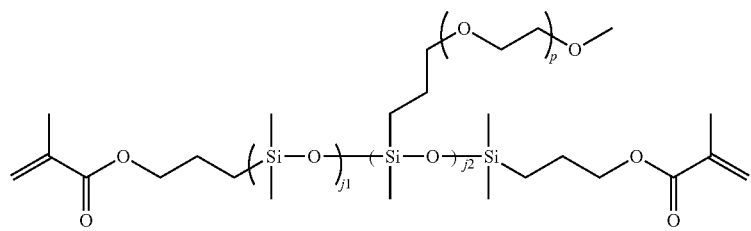
j1 = 80-90
j2 = 5-6
p = 7-8

Mixtures of silicone-containing components may be used. By way of example, suitable mixtures may include, but are not limited to: a mixture of mono-(2-hydroxy-3-methacryloxypropyloxy)-propyl terminated mono-n-butyl terminated polydimethylsiloxane (OH-mPDMS) having different molecular weights, such as a mixture of OH-mPDMS containing 4 and 15 SiO repeat units; a mixture of OH-mPDMS with different molecular weights (e.g., containing 4 and 15 repeat SiO repeat units) together with a silicone based crosslinker, such as bis-3-acryloxy-2-hydroxypropyloxypropyl polydimethylsiloxane (ac-PDMS); a mixture of 2-hydroxy-3-[3-methyl-3,3-di(trimethylsiloxy)silylpropoxy]-propyl methacrylate (SiMAA) and mono-methacryloxypropyl terminated mono-n-butyl terminated polydimethylsiloxane (mPDMS), such as mPDMS 1000.

Silicone-containing components for use in the invention may have an average molecular weight of from about 400 to about 4000 daltons.

The silicone containing component(s) may be present in amounts up to about 95 weight %, or from about 10 to about 80 weight %, or from about 20 to about 70 weight %, based upon all reactive components of the reactive mixture (excluding diluents).

Polyamides

The reactive mixture may include at least one polyamide. As used herein, the term "polyamide" refers to polymers and copolymers comprising repeating units containing amide groups. The polyamide may comprise cyclic amide groups, acyclic amide groups and combinations thereof and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups.

Examples of suitable acyclic polyamides include polymers and copolymers comprising repeating units of Formulae G1 and G2:

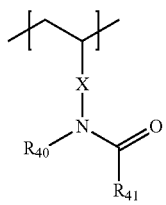

Formula G1

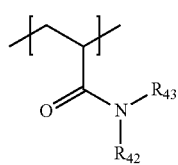

Formula G2 wherein X is a direct bond, —(CO)—, or —(CONHR$_{44}$)—, wherein R$_{44}$ is a C$_1$ to C$_3$ alkyl group; R$_{40}$ is selected from H, straight or branched, substituted or unsubstituted C$_1$ to C$_4$ alkyl groups; R$_{41}$ is selected from H, straight or branched, substituted or unsubstituted C$_1$ to C$_4$ alkyl groups, amino groups having up to two carbon atoms, amide groups having up to four carbon atoms, and alkoxy groups having up to two carbon groups; R$_{42}$ is selected from H, straight or branched, substituted or unsubstituted C$_1$ to C$_4$ alkyl groups; or methyl, ethoxy, hydroxyethyl, and hydroxymethyl; R$_{43}$ is selected from H, straight or branched, substituted or unsubstituted C$_1$ to C$_4$ alkyl groups; or methyl, ethoxy, hydroxyethyl, and hydroxymethyl; wherein the number of carbon atoms in R$_{40}$ and R$_{41}$ taken together is 8 or less, including 7, 6, 5, 4, 3, or less; and wherein the number of carbon atoms in R$_{42}$ and R$_{43}$ taken together is 8 or less, including 7, 6, 5, 4, 3, or less. The number of carbon atoms in R$_{40}$ and R$_{41}$ taken together may be 6 or less or 4 or less. The number of carbon atoms in R$_{42}$ and R$_{43}$ taken together may be 6 or less. As used herein substituted alkyl groups include alkyl groups substituted with an amine, amide, ether, hydroxyl, carbonyl or carboxy groups or combinations thereof.

R$_{40}$ and R$_{41}$ may be independently selected from H, substituted or unsubstituted C$_1$ to C$_2$ alkyl groups. X may be a direct bond, and R$_{40}$ and R$_{41}$ may be independently selected from H, substituted or unsubstituted C$_1$ to C$_2$ alkyl groups. R$_{42}$ and R$_{43}$ can be independently selected from H, substituted or unsubstituted C$_1$ to C$_2$ alkyl groups, methyl, ethoxy, hydroxyethyl, and hydroxymethyl.

The acyclic polyamides of the present invention may comprise a majority of the repeating units of Formula LV or Formula LVI, or the acyclic polyamides can comprise at least 50 mole percent of the repeating unit of Formula G or Formula G1, including at least 70 mole percent, and at least 80 mole percent. Specific examples of repeating units of Formula G and Formula G1 include repeating units derived from N-vinyl-N-methylacetamide, N-vinylacetamide, N-vinyl-N-methylpropionamide, N-vinyl-N-methyl-2-methylpropionamide, N-vinyl-2-methylpropionamide, N-vinyl-N, N'-dimethylurea, N, N-dimethylacrylamide, methacrylamide, and acyclic amides of Formulae G2 and G3:

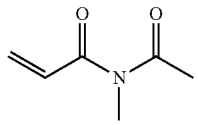

Formula G2

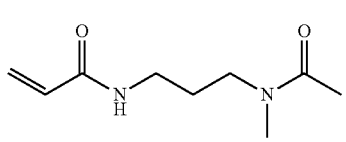

Formula G3

Examples of suitable cyclic amides that can be used to form the cyclic polyamides of include α-lactam, β-lactam, γ-lactam, δ-lactam, and ε-lactam. Examples of suitable cyclic polyamides include polymers and copolymers comprising repeating units of Formula G4:

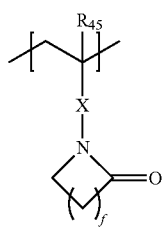

Formula G4 wherein $R_{45}$ is a hydrogen atom or methyl group; wherein f is a number from 1 to 10; wherein X is a direct bond, —(CO)—, or —(CONHR$_{46}$)—, wherein $R_{46}$ is a $C_1$ to $C_3$ alkyl group. In Formula LIX, f may be 8 or less, including 7, 6, 5, 4, 3, 2, or 1. In Formula G4, f may be 6 or less, including 5, 4, 3, 2, or 1. In Formula G4, f may be from 2 to 8, including 2, 3, 4, 5, 6, 7, or 8. In Formula LIX, f may be 2 or 3. When X is a direct bond, f may be 2. In such instances, the cyclic polyamide may be polyvinylpyrrolidone (PVP).

The cyclic polyamides of the present invention may comprise 50 mole percent or more of the repeating unit of Formula G4, or the cyclic polyamides can comprise at least 50 mole percent of the repeating unit of Formula G4, including at least 70 mole percent, and at least 80 mole percent.

The polyamides may also be copolymers comprising repeating units of both cyclic and acyclic amides. Additional repeating units may be formed from monomers selected from hydroxyalkyl(meth)acrylates, alkyl(meth)acrylates, other hydrophilic monomers and siloxane substituted (meth) acrylates. Any of the monomers listed as suitable hydrophilic monomers may be used as co-monomers to form the additional repeating units. Specific examples of additional monomers which may be used to form polyamides include 2-hydroxyethyl (meth)acrylate, vinyl acetate, acrylonitrile, hydroxypropyl (meth)acrylate, methyl (meth)acrylate and hydroxybutyl (meth)acrylate, dihydroxypropyl (meth)acrylate, polyethylene glycol mono(meth)acrylate, and the like and mixtures thereof. Ionic monomers may also be included. Examples of ionic monomers include (meth)acrylic acid, N-[(ethenyloxy)carbonyl]-β-alanine (VINAL, CAS #148-969-96-4), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT, carboxybetaine; CAS 79704-35-1), 1-propanaminium, N,N-dimethyl-N-[3-[(1-oxo-2-propen-1-yl)amino]propyl]-3-sulfo-, inner salt (SBT, sulfobetaine, CAS 80293-60-3), 3,5-Dioxa-8-aza-4-phosphaundec-10-en-1-aminium, 4-hydroxy-N,N,N-trimethyl-9-oxo-, inner salt, 4-oxide (9CI) (PBT, phosphobetaine, CAS 163674-35-9, 2-methacryloyloxyethyl phosphorylcholine, 3-(dimethyl(4-vinylbenzyl)ammonio)propane-1-sulfonate (DMVBAPS), 3-((3-acrylamidopropyl)dimethylammonio) propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio) propane-1-sulfonate (APDAPS), methacryloyloxy)propyl) dimethylammonio)propane-1-sulfonate (MAPDAPS).

The reactive monomer mixture may comprise both an acyclic polyamide and a cyclic polyamide or copolymers thereof. The acyclic polyamide can be any of those acyclic polyamides described herein or copolymers thereof, and the cyclic polyamide can be any of those cyclic polyamides described herein or copolymers thereof. The polyamide may be selected from the group polyvinylpyrrolidone (PVP), polyvinylmethyacetamide (PVMA), polydimethylacrylamide (PDMA), polyvinylacetamide (PNVA), poly(hydroxyethyl(meth)acrylamide), polyacrylamide, and copolymers and mixtures thereof. The polyamide may be a mixture of PVP (e.g., PVP K90) and PVMA (e.g., having a Mw of about 570 KDa).

The total amount of all polyamides in the reactive mixture may be in the range of between 1 weight percent and about 35 weight percent, including in the range of about 1 weight percent to about 15 weight percent, and in the range of about 5 weight percent to about 15 weight percent, in all cases, based on the total weight of the reactive components of the reactive monomer mixture.

Without intending to be bound by theory, when used with a silicone hydrogel, the polyamide functions as an internal wetting agent. The polyamides of the present invention may be non-polymerizable, and in this case, are incorporated into the silicone hydrogels as semi-interpenetrating networks. The polyamides are entrapped or physically retained within the silicone hydrogels. Alternatively, the polyamides of the present invention may be polymerizable, for example as polyamide macromers or prepolymers, and in this case, are covalently incorporated into the silicone hydrogels. Mixtures of polymerizable and non-polymerizable polyamides may also be used.

When the polyamides are incorporated into the reactive monomer mixture they may have a weight average molecular weight of at least 100,000 daltons; greater than about 150,000; between about 150,000 to about 2,000,000 daltons; between about 300,000 to about 1,800,000 daltons. Higher molecular weight polyamides may be used if they are compatible with the reactive monomer mixture.

Cross-Linking Agents

It is generally desirable to add one or more cross-linking agents, also referred to as cross-linking monomers, multifunctional macromers, and prepolymers, to the reactive mixture. The cross-linking agents may be selected from bifunctional crosslinkers, trifunctional crosslinkers, tetrafunctional crosslinkers, and mixtures thereof, including silicone-containing and non-silicone containing cross-linking agents. Non-silicone-containing cross-linking agents include ethylene glycol dimethacrylate (EGDMA), tetraethylene glycol dimethacrylate (TEGDMA), trimethylolpropane trimethacrylate (TMPTMA), triallyl cyanurate (TAC), glycerol trimethacrylate, methacryloxyethyl vinylcarbonate (HEMAVc), allylmethacrylate, methylene bisacrylamide (MBA), and polyethylene glycol dimethacrylate wherein the polyethylene glycol has a molecular weight up to about 5000 Daltons. The cross-linking agents are used in the usual amounts, e.g., from about 0.000415 to about 0.0156 mole per 100 grams of reactive Formulas in the reactive mixture. Alternatively, if the hydrophilic monomers and/or the silicone-containing components are multifunctional by molecular design or because of impurities, the addition of a cross-linking agent to the reactive mixture is optional. Examples of hydrophilic monomers and macromers which can act as the cross-linking agents and when present do not require the addition of an additional cross-linking agent to the reactive mixture include (meth)acrylate and (meth)acrylamide end-capped polyethers. Other cross-linking agents will be known to one skilled in the art and may be used to make the silicone hydrogel of the present invention.

It may be desirable to select crosslinking agents with similar reactivity to one or more of the other reactive components in the formulation. In some cases, it may be desirable to select a mixture of crosslinking agents with different reactivity in order to control some physical, mechanical or biological property of the resulting silicone hydrogel. The structure and morphology of the silicone hydrogel may also be influenced by the diluent(s) and cure conditions used.

Multifunctional silicone-containing components, including macromers, cross-linking agents, and prepolymers, may also be included to further increase the modulus and retain tensile strength. The silicone containing cross-linking agents may be used alone or in combination with other cross-linking agents. An example of a silicone containing component which can act as a cross-linking agent and, when present, does not require the addition of a crosslinking monomer to the reactive mixture includes a, w-bismethacryloxypropyl polydimethylsiloxane. Another example is bis-3-acryloxy-2-hydroxypropyloxypropyl polydimethylsiloxane (ac-PDMS).

Cross-linking agents that have rigid chemical structures and polymerizable groups that undergo free radical polymerization may also be used. Non-limiting examples of suitable rigid structures include cross-linking agents comprising phenyl and benzyl ring, such are 1,4-phenylene diacrylate, 1,4-phenylene dimethacrylate, 2,2-bis(4-methacryloxyphenyl)-propane, 2,2-bis[4-(2-acryloxyethoxy)phenyl]propane, 2,2-bis[4-(2-hydroxy-3-methacryloxypropoxy)-phenyl]propane, and 4-vinylbenzyl methacrylate, and combinations thereof. Rigid crosslinking agents may be included in amounts between about 0.5 and about 15, or 2-10, 3-7 based upon the total weight of all of the reactive components. The physical and mechanical properties of the silicone hydrogels of the present invention may be optimized for a particular use by adjusting the components in the reactive mixture.

Non-limiting examples of silicone cross-linking agents also include the multi-functional silicone-containing components described above, such as compounds of Formula E (and its sub-formulae) and the multi-functional compounds shown in Table 3.

Further Constituents

The reactive mixture may contain additional components such as, but not limited to, diluents, initiators, UV absorbers, visible light absorbers, photochromic compounds, pharmaceuticals, nutraceuticals, antimicrobial substances, tints, pigments, copolymerizable dyes, nonpolymerizable dyes, release agents, and combinations thereof.

Classes of suitable diluents for silicone hydrogel reactive mixtures include alcohols having 2 to 20 carbon atoms, amides having 10 to 20 carbon atoms derived from primary amines and carboxylic acids having 8 to 20 carbon atoms. The diluents may be primary, secondary, and tertiary alcohols.

Generally, the reactive components are mixed in a diluent to form a reactive mixture. Suitable diluents are known in the art. For silicone hydrogels, suitable diluents are disclosed in WO 03/022321 and U.S. Pat. No. 6,020,445, the disclosure of which is incorporated herein by reference. Classes of suitable diluents for silicone hydrogel reactive mixtures include alcohols having 2 to 20 carbons, amides having 10 to 20 carbon atoms derived from primary amines, and carboxylic acids having 8 to 20 carbon atoms. Primary and tertiary alcohols may be used. Preferred classes include alcohols having 5 to 20 carbons and carboxylic acids having 10 to 20 carbon atoms. Specific diluents which may be used include 1-ethoxy-2-propanol, diisopropylaminoethanol, iso-propanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, (3-acetoxy-2-hydroxypropyloxy)-propylbis(trimethylsiloxy) methylsilane, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino) ethanol mixtures thereof and the like. Examples of amide diluents include N,N-dimethyl propionamide and dimethyl acetamide.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, t-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like. If a diluent is present, generally there are no particular restrictions with respect to the amount of diluent present. When diluent is used, the diluent may be present in an amount in the range of about 2 to about 70 weight percent, including in the range of about 5 to about 50 weight percent, and in the range of about 15 to about 40 weight percent, based on the total weight of the reactive mixtures (including reactive and nonreactive Formulas). Mixtures of diluents may be used.

A polymerization initiator may be used in the reactive mixture. The polymerization initiator may include, for instance, at least one of lauroyl peroxide, benzoyl peroxide, iso-propyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphine oxide (Irgacure 819), 2,4,6-trimethylbenzyldiphenyl phosphine oxide and 2,4,6-trimethylbenzoyl diphenylphosphine oxide, benzoin methyl ester and a combination of cam-phorquinone and ethyl 4-(N,N-dimethylamino)benzoate.

Commercially available (from IGM Resins B.V., The Netherlands) visible light initiator systems include Irgacure® 819, Irgacure® 1700, Irgacure® 1800, Irgacure® 819, Irgacure® 1850 and Lucrin® TPO initiator. Commercially available (from IGM Resins B.V.) UV photoinitiators include Darocur® 1173 and Darocur® 2959. These and other photoinitiators which may be used are disclosed in Volume III, Photoinitiators for Free Radical Cationic & Anionic Photopolymerization, 2nd Edition by J. V. Crivello & K. Dietliker; edited by G. Bradley; John Wiley and Sons; New York; 1998. The initiator is used in the reactive mixture in effective amounts to initiate photopolymerization of the reactive mixture, e.g., from about 0.1 to about 2 parts by weight per 100 parts of reactive monomer mixture. Polymerization of the reactive mixture can be initiated using the appropriate choice of heat or visible or ultraviolet light or other means depending on the polymerization initiator used. Alternatively, initiation can be conducted using e-beam without a photoinitiator. However, when a photoinitiator is used, the preferred initiators are bisacylphosphine oxides, such as bis(2,4,6-tri-methylbenzoyl)-phenyl phosphine oxide (Irgacure® 819) or a combination of 1-hydroxycyclohexyl phenyl ketone and bis(2,6-dimethoxybenzoyl)-2,4-4-trimethylpentyl phosphine oxide (DMBAPO).

While the compounds of formula I are the preferred high energy light absorbing compounds for use in the invention, other high energy light absorbing compounds are described in the examples and may be used alone or in combination with the compounds of formula I. These include, for instance, compounds of formula II, compounds of formula III, and/or compounds of formula IV:

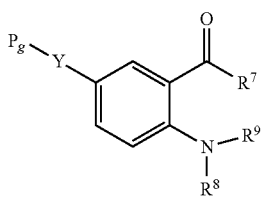

(II)

wherein Y is a linking group; $P_g$ is a polymerizable group; $R^7$ is $C_1$-$C_6$ alkyl; and $R^8$ and $R^9$ are independently H or $C_1$-$C_6$ alkyl. Preferably, $R^7$ is methyl or ethyl. Preferably, $R^8$ and $R^9$ are both H. Preferably, $P_g$ is (meth)acrylate or (meth)acrylamide. Preferably, Y is $C_1$-$C_8$ oxaalkylene (e.g., —CH$_2$CH$_2$—O—), $C_1$-$C_8$ thialkylene (e.g., —CH$_2$CH$_2$—S—), or $C_1$-$C_8$ alkyleneamine (e.g., —CH$_2$CH$_2$—N(H)— or —CH$_2$CH$_2$—N(CH$_3$)—).

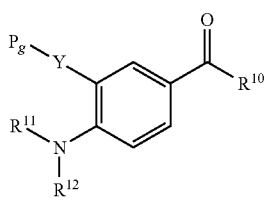

(III)

wherein Y is a linking group; $P_g$ is a polymerizable group; $R^{10}$ is $C_1$-$C_6$ alkyl; and $R^{11}$ and $R^{12}$ are independently H or $C_1$-$C_6$ alkyl. Preferably, $R^{10}$ is methyl or ethyl. Preferably, $R^{11}$ and $R^{12}$ are both H. Preferably, $P_g$ is (meth)acrylate or (meth)acrylamide. Preferably, Y is $C_1$-$C_8$ oxaalkylene (e.g., —CH$_2$CH$_2$—O—), $C_1$-$C_8$ thialkylene (e.g., —CH$_2$CH$_2$—S—), or $C_1$-$C_8$ alkyleneamine (e.g., —CH$_2$CH$_2$—N(H)— or —CH$_2$CH$_2$—N(CH$_3$)—).

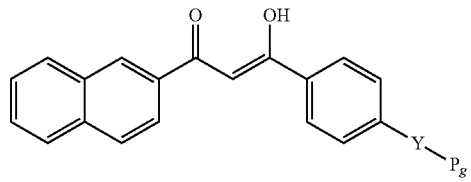

(IV)

wherein Y is a linking group and $P_g$ is a polymerizable group. Preferably Y is a bond. Preferably, Pg is vinyl. Preferred compounds of formula IV include compounds of formula IV-1:

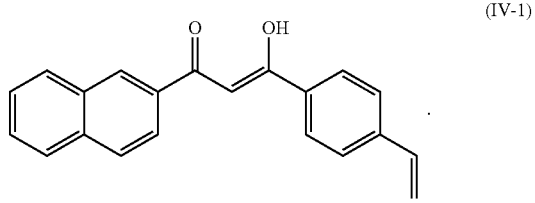 [SMILES: C=Cc1ccc(/C(O)=C/C(=O)c2ccc3ccccc3c2)cc1]

(IV-1)

The reactive mixture for making the ophthalmic devices of the invention may comprise, in addition to one or more high energy light absorbing compounds, any of the other polymerizable compounds and optional components described above.

Preferred reactive mixtures may comprise: a high energy light absorbing compound and a hydrophilic component.

Preferred reactive mixtures may comprise: a high energy light absorbing compound and a hydrophilic component selected from DMA, NVP, HEMA, VMA, NVA, methacrylic acid, and mixtures thereof. Preferred are mixtures of HEMA and methacrylic acid.

Preferred reactive mixtures may comprise: a high energy light absorbing compound, a hydrophilic component, and a silicone-containing component.

Preferred reactive mixtures may comprise: a high energy light absorbing compound, a hydrophilic component, and a silicone-containing component comprising a compound of formula D (or its sub-formulae, such as D-1, D-2, etc.).

Preferred reactive mixtures may comprise: a high energy light absorbing compound, a hydrophilic component selected from DMA, NVP, HEMA, VMA, NVA, and mixtures thereof; a silicone-containing component comprising a compound of formula D (or its sub-formulae, such as D-1, D-2, etc.); and an internal wetting agent.

Preferred reactive mixtures may comprise: a high energy light absorbing compound, a hydrophilic component selected from DMA, HEMA and mixtures thereof; a silicone-containing component selected from 2-hydroxy-3-[3-methyl-3,3-di(trimethylsiloxy)silylpropoxy]-propyl methacrylate (SiMAA), mono-methacryloxypropyl terminated mono-n-butyl terminated polydimethylsiloxane (mPDMS), mono-(2-hydroxy-3-methacryloxypropyl)-propyl ether terminated mono-n-butyl terminated polydimethylsiloxane (OH-mPDMS), and mixtures thereof;

and a wetting agent (preferably PVP or PVMA). For the hydrophilic component, mixtures of DMA and HEMA are preferred. For the silicone containing component, mixtures of SiMAA and mPDMS are preferred.

Preferred reactive mixtures may comprise: a high energy light absorbing compound, a hydrophilic component comprising a mixture of DMA and HEMA; a silicone-containing component comprising a mixture of OH-mPDMS having from 2 to 20 repeat units (preferably a mixture of 4 and 15 repeat units). Preferably, the reactive mixture further comprises a silicone-containing crosslinker, such as ac-PDMS. Also preferably, the reactive mixture contains a wetting agent (preferably DMA, PVP, PVMA or mixtures thereof).

The foregoing reactive mixtures may contain optional ingredients such as, but not limited to, one or more initiators, internal wetting agents, crosslinkers, other UV or HEV absorbers, and diluents.

Curing of Hydrogels and Manufacture of Lens

The reactive mixtures may be formed by any of the methods known in the art, such as shaking or stirring, and used to form polymeric articles or devices by known methods. The reactive components are mixed together either with or without a diluent to form the reactive mixture.

For example, ophthalmic devices may be prepared by mixing reactive components, and, optionally, diluent(s), with a polymerization initiator and curing by appropriate conditions to form a product that can be subsequently formed into the appropriate shape by lathing, cutting, and the like. Alternatively, the reactive mixture may be placed in a mold and subsequently cured into the appropriate article.

A method of making a molded ophthalmic device, such as a silicone hydrogel contact lens, may comprise: preparing a reactive monomer mixture; transferring the reactive monomer mixture onto a first mold; placing a second mold on top the first mold filled with the reactive monomer mixture; and curing the reactive monomer mixture by free radical copolymerization to form the silicone hydrogel in the shape of a contact lens.

The reactive mixture may be cured via any known process for molding the reactive mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The contact lenses of this invention may be formed by the direct molding of the silicone hydrogels, which is economical, and enables precise control over the final shape of the hydrated lens. For this method, the reactive mixture is placed in a mold having the shape of the final desired silicone hydrogel and the reactive mixture is subjected to conditions whereby the monomers polymerize, thereby producing a polymer in the approximate shape of the final desired product.

After curing, the lens may be subjected to extraction to remove unreacted components and release the lens from the lens mold. The extraction may be done using conventional extraction fluids, such organic solvents, such as alcohols or may be extracted using aqueous solutions.

Aqueous solutions are solutions which comprise water. The aqueous solutions of the present invention may comprise at least about 20 weight percent water, or at least about 50 weight percent water, or at least about 70 weight percent water, or at least about 95 weight percent water. Aqueous solutions may also include additional water soluble Formulas such as inorganic salts or release agents, wetting agents, slip agents, pharmaceutical and nutraceutical Formulas, combinations thereof and the like. Release agents are compounds or mixtures of compounds which, when combined with water, decrease the time required to release a contact lens from a mold, as compared to the time required to release such a lens using an aqueous solution that does not comprise the release agent. The aqueous solutions may not require special handling, such as purification, recycling or special disposal procedures.

Extraction may be accomplished, for example, via immersion of the lens in an aqueous solution or exposing the lens to a flow of an aqueous solution. Extraction may also include, for example, one or more of: heating the aqueous solution; stirring the aqueous solution; increasing the level of release aid in the aqueous solution to a level sufficient to cause release of the lens; mechanical or ultrasonic agitation of the lens; and incorporating at least one leaching or extraction aid in the aqueous solution to a level sufficient to facilitate adequate removal of unreacted components from the lens. The foregoing may be conducted in batch or continuous processes, with or without the addition of heat, agitation or both.

Application of physical agitation may be desired to facilitate leach and release. For example, the lens mold part to which a lens is adhered can be vibrated or caused to move back and forth within an aqueous solution. Other methods may include ultrasonic waves through the aqueous solution.

The lenses may be sterilized by known means such as, but not limited to, autoclaving.

As indicated above, preferred ophthalmic devices are contact lenses, more preferably soft hydrogel contact lenses. The transmission wavelengths and percentages described herein may be measured on various thicknesses of lenses using, for instance, the methodologies described in the Examples. By way of example, a preferred center thickness for measuring transmission spectra in a soft contact lens may be from 80 to 100 microns, or from 90 to 100 microns or from 90 to 95 microns. Typically, the measurement may be made at the center of the lens using, for instance, a 4 nm instrument slit width. Various concentrations of the one or more polymerizable high energy light absorbing compounds may be used to achieve the transmission characteristics described above. For instance, the concentration may be in the range of at least 1 percent, or at least 2 percent; and up to 10 percent, or up to 5 percent, based on the weight percentages of all components in the reactive mixture, excluding diluent. A typical concentration may be in the range of 3 to 5 percent.

Silicone hydrogel ophthalmic devices (e.g., contact lenses) according to the invention preferably exhibit the following properties. All values are prefaced by "about," and the devices may have any combination of the listed properties. The properties may be determined by methods known to those skilled in the art, for instance as described in United States pre-grant publication US20180037690, which is incorporated herein by reference.

[$H_2O$] %: at least 20%, or at least 25% and/or up to 80% or up to 70%

Haze: 30% or less, or 10% or less

Kruss DCA)(°: 100° or less, or 50° or less

Tensile Modulus (psi): 120 or less, or 80 to 120

Dk (barrers): at least 80, or at least 100, or at least 150, or at least 200

Elongation to Break: at least 100

For ionic silicon hydrogels, the following properties may also be preferred (in addition to those recited above):

Lysozyme uptake (μg/lens): at least 100, or at least 150, or at least 500, or at least 700

Polyquaternium 1 (PQ1) uptake (%): 15 or less, or 10 or less, or 5 or less

Some embodiments of the invention will now be described in detail in the following Examples.

EXAMPLES

Test Methods

Ultraviolet-visible spectra of organic compounds in solution were measured on a Perkin Elmer Lambda 45 or an Agilent Cary 6000i UV/VIS scanning spectrometer. The instrument was thermally equilibrated for at least thirty minutes prior to use. For the Perkin Elmer instrument, the scan range was 200-800 nm; the scan speed was 960 nm per minute; the slit width was 4 nm; the mode was set on transmission or absorbance; and baseline correction was selected. For the Cary instrument, the scan range was 200-800 nm; the scan speed was 600 nm/min; the slit width was 2 nm; the mode was transmission or absorbance; and baseline correction was selected. A baseline correction was performed before samples were analyzed using the autozero function.

Ultraviolet-visible spectra of contact lenses were measured on a Perkin Elmer Lambda 45 UV/VIS or an Agilent Cary 6000i UV/VIS scanning spectrometer using packing solution. The instrument was thermally equilibrated for at least thirty minutes prior to use. For the Perkin Elmer instrument, the scan range was 200-800 nm; the scan speed was 960 nm per minute; the slit width was 4 nm; the mode was set on transmission; and baseline correction was selected. Baseline correction was performed using cuvettes containing plastic two-piece lens holders and the same solvents. These two-piece contact lens holders were designed to hold the sample in the quartz cuvette in the location through which the incident light beam traverses. The reference cuvette also contained a two-piece holder. To ensure that the thickness of the samples is constant, all lenses were made using identical molds. The center thickness of the contact lens was measured using an electronic thickness gauge. Reported center thickness and percent transmission spectra are obtained by averaging three individual lens data.

It is important to ensure that the outside surfaces of the cuvette are completely clean and dry and that no air bubbles are present in the cuvette. Repeatability of the measurement is improved when the reference cuvette and its lens holder remain constant and when all samples use the same sample cuvette and its lens holder, making sure that both cuvettes are properly inserted into the instrument.

The abbreviations used in the Examples and Figures have the following meanings:

$HNO_3$: nitric acid
TsOH: p-toluenesulfonic acid
AcCl: acetyl chloride
HCl: hydrochloric acid
$Et_3N$: triethylamine
DCM: dichloromethane
$SnCl_2$: tin (II) chloride or stannous chloride
$Cu(NO_3)_2$: copper (II) nitrate or cupric nitrate
EtOH: ethanol
$Na_2CO_3$: sodium carbonate
EtOAc: ethyl acetate
BHT: 2,6-bis(1,1-dimethylethyl)-4-methylphenol
$CDCl_3$: deutro-chloroform
$Cs_2CO_3$: cesium or caesium carbonate
$NaHCO_3$: sodium bicarbonate
$Na_2SO_4$: sodium sulfate
$K_2CO_3$: potassium carbonate
DMSO: dimethyl sulfoxide
3-chloropropiophenone (Sigma-Aldrich)
1-(3-hydroxy-4-nitrophenyl)-ethan-1-one (Combi-Blocks)
1-(4-hydroxy-3-nitrophenyl)-ethan-1-one (Combi-Blocks)
BC: back or base curve plastic mold made from PP, TT, Z or blends thereof
FC: front curve plastic mold from PP, TT, Z or blends thereof
PP: polypropylene which is the homopolymer of propylene
TT: Tuftec which is a hydrogenated styrene butadiene block copolymer (Asahi Kasei Chemicals)
Z: Zeonor which is a polycycloolefin thermoplastic polymer (Nippon Zeon Co Ltd)
Da: dalton or g/mole
kDa: kilodalton or an atomic mass unit equal to 1,000 daltons
DMA: N, N-dimethylacrylamide (Jarchem)
HEMA: 2-hydroxyethyl methacrylate (Bimax)
MAA: methacrylic acid (Acros)
PVP: poly(N-vinylpyrrolidone) (ISP Ashland)
PDMA: polydimethylacrylamide
PVMA: polyvinylmethyacetamide
EGDMA: ethylene glycol dimethacrylate (Esstech)
TEGDMA: tetraethylene glycol dimethacrylate (Esstech)
TMPTMA: trimethylolpropane trimethacrylate (Esstech)
Tegomer V-Si 2250: diacryloxypolydimethylsiloxane (Evonik)
Irgacure 1700: mixture of 25% bis(2,6-dimethoxybenzoyl)-2,4,4-trimethyl pentylphosphineoxide and 75% 2-hydroxy-2-methyl-1-phenyl-propan-1-one (BASF)
Irgacure 819: bis(2,4,6-trimethylbenzoyl)-phenylphosphineoxide (BASF)
Irgacure 1870: blend of bis(2,6-dimethoxybenzoyl)-2,4,4-trimethyl-pentylphosphineoxide and 1-hydroxy-cyclohexyl-phenyl-ketone (BASF)
mPDMS: mono-n-butyl terminated monomethacryloxypropyl terminated polydimethylsiloxane ($M_n$=800-1000 daltons) (Gelest)
HO-mPDMS: mono-n-butyl terminated mono-(2-hydroxy-3-methacryloxypropyl)-propyl ether terminated polydimethylsiloxane ($M_n$=400-1500 daltons) (Ortec or DSM-Polymer Technology Group)
SiMAA: 2-propenoic acid, 2-methyl-2-hydroxy-3-[3-[1,3,3,3-tetramethyl-1-[(trimethylsilyl)oxy]disiloxanyl] propoxy]propyl ester (Toray) or 3-(3-(1,1,1,3,5,5,5-heptamethyltrisiloxan-3-yl)propoxy)-2-hydroxypropyl methacrylate
RB247: 1,4-Bis[2-methacryloxyethylamino]-9,10-anthraquinone
D3O: 3,7-dimethyl-3-octanol (Vigon)
DIW: deionized water
MeOH: methanol
IPA: isopropyl alcohol
Norbloc®: 2-(2'-hydroxy-5-methacrylyloxyethylphenyl)-2H-benzotriazole or 3-(2H-benzo[d][1,2,3]triazol-2-yl)-4-hydroxyphenethyl methacrylate CAS #96478-09-0 (Janssen)
TL03 lights: Phillips TLK 40 W/03 bulbs
LED: light emitting diode
L: liter
mL: milliliter
Equiv. or eq.: equivalent
LCMS: Liquid chromatography-mass spectroscopy
kg: kilogram
g: gram
mol: mole
mmol: millimole
TLC: thin layer chromatography
$^1$H NMR: proton nuclear magnetic resonance spectroscopy
UV-VIS: ultraviolet-visible spectroscopy
BAGE: Boric Acid Glycerol Ester (molar ratio of boric acid to glycerol was 1:2) 299.3 grams (mol) of glycerol and 99.8 grams (mol) of boric acid were dissolved in 1247.4 grams of a 5% (w/w) aqueous EDTA solution in a suitable reactor and then heated with stirring to 90-94° C. under mild vacuum (2-6 torr) for 4-5 hours and allowed to cool down to room temperature.
PS: Borate Buffered Packing Solution: 18.52 grams (300 mmol) of boric acid, 3.7 grams (9.7 mmol) of sodium borate decahydrate, and 28 grams (197 mmol) of sodium sulfate were dissolved in enough deionized water to fill a 2-liter volumetric flask.

Example 1—Synthesis of Compound (F) in Scheme 2

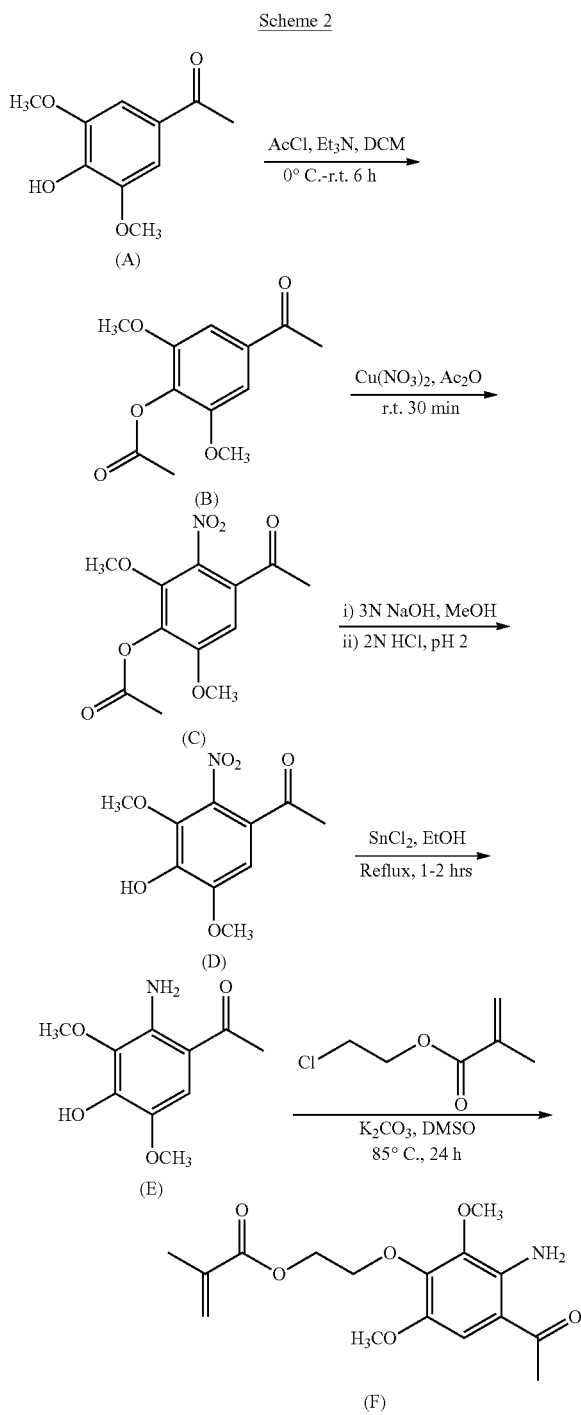

Synthesis of 4-acetyl-2,6-dimethoxyphenyl acetate (B)

4-Hydroxy-3,5-dimethoxyacetophenone (5.0 g, 26.0 mmol) and triethyl amine (5.78 grams, 57.20 mmol) were dissolved in DCM (50 mL) under nitrogen and cooled to 0° C. (ice-bath). Acetyl chloride (2.2 grams, 28.00 mmol) was added drop wise and stirred the reaction mixture at same temperature for 30 min followed by r.t. for 6 hours. Upon completion, water (50 mL) was added and extracted with DCM (3×25 mL), the combined organic extracts were washed with water (50 mL), dried over $Na_2SO_4$, filtered, the solvent was removed under reduce pressure and the residue was recrystallized from DCM/n-hexanes to afford a white solid (95% yield). $^1$H-NMR (CDCl$_3$, 500 MHz): δ 2.36 (s, 3H), 2.60 (s, 3H), 3.89 (s, 6H), 7.23 (s, 2H).

Synthesis of 4-acetyl-2,6-dimethoxy-3-nitrophenyl acetate (C)

4-acetyl-2,6-dimethoxyphenyl acetate (4.22 grams, 17.80 mmol) was dissolved in acetic anhydride (50 mL) with gentle heating (40-45° C.) and Cu(NO$_3$)$_2$ (5.38 grams, 22.30 mmol) was added in one portion and the exotherm was controlled by occasional cooling (ice-bath) over a period of 30-40 minutes. Poured the reaction mixture in ice-water (500 mL) and stirred for 15 minutes, the precipitated solid was filtered, washed with water thoroughly, dried in air and used as it is for the next step. Light brown solid (91% yield). $^1$H-NMR (CDCl$_3$, 500 MHz): δ 2.39 (s, 3H), 2.55 (s, 3H), 3.94 (s, 6H), 6.97 (s, 1H).

Synthesis of 1-(4-hydroxy-3,5-dimethoxy-2-nitrophenyl)ethan-1-one (D)

4-acetyl-2,6-dimethoxy-3-nitrophenyl acetate (4.52 grams, 16.00 mmol) was dissolved in methanol (50 mL) and 3N NaOH (16.1 mL, 48.00 mmol) dropwise. Upon completion, the reaction mixture was cooled to 0° C. (ice-bath) and acidified to pH 2 by the addition of 2N HCl. The precipitated solid was filtered, washed with water thoroughly to afford a white solid (98% yield). $^1$H-NMR (CD$_3$OD, 500 MHz): δ 2.54 (s, 3H), 3.89 (s, 3H), 3.99 (s, 3H), 7.27 (s, 1H).

Synthesis of 1-(2-amino-4-hydroxy-3,5-dimethoxyphenyl)ethan-1-one (E)

1-(4-hydroxy-3,5-dimethoxy-2-nitrophenyl)ethan-1-one (0.95 grams, 4.00 mmol) was suspended in ethanol (20 mL) and methanol (5 mL) was added to dissolve the suspension. SnCl$_2$ (3.74 grams, 19.7 mmol) was added and reaction was heated under reflux conditions for 6 hours. Solvent was removed and 1N NaOH was added dropwise to pH 8 and stirred for 15 minutes, after which the pH 7 was adjusted with 1N HCl. DCM (25 mL) was added and filtered, the residue was washed with DCM (15 mL×3), and the filtrate extracted with DCM (3×15 mL), the combined organic extracts were washed with brine (1×25 mL), dried over Na$_2$SO$_4$, filtered and evaporated. The crude was suspended in hot EtOAc and filtered upon standing on room temperature for 6 h to afford an orange solid (80% yield). $^1$H-NMR (CDCl$_3$, 500 MHz): δ 2.52 (s, 3H), 3.87 (s, 6H), 6.13 (br s, 1H), 6.44 (br s, 2H), 6.92 (s, 1H).

Synthesis of 2-(4-acetyl-3-amino-2,6-dimethoxyphenoxy)ethyl methacrylate (F)

1-(2-amino-4-hydroxy-3,5-dimethoxyphenyl)ethan-1-one (2.00 grams, 9.50 mmol), 2-chloroethyl methacrylate (1.76 grams, 11.90 mmol) and potassium carbonate (1.71 grams, 12.40 mmol) were mixed together in DMSO (25 mL) and heated at 85° C. for 24 h (added 300 ppm BHT). Reaction was cooled to room temperature and water (50 mL)

was added and extracted with EtOAc (3×25 mL), the combined extracts were washed with water (3×15 mL), brine (1×25 mL), dried over Na$_2$SO$_4$, filtered and evaporated under reduced pressure. The crude was passed through a short plug of silica-gel column and eluted with 30% ethyl acetate in n-hexanes to afford a yellow oil (90% yield). $^1$H-NMR (CDCl$_3$, 500 MHz): δ 2.65 (s, 3H), 2.51 (s, 3H), 3.79 (s, 3H), 3.84 (s, 3H), 4.26 (m, 2H), 4.45 (m, 2H), 5.68 (s, 1H), 6.11 (s, 1H), 6.33 (br s, 2H), 6.94 (s, 1H). The UV-VIS spectrum of compound (F) in a 0.2 mM methanol solution is shown in FIG. 1.

Example 2—Synthesis of Compound (M) in Scheme 3

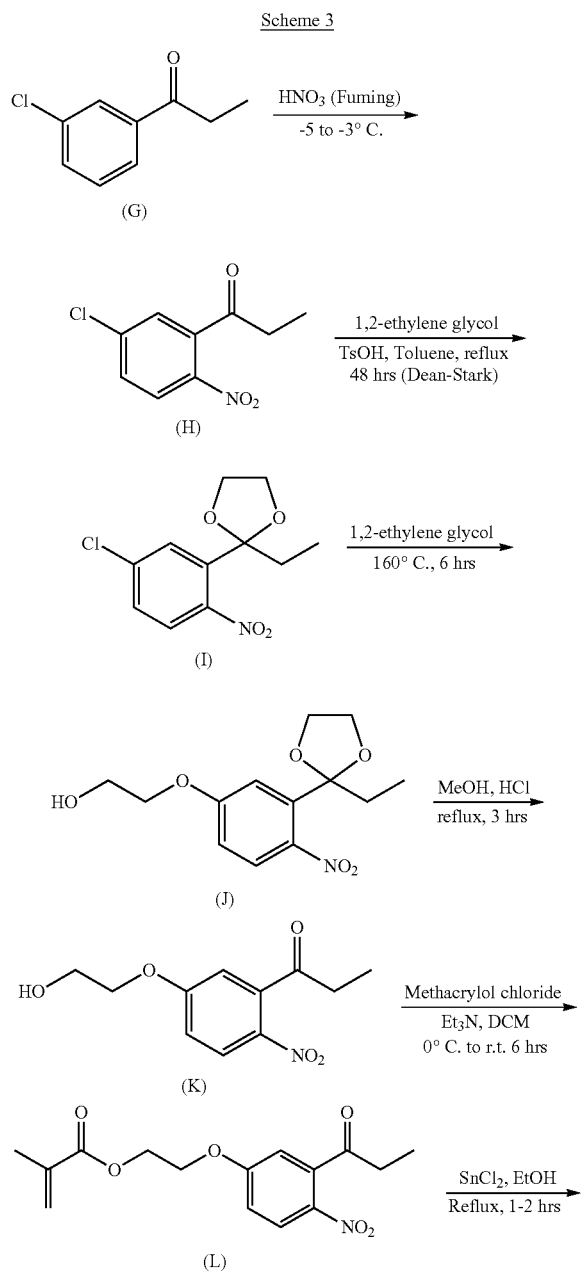

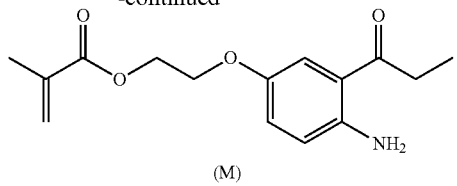

1-(5-Chloro-2-nitrophenyl)propan-1-one (H)

Nitric acid (fuming, 200 mL) was cooled to −5° C. in an ice-salt bath and 3-chloropropiophenone (40.0 grams) was added portion-wise with stirring at a rate that maintained the temperature between −5° C. and −3° C. (using an ice-salt bath). After the addition was completed, the reaction mixture was stirred for another 30 minutes at −3° C. and then poured into ice-water (1000.0 grams). A yellow precipitate was collected by filtration and washed with aqueous NaHCO$_3$ and water thoroughly. Recrystallization from EtOH (300 mL) afforded (H) as light-yellow needles (95% yield). $^1$H-NMR (CDCl$_3$, 500 MHz): δ 1.24 (t, 3H, J=7.0 Hz), 2.78 (m, 2H), 7.32 (s, 1H), 7.55 (m, 1H), 8.08 (d, 1H, J=9.0 Hz).

2-(5-Chloro-2-nitrophenyl)-2-ethyl-1,3-dioxolane (I)

1-(5-Chloro-2-nitrophenyl)propan-1-one (6.5 grams, 30.4 mmol) and anhydrous 1,2-ethylene glycol (4.2 grams, 67.5 mmol) were dissolved in anhydrous toluene (200 mL), and then toluene sulfonic acid (300 mg, catalyst.) dissolved in a few mL of toluene was added. The reaction mixture was refluxed under Dean-Stark conditions for 48 hours. The solvent was removed under reduced pressure; water (25 mL) was added and extracted with EtOAc (3×25 mL). The combined organic extracts were washed with brine (25 mL), dried over Na$_2$SO$_4$, filtered, and evaporated under reduced pressure to afford (I) as off white solid (97% yield). $^1$H-NMR (CDCl$_3$, 500 MHz): δ 0.98 (t, 3H, J=7.1 Hz), 2.16 (m, 2H), 3.70 (m, 2H), 4.01 (m, 2H), 7.37 (m, 2H), 7.60 (m, 1H).

2-(3-(2-Ethyl-1,3-dioxolan-2-yl)-4-nitrophenoxy) ethan-1-ol (J)

2-(5-chloro-2-nitrophenyl)-2-ethyl-1,3-dioxolane (30.69 g, 118.4 mmol) was dissolved in anhydrous 1,2-ethylene glycol (145 mL) at 60° C. Then, Cs$_2$CO$_3$ (33.56 g, 118.4 mmol) was added, and the reaction mixture heated to 165° C. for 6 hours under nitrogen. After the reaction mixture had cooled down to room temperature, DCM (500 mL) and 1N HCl were added (pH=3). The aqueous layer was extracted with more DCM (3×100 mL). The combined organic extracts were washed with brine (50 mL), water (50 mL), dried over Na$_2$SO$_4$, filtered, and concentrated under reduced pressure to afford (J) as a brownish oil (82% yield). 41-NMR (CDCl$_3$, 500 MHz): δ 0.98 (t, 3H, J=7.0 Hz), 2.21 (m, 2H), 3.68 (m, 2H), 3.98 (m, 4H), 4.14 (m, 2H), 6.88 (dd, 1H, J=2.8, 8.8 Hz), 7.12 (d, 2H J=2.8 Hz), 7.44 (d, 1H, J=8.8 Hz).

1-(5-(2-Hydroxyethoxy)-2-nitrophenyl)propan-1-one (K)

2-(3-(2-ethyl-1,3-dioxolan-2-yl)-4-nitrophenoxy)ethan-1-ol (18.0 g, 63.55 mmol) was dissolved in MeOH (180 mL). Concentrated HCl (40 mL) was added, and the solution refluxed for 3 hours. Thereafter, the solvent was removed to one fourth its original volume under reduced pressure and poured into ice-water (500 grams). The precipitate was collected by filtration and recrystallized from EtOH to afford (K) as a brown solid (83% yield). $^1$H-NMR (CDCl$_3$, 500 MHz): δ 1.26 (t, 3H, J=7.3 Hz), 2.75 (m, 2H), 4.02 (m, 2H), 4.19 (m, 2H), 6.77 (d, 2H J=3.0 Hz), 7.02 (dd, 1H, J=3.0, 9.1 Hz), 8.17 (d, 1H, J=9.1 Hz).

2-(4-Nitro-3-propionylphenoxy)ethyl methacrylate (L)

1-(5-(2-Hydroxyethoxy)-2-nitrophenyl)propan-1-one (8.0 grams, 33.4 mmol) and triethyl amine (7.45 g, 73.60 mmol) were dissolved in DCM (180 mL) and cooled to 0° C. (ice-bath). Methacryloyl chloride (3.85 g, 36.78 mmol, containing 300 ppm BHT) was added drop-wise with stirring under a nitrogen atmosphere keeping the temperature at 0° C. for 30 minutes. The reaction mixture was allowed to warm up to room temperature and then stirred for another 6 hours. Water (50 mL) was added, and the aqueous layer further extracted with DCM (3×50 mL). The combined organic extracts were washed with water (50 mL), dried over Na$_2$SO$_4$, filtered, and concentrated under reduce pressure. The residue was recrystallized from EtOH (50 mL) to afford (L) as a light yellow solid (85% yield). $^1$H-NMR (CDCl$_3$, 500 MHz): δ 1.26 (t, 3H, J=7.2 Hz), 1.95 (s, 3H), 2.76 (m, 2H), 4.33 (m, 2H), 4.53 (m, 2H), 5.62 (s, 1H), 6.14 (s, 1H), 6.78 (d, 2H J=2.9 Hz), 7.02 (dd, 1H, J=2.9, 8.9 Hz), 8.17 (d, 1H, J=8.9 Hz).

2-(4-Amino-3-propionylphenoxy)ethyl methacrylate (M)

2-(4-Nitro-3-propionylphenoxy)ethyl methacrylate (14.29 grams, 46.50 mmol) was dissolved in EtOH (200 mL, containing 300 ppm BHT) with some heating. SnCl$_2$ (44.1 grams, 233.0 mmol) was added, and the reaction mixture refluxed for 1-2 hours. The reaction mixture was cooled to room temperature, and 5% aqueous solution of Na$_2$CO$_3$ was added making the reaction mixture's pH 8.0. EtOAc (200 mL) was added, and resulting suspension was filtered to remove the precipitated metal salts. The filtrate was extracted with EtOAc (3×100 mL), and the combined organic extracts were washed with brine (50 mL), dried over Na$_2$SO$_4$, filtered and concentrated under reduce pressure. The crude product was purified by recrystallization from EtOH (75 mL) to afford (M) as a light yellow solid (98% yield). $^1$H-NMR (CDCl$_3$, 500 MHz): δ 1.20 (t, 3H, J=7.0 Hz), 1.96 (s, 3H), 2.95 (m, 2H), 4.19 (m, 2H), 4.47 (m, 2H), 5.60 (s, 1H), 6.15 (s, 1H), 6.62 (d, 2H J=9.0 Hz), 7.02 (dd, 1H, J=3.0, 9.0 Hz), 8.17 (d, 1H, J=3.0 Hz). The UV-VIS spectrum of compound (M) in a 0.2 mM methanol solution is shown in FIG. 1.

Example 3—Synthesis of Compound (P) in Scheme 4

Scheme 4

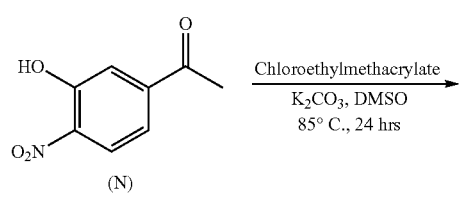

(N)

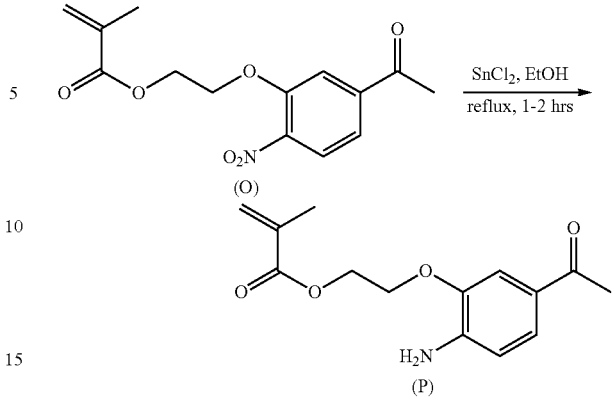

2-(5-Acetyl-2-nitrophenoxy)ethyl methacrylate (O)

3-Hydroxy-4-nitroacetophenone (2.5 grams, 13.8 mmol) was dissolved in DMSO (25 mL), and then K$_2$CO$_3$ (2.98 g, 21.6 mmol) was added followed by 2-chloroethyl methacrylate (3.04 grams, 20.5 mmol). The reaction mixture was heated at 85° C. for 24 hours. Water was added and extracted with DCM (3×25 mL). The combined organic extracts were washed with brine (50 mL), dried over Na$_2$SO$_4$, filtered, and concentrated under reduce pressure. The crude product was purified by recrystallization from Et$_0$H (30 mL) to afford (O) as a light yellow solid (90% yield). $^1$H-NMR (CDCl$_3$, 500 MHz): δ 1.95 (s, 3H), 2.61 (s, 3H), 4.44 (m, 2H), 4.57 (m, 2H), 5.61 (s, 1H), 6.15 (s, 1H), 7.17 (d, 2H J=9.0 Hz), 8.15 (dd, 1H, J=1.5, 9.0 Hz), 8.41 (d, 1H, J=1.5 Hz).

2-(5-Acetyl-2-aminophenoxy)ethyl methacrylate (P)

2-(5-Acetyl-2-nitrophenoxy)ethyl methacrylate (0.8 grams, 2.73 mmol) was dissolved in Et$_0$H (25 mL, containing 300 ppm BHT) with some heating. SnCl$_2$ (2.59 grams, 13.7 mmol) was added, and the reaction mixture refluxed for 1-2 hours. The reaction mixture was cooled to room temperature, and 5% aqueous solution of Na$_2$CO$_3$ was added making the reaction mixture's pH 8.0. EtOAc (25 mL) was added, and resulting suspension was filtered to remove the precipitated metal salts. The filtrate was extracted with EtOAc (3×20 mL), and the combined organic extracts were washed with brine (20 mL), dried over Na$_2$SO$_4$, filtered, and concentrated under reduce pressure. The crude product was purified by recrystallization from Et$_0$H (20 mL) to afford (P) as a light yellow solid (80% yield). $^1$H-NMR (CDCl$_3$, 500 MHz): δ 1.96 (s, 3H), 2.53 (s, 3H), 4.32 (m, 2H), 4.57 (m, 2H), 5.60 (s, 1H), 6.15 (s, 1H), 6.80 (d, 2H J=8.5 Hz), 7.35 (m, 2H). The UV-VIS spectrum of compound (P) in a 0.2 mM methanol solution is shown in FIG. 1.

Example 4

Reactive monomer mixtures (4A, 4B, and 4C) were prepared, composed of 77 weight percent of the formulations listed in Table 4 and 23 weight percent of the diluent D30. All components except the PVP were mixed in a jar under a nitrogen atmosphere at ambient temperature for about 90 minutes, after which the PVP was added and mixed for about 240 minutes at ambient temperature. Thereafter, the jar was capped and placed on a roller for about 1000-1500 minutes at room temperature. Ambient and room temperatures are typically between 25-30° C. The reactive monomer mixtures were then filtered through a 3 µm filter using a stainless-steel syringe under pressure. All reactive monomer mixtures were degassed at ambient temperature by applying vacuum (40 torr) for 45 minutes prior to making contact lenses.

TABLE 4

| Component | 4A (wt. %) | 4B (wt. %) | 4C (wt. %) |
|---|---|---|---|
| mPDMS 1000 | 31.4 | 30.43 | 31.17 |
| SiMAA | 28.35 | 27.48 | 28.14 |
| DMA | 24.31 | 23.56 | 24.13 |
| HEMA | 6.08 | 5.89 | 6.04 |
| TEGDMA | 1.5 | 1.47 | 1.47 |
| PVP K90 | 7 | 6.87 | 6.87 |
| Irgacure 1870 | 0.34 | 0 | 0.33 |
| Irgacure 1850 | 0 | 0.47 | 0 |
| Norbloc | 1 | 1.96 | 0 |
| Compound (F) | 0 | 1.84 | 0 |
| Compound (M) | 0 | 0 | 1.85 |
| Σ Components | 100 | 100 | 100 |

In a glove box with a nitrogen gas atmosphere and less than about 0.2 percent oxygen gas, about 75-100 µL of the reactive monomer mixture (4A) were dosed using an Eppendorf pipet at room temperature into the FC made of 90:10 Z:TT blend. The BC made of 90:10 Z:TT blend was then placed onto the FC. The molds were equilibrated for a minimum of twelve hours in the glove box prior to dosing. Trays containing eight mold assemblies each were transferred into an adjacent glove box maintained at 63° C., and a quartz plate was used to cover and secure the mold assemblies in the trays. Lenses were cured from the top and the bottom for 10 minutes using 435 nm LED lights having an intensity of about 2.1 mW/cm² at the tray's location.

The lenses were manually de-molded with most lenses adhering to the FC and released by suspending the lenses in about one liter of 70 percent IPA for about one or two hours, followed by washing two times with 70 percent IPA and then three times with DI water. Each washing step lasted about 30 minutes. The lenses (4A) were equilibrated in borate buffered packaging solution overnight and then stored in fresh borate buffered packaging solution thereafter. The average center thickness of these lenses was 87 microns.

Lenses were made similarly from reactive monomer mixture (4B) except that the cure temperature was 64° C. and the intensity was 1.5 mW/cm². The average center thickness of these lenses was 88 microns.

Lenses were made identically from reactive monomer mixture (4C); all curing, hydration, and center thickness values were identical.

The UV-VIS transmission spectra of lenses (4A), (4B) and (4C) are shown in FIG. 2.

Example 5

Two reactive monomer mixtures (Batches A and B) were prepared, composed of 77 weight percent of the formulations listed in Table 5 and 23 weight percent of the diluent D30. All components except the PVP were mixed in a jar under a nitrogen atmosphere at ambient temperature for about 90 minutes, after which the PVP was added and mixed for about 240 minutes at ambient temperature. Thereafter, the jar was capped and placed on a roller for about 1000-1500 minutes at room temperature. Ambient and room temperatures are typically between 25-30° C. The reactive monomer mixtures were then filtered through a 3 µm filter using a stainless-steel syringe under pressure. All reactive monomer mixtures were degassed at ambient temperature by applying vacuum (40 torr) for 45 minutes prior to making contact lenses.

TABLE 5

| Component | Batch A (wt. %) | Batch B (wt. %) |
|---|---|---|
| mPDMS 1000 | 31.22 | 30.69 |
| SiMAA | 27.97 | 27.50 |
| DMA | 24.10 | 23.70 |
| HEMA | 6.05 | 5.95 |
| TEGDMA | 1.5 | 1.5 |
| PVP K90 | 6.8 | 6.8 |
| Irgacure 1870 | 0.34 | 0.34 |
| RG247 | 0.2 | 0.2 |
| Norbloc | 0 | 1.5 |
| Compound (F) | 2 | 2 |
| Σ Components | 100 | 100 |

In a glove box with a nitrogen gas atmosphere and less than about 0.5 percent oxygen gas, about 75 µL of Batch A were dosed using an Eppendorf pipet at room temperature into the FC made of 90:10 (w/w) Z:TT blend. The BC made of 90:10 (w/w) Z:TT blend was then placed onto the FC. The molds were equilibrated for a minimum of twelve hours in the glove box prior to dosing. Trays containing eight mold assemblies each were transferred into an adjacent glove box maintained at 65° C., and a quartz plate was used to cover and secure the mold assemblies in the trays. The lenses were cured from the top and the bottom for 15 minutes using 435 nm LED lights having an intensity of about 2.0 mW/cm² at the tray's location.

The lenses were manually de-molded with most lenses adhering to the FC and released by suspending the lenses in about one liter of 70 percent IPA for about one hour, followed by washing once with 70 percent IPA for about 30 minutes, and then two times with DI water with each step lasting about 15 minutes. The lenses (5A) were then equilibrated in borate buffered packaging solution for about 30 minutes and then stored in fresh borate buffered packaging solution thereafter. The average center thickness of these lenses was 89 microns.

A mixture of 8.03 grams of Batch A and 4.02 grams of Batch B was degassed at ambient temperature by applying vacuum (40 torr) for 45 minutes. Then, lenses (5B) were made following the same curing and hydration steps as described above. The average center thickness of these lenses was 87 microns.

A mixture of 4.01 grams of Batch A and 8.02 grams of Batch B was degassed at ambient temperature by applying vacuum (40 torr) for 45 minutes. Then, lenses (5C) were made following the same curing and hydration steps as described above. The average center thickness of these lenses was 88 microns.

Batch B was degassed at ambient temperature by applying vacuum (40 torr) for 45 minutes. Then, lenses (5D) were made following the same curing and hydration steps as described above. The average center thickness of these lenses was 90 microns.

In this way, lenses comprising 2 weight percent of compound (F) and different amounts of Norbloc® were prepared. Lenses (5A) contained no Norbloc® while lenses (5B) contained 0.5 weight percent Norbloc®, (5C) contained 1 weight percent Norbloc®, and (5D) contained 1.5 weight percent Norbloc®. The UV-VIS transmission spectra of these lenses are shown in FIG. 3, demonstrating that silicone hydrogel contact lenses with about 2 weight percent of compound (F) and about 0.5 weight percent Norbloc® exhibit nearly complete absorption between about 250 nm and about 400 nm while absorbing some high energy visible light between about 400 nm and about 450 nm. Increasing the weight percent of Norbloc® to about 1 weight percent provided complete absorption between about 250 nm and about 400 nm while absorbing some high energy visible light between about 400 nm and about 450 nm.

Example 6

A reactive monomer mixture (Batch C) was prepared, composed of 52 weight percent of the formulation listed in Table 6 and 48 weight percent of the diluent BAGE. The components were mixed in ajar under a nitrogen atmosphere at ambient temperature. Thereafter, the jar was capped and placed on a roller for 1379 minutes at ambient temperature. The reactive monomer mixture was then filtered through a 3 μm filter using a stainless steel syringe under pressure.

TABLE 6

| Component | Batch C (wt. %) |
| --- | --- |
| HEMA | 94.91 |
| MAA | 1.94 |
| EGDMA | 0.77 |
| TMPTMA | 0.09 |
| Blue HEMA | 0.01 |
| Irgacure 1700 | 1.33 |
| Norbloc ® | 0.95 |
| Σ Components | 100 |

Batch C was degassed at ambient temperature by applying vacuum (40 torr) for 45 minutes. Then, in a glove box with a nitrogen gas atmosphere and less than about 0.2 percent oxygen gas, about 75 μL of the reactive mixture were dosed using an Eppendorf pipet at room temperature into the FC made of 90:10 Z:TT blend. The BC made of 90:10 Z:TT blend was then placed onto the FC. The molds were equilibrated for a minimum of twelve hours in the glove box prior to dosing. Trays containing eight mold assemblies each were transferred into an adjacent glove box maintained at 65° C., and a quartz plate was used to cover and secure the mold assemblies in the trays. Lenses were cured from the top and the bottom for 8 minutes using 435 nm LED lights having an intensity of about 2.1 mW/cm$^2$ at the tray's location.

The lenses (6A) were manually de-molded with most lenses adhering to the FC and released by suspending the lenses in 30 percent IPA for about 30-60 minutes, followed by soaking in DIW for 30 minutes and then in PS for 30 minutes. The lenses were still somewhat tacky, so the lenses were soaked again in DIW and individually placed in vial containing PS ( ). The average center thickness of these lenses was 86 microns. A person of ordinary skill recognizes that the exact lens release process can be varied depending on the lens formulation and mold materials, regarding the concentrations of the aqueous isopropanol solutions, the number of washings with each solvent, and the duration of each step. The purpose of the lens release process is to release all of the lenses without defects and transition from diluent swollen networks to the packaging solution swollen hydrogels.

17.8 Milligrams of compound (M) was dissolved in 6.885 grams of Batch C to yield a reactive monomer mixture containing about 0.5 weight percent of compound (M). Lenses (6B) were prepared using the same curing conditions and hydration steps as used to make the previous lenses (6A). The average center thickness of these lenses was 86 microns.

45.3 Milligrams of compound (M) was dissolved in 4.442 grams of Batch C to yield a reactive monomer mixture containing about 2 weight percent of compound (M). Lenses (6C) were prepared using the same curing conditions and hydration steps as used to make the previous lenses (6A). The average center thickness of these lenses was 86 microns.

The UV-VIS transmission spectra of lenses (6A), (6B) and (6C) are shown in FIG. 4, demonstrating that conventional hydrogel contact lenses with about 2 weight percent of compound (M) and about 1 weight percent Norbloc® exhibit nearly complete absorption between about 250 nm and about 400 nm while absorbing some high energy visible light between about 400 nm and about 450 nm. Increasing the concentration of compound (M) in the formulation may provide complete absorption between about 250 nm and about 400 nm while absorbing some high energy visible light between about 400 nm and about 450 nm.

Example 7

Lenses were made using the reactive monomer mixture comprising the components listed as Batch B in Table 5 and same curing and hydration steps as example 5. Lenses were packaged in glass vials containing PS and then placed either on a window sill with direct sunlight (7A) or on top of a cabinet without exposure to direct sunlight, only indoor lighting (7B). Controls were stored in the dark. After 3, 5, 9, 15, and 21 weeks of exposure, UV-Visible transmission spectra of the lenses were measured as shown in FIG. 5 and FIG. 6.

For lenses exposed to direct sunlight, the absorption of high energy visible light changed over time. In the first nine weeks, the percent of light transmission at 400 nm changed from about 5% to about 17%. After fifteen weeks of sunlight exposure, the percent of light transmission at 400 nm increased to about 44%; after twenty-one weeks, to about 90%. Based on these data, silicone hydrogel contact lenses comprising compound (F) may not require extraordinary packaging or special handling instructions other than the requirement not to store lenses in direct sunlight.

For lenses exposed to indoor lighting, the absorption of high energy visible light between 400 nm and 450 nm did not change significantly over time. For instance, the change in transmittance at 450 nm between week zero and week 21 was less than 5%.

Example 8 (Prophetic)

A reactive monomer mixture (Batch D) is prepared, composed of 52 weight percent of the formulation listed in Table 7 and 48 weight percent of the diluent BAGE. The components are mixed in ajar under a nitrogen atmosphere at ambient temperature. Thereafter, the jar is capped and placed on a roller for about 1400 minutes at ambient temperature. The reactive monomer mixture is then filtered through a 3 μm filter using a stainless steel syringe under pressure.

TABLE 7

| Component | Batch D (wt. %) |
|---|---|
| HEMA | 94.91 |
| MAA | 1.94 |
| EGDMA | 0.77 |
| TMPTMA | 0.09 |
| Blue HEMA or RG247 | 0.01 |
| Irgacure 1700 | 1.33 |
| Norbloc ® | 0.95 |
| Σ Components | 100 |

Batch D is degassed at ambient temperature by applying vacuum (40 torr) for 45 minutes. Then, in a glove box with a nitrogen gas atmosphere and less than about 0.2 percent oxygen gas, about 75 µL of the reactive mixture are dosed using an Eppendorf pipet at room temperature into the FC made of 90:10 Z:TT blend. The BC made of 90:10 Z:TT blend is then placed onto the FC. The molds are equilibrated for a minimum of twelve hours in the glove box prior to dosing. Trays containing eight mold assemblies each are transferred into an adjacent glove box maintained at about 65° C., and a quartz plate is used to cover and secure the mold assemblies in the trays. Lenses are cured from the top and the bottom for about 8 minutes using 435 nm LED lights having an intensity of about 2 mW/cm² at the tray's location.

The lenses (8A) are manually de-molded and released by suspending the lenses in 30 percent IPA for about 30-60 minutes, followed by soaking in DIW for 30 minutes and then in PS for 30 minutes. A person of ordinary skill recognizes that the exact lens release process can be varied depending on the lens formulation and mold materials, regarding the concentrations of the aqueous isopropanol solutions, the number of washings with each solvent, and the duration of each step. The purpose of the lens release process is to release all of the lenses without defects and transition from diluent swollen networks to the packaging solution swollen hydrogels.

About 50 milligrams of compound (F) is dissolved in about 10 grams of Batch D to yield a reactive monomer mixture containing about 0.5 weight percent of compound (F). Lenses (8B) may be prepared using the same curing conditions and hydration steps as used to make the previous lenses (8A).

About 200 milligrams of compound (F) is dissolved in about 10 grams of Batch D to yield a reactive monomer mixture containing about 2 weight percent of compound (F). Lenses (8C) may be prepared using the same curing conditions and hydration steps as used to make the previous lenses (8A).

Examples 9-11 (Prophetic)

Contact lenses from the silicone hydrogel formulations shown in Table 8 can be prepared using analogous procedures to those described in Example 5. In these examples, reactive monomer mixtures are prepared, comprising about 77 weight percent of the formulations listed in Table 8 and about 23 weight percent of a diluent (e.g., D30).

TABLE 8

| Component | Ex 9 (weight %) | Ex. 10 (weight %) | Ex. 11 (weight %) |
|---|---|---|---|
| OH-mPDMS (n = 15) | 28.00 | 28.50 | 28.00 |
| OH-mPDMS (n = 4) | 25.00 | 25.50 | 25.00 |
| ac-PDMS | 5.00 | 4.00 | 5.00 |
| DMA | 24.00 | 20.00 | 20.00 |
| HEMA | 7.98 | 7.98 | 7.98 |
| RB247 | 0.02 | 0.02 | 0.02 |
| PDMA ($M_w$ = 740kDa) | 5.00 | 0 | 0 |
| PVP K90 | 0 | 7.00 | 9.00 |
| PVMA ($M_w$ = 570kDa) | 0 | 2.00 | 0 |
| EGDMA | 0.25 | 0.25 | 0.25 |
| Compound (F) | 3.00 | 3.00 | 3.00 |
| Norbloc ® | 1.50 | 1.50 | 1.50 |
| Irgacure 1870 | 0.25 | 0.25 | 0.25 |
| Σ Components | 100 | 100 | 100 |

Example 12

Synthesis of (Z)-3-hydroxy-1-(naphthalen-2-yl)-3-(4-vinylphenyl)prop-2-en-1-one (N) as Shown in Scheme 5

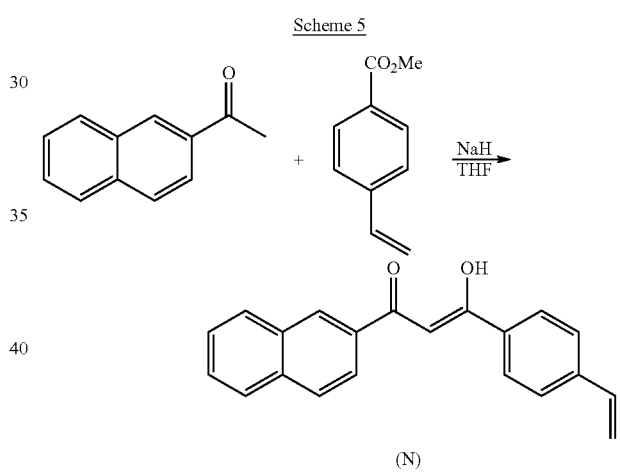

To a 250 mL round bottomed flask containing a magnetic stirring bar, methyl 4-vinylbenzoate (2 grams, 12.3 mmol) and NaH (4.9 gram, 10 eq. 60% sodium hydride in oil suspension) were added. A pressure equalizing addition funnel containing 50 mL of dried THF (molecular sieves) was attached, and the reaction system purged with dry nitrogen gas for 20 minutes. Thereafter, the THF was added slowly with vigorous stirring. 2-Acetonaphthone (3.5 grams, 12.3 mmol) and a small amount of hydroquinone were dissolved in 10 mL dried THF and added dropwise to the reaction mixture. The contents of the reaction vessel were stirred for 12 hours. Then, the reaction flask was placed in an ice bath, and aqueous hydrochloric acid was added slowly to react with excess NaH. The volatile components were removed by rotary evaporation, and the residual dissolved/suspended in DCM. After filtration, the organic layer was extracted with dichloromethane in a separatory funnel, washed with dilute hydrochloric acid and brine, and then dried over MgSO₄. After filtration, the solvent was removed by rotary evaporation. The residual was dissolved in ethyl acetate. The unreacted acetonaphthone was removed by precipitation into excess hexanes. The crude product was isolated by filtration and rotary evaporation which was then further purified using a silica column with ethyl acetate/hexane (1:5) as eluent, yielding (Z)-3-hydroxy-1-(naphthalen-2-yl)-3-(4-vinylphenyl)prop-2-en-1-one (N). $^1$H NMR (500 MHz, CDCl$_3$) δ 5.40 (1H, d, J=11.0 Hz, vinylic), 5.91 (1H, d, J=17.5 Hz, vinylic), 6.79 (1H, dd, J=11.0 Hz, J=17.5 Hz, vinylic), 6.99 (1H, s, enol H—C═C—O—), 7.52-8.03 (10H, m, Ar—H), 8.54 (1H, s, Ar—H); note: the exchangeable enolic proton was not observed.

A reactive monomer mixture (RMM) was prepared, composed of 77 weight percent of the formulation listed in Table 9 and 23 weight percent of the diluent D30. All components except the PVP were mixed in a jar under a nitrogen atmosphere at ambient temperature for about 90 minutes, after which the PVP was added and mixed for about 240 minutes at ambient temperature. Thereafter, the jar was capped and placed on a roller for about 1000-6000 minutes at room temperature until a homogeneous solution was obtained, typically around 1500 to 1600 minutes. Ambient and room temperatures are typically between 25-30° C. The reactive monomer mixtures were then filtered through a 3 μm filter using a stainless-steel syringe under pressure. All reactive monomer mixtures were degassed at ambient temperature by applying vacuum (40 torr) for 45 minutes prior to making contact lenses.

TABLE 9

| Component | Weight % |
|---|---|
| mPDMS 1000 | 31.08 |
| SiMAA | 28.07 |
| DMA | 24.06 |
| HEMA | 5.93 |
| TEGDMA | 1.5 |
| PVP K90 | 7 |
| Irgacure 1870 | 0.34 |
| Bisomer IMT Blue | 0.02 |
| Compound (A) | 2 |
| Σ Components | 100 |

In a glove box with a nitrogen gas atmosphere and less than about 0.2 percent oxygen gas, about 75-100 μL of the RMM were dosed using an Eppendorf pipet at room temperature into the FC made of 90:10 Z:TT blend. The BC made of 90:10 Z:TT blend was then placed onto the FC. The molds were equilibrated for a minimum of twelve hours in the glove box prior to dosing. Trays containing eight mold assemblies each were transferred into an adjacent glove box maintained at 65° C., and a quartz plate was used to cover and secure the mold assemblies in the trays. Lenses were cured from the top and the bottom using 1.0 mW/cm$^2$ for about 5 minutes and then 2.5 mW/cm$^2$ for about 10 minutes using 435 nm LED lights.

The lenses were manually de-molded with most lenses adhering to the FC and released by suspending the lenses in about one liter of 70 percent IPA for about one or two hours, followed by washing two times with 70 percent IPA and then three times with deionized water. Each washing step lasted about 30 minutes. The lenses were equilibrated in borate buffered packaging solution overnight and then stored in fresh borate buffered packaging solution thereafter. The average center thickness of these lenses was about 85 microns.

The UV-VIS transmission spectra of lenses (Example 12) are shown in FIG. 7, demonstrating that silicone hydrogel contact lenses with 2 weight percent of compound (N) exhibits complete absorption between about 250 nm and about 400 nm while absorbing some blue light between about 400 nm and about 450 nm.

We claim:

1. An ophthalmic device that is a free radical reaction product of a reactive mixture comprising: one or more monomers suitable for making the ophthalmic device; and a polymerizable high energy light absorbing compound comprising a compound of formula I:

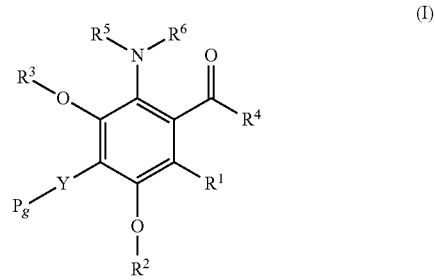

wherein:
Y is a $C_1$-$C_8$ alkylene, alkyleneoxy, $C_1$-$C_8$ oxaalkylene, $C_1$-$C_8$ thiaalkylene, $C_1$-$C_8$ alkylene-ester-$C_1$-$C_8$ alkylene, $C_1$-$C_8$ alkylene-amide-$C_1$-$C_8$ alkylene, or $C_1$-$C_8$ alkylene-amine-$C_1$-$C_8$ alkylene group;
$P_g$ is a styryl, vinyl carbonate, vinyl ether, vinyl carbamate, N-vinyl lactam, N-vinylamide, (meth)acrylate, or (meth)acrylamide group;
$R^1$ is H or $C_1$-$C_6$ alkyl;
$R^2$ and $R^3$ are independently $C_1$-$C_6$ alkyl;
$R^4$ is $C_1$-$C_6$ alkyl; and
$R^5$ and $R^6$ are independently H or $C_1$-$C_6$ alkyl.

2. The ophthalmic device of claim 1 wherein $R^1$ is H.

3. The ophthalmic device of claim 1 wherein $R^5$ and $R^6$ are independently H or methyl.

4. The ophthalmic device of claim 1 wherein $R^2$, $R^3$, and $R^4$ are independently $C_1$-$C_3$ alkyl.

5. The ophthalmic device of claim 1 wherein the compound of of formula I is:
2-(4-acetyl-3-amino-2,6-dimethoxyphenoxy)ethyl methacrylate;
2-((4-acetyl-3-amino-2,6-dimethoxyphenyl)thio)ethyl methacrylate;
2-((4-acetyl-3-amino-2,6-dimethoxyphenyl)(methyl)amino)ethyl methacrylate;
2-((4-acetyl-3-amino-2,6-dimethoxyphenyl)amino)ethyl methacrylate;
N-(2-(4-acetyl-3-amino-2,6-dimethoxyphenoxy)ethyl)methacrylamide;
N-(2-((4-acetyl-3-amino-2,6-dimethoxyphenyl)thio)ethyl)methacrylamide;
N-(2((4-acetyl-3-amino-2,6-dimethoxyphenyl)amino)ethyl)methacrylamide;
N-(2-((4-acetyl-3-amino-2,6-dimethoxyphenyl)(methyl)amino)ethyl)methacrylamide;
N-(2-(4-acetyl-3-amino-2,6-dimethoxyphenoxy)ethyl)acrylamide;
N-(2-((4-acetyl-3-amino-2,6-dimethoxyphenyl)thio)ethyl)acrylamide;
N-(2-((4-acetyl-3-amino-2,6-dimethoxyphenyl)amino)ethyl)acrylamide;
N-(2-((4-acetyl-3-amino-2,6-dimethoxyphenyl)(methyl)amino)ethyl)acrylamide 3-(4-acetyl-3-amino-2,6-dimethoxyphenyl)propyl methacrylate N-(3-(4-acetyl-3-amino-2,6-dimethoxyphenyl)propyl)methacrylamide 4-acetyl-3-amino-2,6-dimethoxyphenethyl methacrylate; or N-(4-acetyl-3-amino-2,6-dimethoxyphenethyl)methacrylamide.

6. The ophthalmic device of claim 1 further comprising a second polymerizable high energy light absorbing compound.

7. The ophthalmic device of claim 6 wherein the second polymerizable high energy light absorbing compound is a UV absorbing compound.

8. The ophthalmic device of claim 7 wherein the UV absorbing compound comprises a compound of formula I, a benzophenone, a benzotriazole, a triazine, a substituted acrylonitrile, a salicyclic acid derivative, a benzoic acid derivative, a cinnamic acid derivative, a chalcone derivative, a dypnone derivative, a crotonic acid derivative, or mixtures thereof.

9. The ophthalmic device of claim 1 wherein the monomer suitable for making the ophthalmic device comprises a hydrophilic component, a silicone-containing component, or mixtures thereof.

10. The ophthalmic device of claim 1 that is a contact lens, a corneal onlay, a corneal inlay, an intraocular lens, or an overlay lens.

11. The ophthalmic device of claim 1 that is a hydrogel contact lens.

12. A method for making the ophthalmic device of claim 1, the method comprising:
  (a) providing a reactive mixture containing the compound of formula I, one or more device forming monomers, and a radical initiator; and
  (b) polymerizing the reactive mixture to form the ophthalmic device.

* * * * *